US008445528B2

(12) United States Patent
Baker, Jr. et al.

(10) Patent No.: US 8,445,528 B2
(45) Date of Patent: *May 21, 2013

(54) DENDRIMER CONJUGATES

(75) Inventors: James R. Baker, Jr., Ann Arbor, MI (US); Xue-min Cheng, Ann Arbor, MI (US); Thommey P. Thomas, Dexter, MI (US); Baohua Mark Huang, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/547,929

(22) Filed: Jul. 12, 2012

(65) Prior Publication Data

US 2012/0277376 A1    Nov. 1, 2012

Related U.S. Application Data

(63) Continuation of application No. 12/403,179, filed on Mar. 12, 2009, now Pat. No. 8,252,834.

(60) Provisional application No. 61/035,949, filed on Mar. 12, 2008.

(51) Int. Cl.
*A61K 31/403* (2006.01)
*A61K 31/485* (2006.01)
*C07D 209/12* (2006.01)
*C07D 471/04* (2006.01)

(52) U.S. Cl.
USPC ............. 514/412; 514/282; 548/452; 546/45; 977/754; 424/400; 424/486

(58) Field of Classification Search
USPC ............. 514/282; 548/452; 546/45; 977/754; 424/400, 486
See application file for complete search history.

(56) References Cited

U.S. PATENT DOCUMENTS

| | | |
|---|---|---|
| 4,161,948 A | 7/1979 | Bichon |
| 4,507,466 A | 3/1985 | Tomalia |
| 4,558,120 A | 12/1985 | Tomalia |
| 4,568,737 A | 2/1986 | Tomalia |
| 4,587,329 A | 5/1986 | Tomalia |
| 4,631,337 A | 12/1986 | Tomalia |
| 4,694,064 A | 9/1987 | Tomalia et al. |
| 4,708,930 A | 11/1987 | Kortright |
| 4,713,975 A | 12/1987 | Tomalia |
| 4,737,550 A | 4/1988 | Tomalia |
| 4,743,543 A | 5/1988 | Kortright |
| 4,827,945 A | 5/1989 | Groman |
| 4,857,599 A | 8/1989 | Tomalia |
| 4,871,779 A | 10/1989 | Killat |
| 4,892,935 A | 1/1990 | Yoshida |
| 4,914,021 A | 4/1990 | Toth |
| 4,918,164 A | 4/1990 | Hellstrom |
| 4,921,789 A | 5/1990 | Salem |
| 4,921,790 A | 5/1990 | Obrien |
| 4,939,240 A | 7/1990 | Chu |
| 4,946,778 A | 8/1990 | Ladner |
| 4,963,484 A | 10/1990 | Kufe |
| 4,965,128 A | 10/1990 | Greidanus |
| 5,041,516 A | 8/1991 | Frechet et al. |
| 5,053,489 A | 10/1991 | Kufe |
| 5,110,911 A | 5/1992 | Samuel |
| 5,270,163 A | 12/1993 | Gold |
| 5,338,532 A | 8/1994 | Tomalia |
| 5,354,308 A | 10/1994 | Simon |
| 5,387,617 A | 2/1995 | Hedstrand |
| 5,393,795 A | 2/1995 | Hedstrand |
| 5,393,797 A | 2/1995 | Hedstrand |
| 5,475,096 A | 12/1995 | Gold |
| 5,512,443 A | 4/1996 | Schlom |
| 5,527,524 A | 6/1996 | Tomalia |
| 5,545,530 A | 8/1996 | Satomura |
| 5,560,929 A | 10/1996 | Hedstrand |
| 5,631,329 A | 5/1997 | Yin |
| 5,661,025 A | 8/1997 | Szoka |
| 5,674,192 A | 10/1997 | Sahatjian |
| 5,693,014 A | 12/1997 | Abele |
| 5,693,763 A | 12/1997 | Codington |
| 5,714,166 A | 2/1998 | Tomalia |
| 5,733,303 A | 3/1998 | Israel |
| 5,755,722 A | 5/1998 | Barry |
| 5,773,527 A | 6/1998 | Tomalia |
| 5,792,105 A | 8/1998 | Lin |
| 5,795,582 A | 8/1998 | Wright |

(Continued)

FOREIGN PATENT DOCUMENTS

| | | |
|---|---|---|
| CA | 2187921 | 11/1995 |
| EP | 0099758 | 10/1984 |

(Continued)

OTHER PUBLICATIONS

Majithia V, et al. Am. J. Med. (2007) 120 (11): 936-9.
Eichman et al. (2000) Pharm. Sci. Technolo. Today 3:232-245.
Lou et al. (2002) Macromol. 35:3456-3462.
Kobayashi et al. (2003) Bioconj. Chem. 14:388-394.
Wang, et al., "Synthesis and Application of Carbohydrate-Containing Polymers", Chem. Mater. (2002) 14, pp. 3232-3244.
Wangler, C., et al., "Antibody-dendrimer conjugates: the number, not the size of the dendrimers, determines the immunoreactivity," Bioconjug Chem., Apr. 2008, vol. 19(4), pp. 813-820.
Dirks, A. (Ton) J., et al., "Monitoring Protein—Polymer Conugation by a Fluorogenic (Cu(I)-Catalyzed Azide—Alkyne 1,3-Dipolar Cycloaddition," Bioconjugate Chemistry, vol. 20, No. 6, pp. 1129-1138 (Jun. 2009).

(Continued)

*Primary Examiner* — Jason M Nolan
(74) *Attorney, Agent, or Firm* — Casimir Jones SC

(57) ABSTRACT

The present invention relates to novel therapeutic and diagnostic dendrimers. In particular, the present invention is directed to dendrimer-linker conjugates, methods of synthesizing the same, compositions comprising the conjugates, as well as systems and methods utilizing the conjugates (e.g., in diagnostic and/or therapeutic settings (e.g., for the delivery of therapeutics, imaging, and/or targeting agents (e.g., in disease (e.g., cancer) diagnosis and/or therapy, pain therapy, etc.)). Accordingly, dendrimer-linker conjugates of the present invention may further comprise one or more components for targeting, imaging, sensing, and/or providing a therapeutic or diagnostic material and/or monitoring response to therapy.

10 Claims, 36 Drawing Sheets

U.S. PATENT DOCUMENTS

| | | |
|---|---|---|
| 5,800,391 A | 9/1998 | Kontos |
| 5,800,508 A | 9/1998 | Goicoechea |
| 5,800,519 A | 9/1998 | Sandock |
| 5,808,005 A | 9/1998 | Codington |
| 5,843,089 A | 12/1998 | Sahatjian |
| 5,851,228 A | 12/1998 | Pinheiro |
| 5,855,866 A | 1/1999 | Thorpe |
| 5,855,881 A | 1/1999 | Loike |
| 5,857,998 A | 1/1999 | Barry |
| 5,861,319 A | 1/1999 | Lin |
| 5,866,561 A | 2/1999 | Ungs |
| 5,868,719 A | 2/1999 | Tsukernik |
| 5,876,445 A | 3/1999 | Andersen |
| 5,892,019 A | 4/1999 | Schlom |
| 5,892,020 A | 4/1999 | Mezes |
| 5,898,005 A | 4/1999 | Singh |
| 5,902,863 A | 5/1999 | Dvornic |
| 5,908,413 A | 6/1999 | Lange |
| 5,913,894 A | 6/1999 | Schmitt |
| 5,922,887 A | 7/1999 | Dondio |
| 5,933,145 A | 8/1999 | Meek |
| 5,935,114 A | 8/1999 | Jang |
| 6,051,429 A | 4/2000 | Hawley-Nelson |
| 6,267,987 B1 | 7/2001 | Park |
| 6,312,679 B1 | 11/2001 | Tomalia et al. |
| 6,471,968 B1 | 10/2002 | Baker |
| 6,485,718 B1 | 11/2002 | Parthasarathy |
| 6,585,956 B2 | 7/2003 | Malik et al. |
| 6,869,772 B2 | 3/2005 | Lichtman |
| 7,078,461 B2 | 7/2006 | Tomalia |
| 7,097,856 B2 | 8/2006 | Frechet |
| 7,208,486 B2 | 4/2007 | Burnett |
| 7,261,875 B2 | 8/2007 | Li |
| 7,368,512 B2 | 5/2008 | Newkome |
| 7,419,686 B2 | 9/2008 | Kaiko et al. |
| 7,459,145 B2 | 12/2008 | Bao |
| 7,572,459 B2 | 8/2009 | Matthews |
| 7,745,229 B2 | 6/2010 | Wang |
| 2001/0031498 A1 | 10/2001 | Leclercq |
| 2002/0165179 A1 | 11/2002 | Baker, Jr. |
| 2003/0180250 A1 | 9/2003 | Chauhan et al. |
| 2004/0109842 A1 | 6/2004 | Baker, Jr. |
| 2004/0120979 A1 | 6/2004 | Roessler |
| 2005/0214247 A1 | 9/2005 | Shaunak |
| 2006/0057211 A1 | 3/2006 | Chorny |
| 2007/0020620 A1 | 1/2007 | Finn |
| 2007/0041934 A1 | 2/2007 | Williams |
| 2007/0298006 A1 | 12/2007 | Tomalia |
| 2008/0045689 A1 | 2/2008 | Stumbe et al. |
| 2008/0171067 A1 | 7/2008 | Govindan et al. |
| 2008/0200562 A1 | 8/2008 | Yin |
| 2008/0312344 A1 | 12/2008 | Liskamp |
| 2009/0012035 A1 | 1/2009 | Jacobson |
| 2009/0053139 A1 | 2/2009 | Shi |
| 2009/0069561 A1 | 3/2009 | Fokin et al. |
| 2009/0082537 A1 | 3/2009 | Ramon Hernandez et al. |
| 2009/0088376 A1 | 4/2009 | Baker, Jr. |
| 2009/0104119 A1 | 4/2009 | Majoros |
| 2009/0208580 A1 | 8/2009 | Shi |
| 2009/0287005 A1 | 11/2009 | Baker, Jr. |
| 2010/0136614 A1 | 6/2010 | Luo et al. |
| 2010/0158850 A1 | 6/2010 | Baker, Jr. |
| 2010/0160299 A1 | 6/2010 | Baker, Jr. |

FOREIGN PATENT DOCUMENTS

| | | |
|---|---|---|
| EP | 0271180 | 6/1988 |
| JP | 2002-265495 | 9/2002 |
| WO | 88/01178 | 2/1988 |
| WO | 88/01180 | 2/1988 |
| WO | WO9002545 | 3/1990 |
| WO | 95/24221 | 9/1995 |
| WO | 95/28641 | 10/1995 |
| WO | 97/07398 | 2/1997 |
| WO | 97/38134 | 10/1997 |
| WO | 98/33941 | 8/1998 |
| WO | 99/02651 | 1/1999 |
| WO | 99/07724 | 2/1999 |
| WO | 99/61662 | 2/1999 |
| WO | 99/10362 | 3/1999 |
| WO | 99/58656 | 11/1999 |
| WO | 00/16807 | 3/2000 |
| WO | 01/02861 | 11/2001 |
| WO | 01/87348 | 11/2001 |
| WO | 03/003975 | 1/2003 |
| WO | 03/011115 | 2/2003 |
| WO | 03/055935 | 7/2003 |
| WO | 2006/033766 | 3/2006 |
| WO | 2007/012001 | 1/2007 |
| WO | 2007/034750 | 3/2007 |
| WO | 2007/080114 | 7/2007 |
| WO | 2008/008483 | 1/2008 |
| WO | 2011002852 | 1/2011 |
| WO | 2011028334 | 3/2011 |
| WO | 2011/059609 | 5/2011 |
| WO | 2011053618 | 5/2011 |

OTHER PUBLICATIONS

Lalwani, Sanjiv, et al., "Mimicking PAMAM Dendrimers with Amphoteric, Hybrid Triazine Dendrimers: A Comparison of Dispersity and Stability," Macromolecules, vol. 42, No. 17, pp. 6723-6732 (Aug. 12, 2009).

Rheumatoid arthiritis, Merck Manual Home Ed. Avaialble at http://wwww.merckmanuals.com/home/print/sec05/ch066/ch066b.html (printed Apr. 19, 2011).

Wu, P., et al., Angewandte Chemie-International Edition (2004) 43 (30) pp. 3928-3932.

Rostovtsev, V.V., et al., Angewandte Chemie-Inernational Edition (2002) 41 (14), p. 2596.

Choi, Y., et al., Chem. Biol. 12(1) (2005), pp. 35-43.

Demattie, C.R., et al., Nano Letters 4(5) (2004), pp. 771-777.

Choi, Y.S., et al., Nano Letter 4(3) (2004), pp. 391-397.

Yoon, K., Org. Letter 9(11) (2007), pp. 2051-2054.

Goyal, P., Chem. Eur. J. 13 (2007), pp. 8801-8810.

Wu, P., Chem. Commun. (46) (2005), pp. 5775-5777.

Lee, J.W., Macromolecules 39(6) (2006), pp. 2418-2422.

Thomas, Thommey, et al., "Detection and Analysis of Tumor Fluorescence Using a Two-Photon Optical Fiber Probe," Biophysical Journal, vol. 86, Jun. 2004, pp. 3959-3965.

Kolb, et al. (2001) Angewandte Chemie Intl. Ed. 40:2004-2011.

Evans (2007) Australian J. Chem. 60:384-395.

Carlmark, et al. (2009) Chem. Soc. Rev. 38:352-362.

Allen, T.M., Nature Reviews Cancer (2002) 2, (1), pp. 750-763.

Peer, D., et al., Nature Nanotechnology (2007), 2, pp. 751-760.

Hong, S., et al., Chemistry & Biology (2007), 14 (1), pp. 105-113.

Mammen, M., et al., Angewandte Chemie-International Edition (1998), 37 (20), pp. 2755-2794.

Hong, S.P., et al., Bioconjugate Chmistry (2004) 15, (4), pp. 774-782.

Svenson, S., et al., Advanced Drug Delivery Reviews (2005), 57 (15), pp. 2106-2129.

Hong, S.P., et al., Bioconjugate Chmistry (2006) 17(3), pp. 728-734.

Leroueil, P.R., Am. Chem. Res. 40(5) (2007) pp. 335-342.

Thomas, T.P., et al., Biomacromoledules (2004) 5, (6) pp. 2269-2274.

Shukla, R., et al., Bioconjugate Chemistry (2006), 17 (5), pp. 1109-1115.

Wu, G., et al., Molecular Cancer Therapeutics (2006) 5(1) pp. 52-59.

Wu, G., et al., Bioconjugate Chemistry (2004) 15(1), pp. 185-194.

Backer, M.V., et al., Molecular Cancer Therapeutics (2005) 4(9), pp. 1423-1429.

Shukla, R., et al., Chemical Communications (2005) 46, pp. 5739-5741.

Sheng, K.C., et al., European Journal of Immunology (2008), 38, pp. 424-436.

Baek, M.G., et al., Bioorganic & Medicinal Chemistry (2002) 10 (1) pp. 11-17.

Taite, L.J, et al., Journal of Biomaterials Science-Polymer Edition (2006) 17(10), pp. 1159-1172.

Kono, K., et al., Bioconjugate Chemistry (1999) 10(6), pp. 1115-1121.

Shukla, S., et al., Bioconjugate Chemistry (2003) 14(1), pp. 158-167.

Thomas, t.p., et al., Journal of Medicinal Chemistry (2005), 48 (11), pp. 3729-3735.
Myc, A., et al., Anti-Cancer Drugs (2008) 19, pp. 143-149.
Majoros, I.J., et al., Journal of Medicinal Chmistry (2005) 48 (19) pp. 5892-5899.
Kukowska-Latallo, J.F., et al., Cancer Research (2005) 65(12) pp. 5317-5324.
Myc, A., et al., Biomacromolecules (2007) 8, pp. 2986-2989.
Myc, A., et al., Biomacromolcules (2007) 8 (1), pp. 13-18.
Landmark, K.J., et al., ACS Nano (2008) 2 (4), pp. 773-783.
Mullen, D.G., Bioconjug. Chem. 19(9) (2008) pp. 1748-1752.
Choi, Y., Nanostructured Supramolecular Arrays Based on Dendrimers Using DNA: Design, Synthesis and Biological Evaluation. Biomed. Eng. (NY), vol. Ph.D., Dissertation, University of Michigan, Ann Arbor, MI (2005), p. 191.
Patri, A.K., J.F. Kukowska-Latallo, and J.R. Baker, Advanced Drug Delivery Reviews (2005) 57(15), pp. 2203-2214.
Patri, A.K., I.J Majoros and J.R. Baker Jr., Current Opinion in Chemical Biology (2002) 6, pp. 466-471.
Qiu, L.Y., and Y.H. Bae, Pharmaceutical Research (2006) 23, p. 1-30.
Schcharbin, D. and B.M., Biochmica et Biophysica Acta (2006) 1760, pp. 1021-1026.
Shi, X., et al., Electrophoresis (2006) 27(9), pp. 1758-1767.
Islam, M.T., I.J., Majoros and J.R. Baker, Journal of Chromatography B-Analytical Technologies in the Biomedical and Life Sciences (2005) 822(1-2): p. 21-26).
Islam, MT., et al., Analytical Chemistry (2005) 77(7): p. 2063-2070.
Shi, X., et al., Polymer (2005) 46: p. 3022-3034.
Shi, X., et al. Colloids Surf., A., (2006), 272, pp. 139-150.
Shi, X., I.J, Majoros and J.R. Baker, Jr., Mol. Pharm (2005), 2, pp. 278-294.
Shi, X.Y., et al., Electrophoresis (2005) 26(15), pp. 2949-2959.
Shi, X.Y., et al., Analysis (2006) 131(7): p. 842-848.
Shi, X.Y., et al. Analysis (2006) 131(3), pp. 374-381.
Shi, X.Y., et al. Electrophoresis (2005) 26(15): pp. 2960-2967.
Kuracka, L., et al., Clinical Chemistry (1996) 42(5), pp. 756-760.
Orlovic, D., et al., Chromatographia (2000) 52(11/12), pp. 732-734.
Svensson, J., et al., Journal of Chromatography B: Biomedical Sciences and Applications (1982), 230(2), pp. 427-432.
Svensson, J.-O, Journal of Chromatography B., Biomedical Sciences and Applications ( )1986) 375, pp. 174-178.
Tebbett, I.R. Chromatographia 23(5), pp. 377-378, (1987).
Stamford, J.A., Journal of Neuroscience Methods, (1990), 34(1-3), pp. 67-72.
Toner, C.C., and J.A. Stamford, Journal of Neuroscience Methods (1996) 67(2), pp. 133-140.
Toner, C.D. and J.A. Stamford, Neuroscience (1997), 81(4), pp. 999-1007.
Kimiskidis, V., et al., 2007, "Development and validation of a high performance liquid chromatographic method for the determination of oxcarbazepine and its main metabolites in human plasma and cerebrospinal fluid and its application to pharmacokinetic study", J Pharm Biomed Anal.; 43(2):763-8.
Achilli, G., et al., Journal of Chromatography, A. (1996) 729(1-2), pp. 273-277.
Horner, K.A., et al., Brain Research (2004) 1028(2): pp. 121-132.
Childers, S.R. and S.R. Childers, Life Sciences (1991) 48(21): pp. 1991-2003.
Adams, J.D., Jr., et al. Biomedical Mass Spectometry (1981) 8(11): pp. 527-538.
Millhorn et al, 1996, "Regulation of ionic conductances and gene expression by hypoxia in an oxygen sensitive cell line.", Adv Exp Med Biol. 410:135-42.
Cai, Y.C., et al., "Molecular Pharmacology," (1997) 51(4), pp. 583-587.
Franklin, R,B., et al., BMC Biochemistry (2006) 7: p. 10.
Kukanich, B., et al., Therapeutic Drug Monitoring (2005) 27(3), pp. 389-392.
Cucullo, L., et al., Current Opinion in Drug Discovry & Development (2005) 8(1), pp. 88-99.
Nambiar, M.P., et al., Toxicology and Applied Pharmacology (2007) 219(2-3), pp. 142-150.

Shih, T.M., T.C. Rowland and J.H. McDonough, Journal of Pharmacology and Experimental Therapeutics (2007) 320 (1), pp. 154-161.
Schulte, H., A. Sollevi and M. Segeradahl, Pain, (2005) 116(3), pp. 366-374.
Loetsch, J., et al., Clinical Pharmacology and Therapeutics (1996) 60(3): pp. 316-325.
Hill, H.F., et al., Pain (1990) 43(1), pp. 57-79.
Worek, F., et al., Toxicology (2008). 244: pp. 35-41.
Wu, P., et al., Aldrichimica Acta 40(1) (2007), pp. 7-17.
Lee, J.W., et al., Bioconjugate Chemistry (2007) 18(2), pp. 579-584.
Lee, J.W., et al., Journal of Polymer Science Part a—Pollymer Chemistry (2008) 46, pp. 1083-1097.
Lee, J.W., et al., Tetrahedron (2006) 62(5), pp. 894-900.
Hoffman, R.E., Magn. Reson. Chem. (2006), 44, pp. 606-616.
De Groot, Franciscus, M.H., "Cascade-Release Dendrimers, Liberate All End Groups Upon a Single Triggering Event in the Dendritic Core," Angew. Chem. Int. Ed. (2003), vol. 42, pp. 4490-4494.
Lee, Cameron C., et al., "Designing Dendrimers for Biological Applications," Nature Biotechnology, Dec. 2005, vol. 23, No. 12, pp. 1517-1526.
Bloodworth, D., Phys. Med. Rehabil Clin. N. Am., (2006) 17(2), pp. 355-379.
Liu, J.K., et al., Neurobiology of Disease (2005) 1993), pp. 407-418.
Beall, H.D., et al., Journal of Medicinal Chemistry (1998) 41(24), pp. 4755-4766.
Ferrer, S., D.P. Naughton and M.D. Threadgill, Tetrahedron (2003) 59(19), pp. 3445-3454.
Naylor, M.A., et al., Journal of Medicinal Chemistry (1997) 40(15), pp. 2335-2346.
Phillips, R.M., et al., Journal of Medicinal Chemistry (1997) 40(15), pp. 2335-2346.
Phillips, R.M., et al., Journal of Medicinal Chemistry (1999) 42(20), pp. 4071-4080.
Zhang, Z., et al., Organic & Biomolecular Chemistry (2005) 3(10), pp. 1905-1910.
Damen, E.W.P., et al., Biorganic & Medicinal Chemistry (2002) 10(1), pp. 71-77.
Hay, M.P., et al., Journal of Medicinal Chemistry (2003) 46(25), pp. 5533-5545.
Hay, M.P., et al., Journal of the Chemical Society—Perkin Transactions 1 (1999 (19), pp. 2759-2770.
Daniels, T.R., et al., Clinical Immunology (2006) 121(2), pp. 144-176.
Smith, M.W., and m. Gumbleton, Journal of Drug Targeting (2006) 14(4), pp. 191-214.
Koch, 1990, Angew. Chem. Int. Ed. Engl., 29:183-5.
Tomalia, et al., Chem. Int. Ed. Engl. 29:5305 (1990).
Yin, et al., J. Am. Chem. Soc., 120:2678 (1998).
Carelli, V., et al., Bioorganic & Medicinal Chemistry Letters (2003) 13(21), pp. 3765-3769.
Christrup, L.L., et al., International Journal of Pharmaceutics (1997). 154(2): pp. 157-165.
Drustrup, J., et al., International Journal of Pharmaceutics (1991), 71(1-2), pp. 105-116.
Groth, L., et al., International Journal of Pharmaceutics (1997) 154(2), pp. 149-155.
Mignat, C., et al., Journal of Pharmaceutical Sciences (1996) 85(7), pp. 690-694.
Hay, M.P., W.R. Wilson and W.A. Denny, Tetrahedron (2000) 56(4):, pp. 645-657.
de Groot, F.M.H., E.W.P. Damen, and H.W. Scheeren, Curr. Med. Chem.—Anti-Cancer Agents (2001) 8, pp. 1093-1122.
Dubowchik, G.M., and M.A. Walker, Pharmacology & Therapeutics (1999) 83, pp. 67-123.
Papot, S., et al., 2002, "Design of selectively activated anticancer prodrugs: elimination and cyclization strategies.", Curr Med Chem Anticancer Agents.; 2(2):155-85.
De Groot, F.M.H., et al., J. Org. Chem., 2001. 66, pp. 8815-8830.
Greenwald, R.B., et al., J. Med. Chem. (1999). 42: pp. 3657-3667.
Greenwald, R.B., et al., Bioconjugate Chem. (2003) 14, pp. 395-403.
Zhang, Z., et al., Pharmaceutical Research (2005) 22, pp. 381-389.
Antczak, C., et al., Bioorg. & Med. Chem (2001), 9: pp. 2843-2848.

Pohl, T., and H. Waldmann, J. Am. Chem. Soc. (1997), 119, pp. 6702-6710.
Sauerbrei, B., V. Jungmann, and H. Waldmann, Angew. Chem. Int. Ed. (1998), 37: pp. 1143-1146.
Leung, L.Y. and T.A. Baillie, J. Med. Chem. (1986), 29, pp. 2396-2399.
Woolf, T., et al., J. Org. Chem. (1984) 49. pp. 3305-3310.
Nudelman, A., R.J. McCaully and S.C. Bell, J. Pharm. Sci. (1974) 63, pp. 1880-1885.
Esfand, R. and D.A. Tomalila, Drug Discovery Today (2001). 6, pp. 427-436.
Jansen, J.F.G.A., E.M.M. de Brabander van den Berg and E.W. Maijer, Science (1994). 266, pp. 1226-1229.
Kolhe, P., et al., International Journal of Pharmaceutics (2003), 259, pp. 143-160.
Man, N., et al., European Journal of Medicinal Chemistry (2006), 41, pp. 670-674.
Morgan, M.T., et al., J. Am. Chem., Soc. (2003), 125(50): pp. 15485-15489.
Papagiannaros, A., et al., International Journal of Pharmaceutics (2005), 302, pp. 29-38.
International Search Report dated Jan. 5, 2010, PCT/US2009/036992, filed Mar. 12, 2009.
Jesse B. Wolinsky and Mark W. Grinstaff, "Therapeutic and diagnostic application of dendrimers for cancer treatment," Advanced Drug Delivery Reviews, Mar. 4, 2008, vol. 60, pp. 1037-1055.
Ulrik Boas and Peter M. H. Heegaard, "Dendrimers in drug research," Chemical Society Review, 2004, vol. 33, pp. 43-63.
Istvan J. Majoros, et al., "Poly(amidoamine) dendrimer-based multifunctional engineered nanodevice for cancer therapy," Journal of Medicinal Chemistry, 2005, vol. 48, pp. 5892-5899.
Tooru Ooya, Jaehwei Lee and Kinam Park, "Hydrotropic dendrimers of generations 4 and 5: Synthesis, characterization and hydrotropic solubilization of paclitaxel," Bioconjugate Chemistry, 2004, vol. 15, pp. 1221-1229.
Anil K. Patri, et al., "Synthesis and in vitro testing of J591 antibody-dendrimer conjugates for targeted prostage cancer therapy," Bioconjugate Chemistry 2004, vol. 15, pp. 1174-1181.
Yang, Cancer Research, 1997, vol. 53, pp. 4333-4339.
Mojoros et al., Macromolecules, 2003, vol. 36, pp. 5526-5529.
Wu et al., Anti-Cancer Agents in Medicinal Chemistry, Mar. 2006, vol. 6, pp. 167-184.
Suzawa, et al., "Synthesis of a Novel Duocarmycin Derivative DU-257 . . . ", Bioorganic & Medicinal Chemistry 8 (2000) 2175-2184.
Tang et al., "In Vivo Gene Delivery by Degraded Polyamidoamine Dendrimers," Biocong Chem 7:703 (1996).
Tjandra et al., "Application of mammary serum antigen assay in the management of breast cancer: a preliminary report," Br. J. Surg. 75:811-817 (1988).
Tomalia et al., "Starburst Dendrimers: Molecular-Level Control of Size, Shape, Surface chemistry, Topology, and Flexibility from Atoms to Macroscopic Matter," Chem. Int. Ed. Engl., 29:138-175(1990).
Tomalia et al., "Comb-Burst Dendrimer Topology. New Macromolecular Architecture Derived from Dendritic Grating,"Macromolecule 24:1435-1438 (1999).
Tomalia, "Starburst/Cascade Dendrimers: Fundamental Building Blocks for a New Nanoscopic Chemistry Set," Advanced Materials 6:529 (1994).
Tortora et al., "Synergistic Inhibition of Growth and Induction of Apoptosis by 8-Chloro-cAMP and Paclitaxel or Cisplatin in Human Cancer Cells," Cancer Research 57:5107 (1997).
Trainer, et al., "Gene delivery to the epidermis," Human Mol. Gen 6:1761 (1997).
Tuerk et al., "In vitro evolution of functional nucleic acids: high-affinity FNA ligands of HIV-1 proteins," Gene 137 (1):33-9 (1993).
Uppuluri et al., Tecto(Dendrimer) Core-Shell Molecules: . . . PMSE 80:55 (1999).
Urdea and Horn, "Dendrimer Development," Science 261:534 (1993).

Van Hest et al., "Polystyrene-Dendrimer Amphiphilic Block Copolymers with a Generation-Dependent Aggregation," Science 268:1592-1595 (1995).
Vasey et al., "Phase I Cliniclal and Pharmacokinetic Study of PK1 . . . ", Clin. Cancer Res. 5:83 (1999).
Wagner, "Effects of membrane-active agents in gene delivery," Journal of controlled Release 53:155-158 (1998).
Webber et al., "Characterisation of soluble, salt-loaded, degradable PLGA films and their release of tetracycline," J. Biomed Mater Res 41:18 (1998).
White, et al., "Viral Recptors of the Immunoglobulin Superfamily," Cell 56:725 (1989).
Wiener et al., "Dendrimer-Based Metal Chelates: A New Class of Magnetic Resonance Imaging Contrast Agents," Magn Reson. Med. 31:1 (1994).
Wiener et al., "Targeting Dendrimer-Chelates to Tumors and Tumor Cells Expressing the High-Affinity Folate Receptor," Invest. Radiol. 32:748 (1997).
Wies, et al., "Structure of the influenza virus haemagglutinin complexed with its recptor, sialic acid," Nature 333:426 (1988).
Wilbur et al., "Biotin Reagents for Antibody Pretargeting . . . " Bioconjugate Chem., 9:813 (1998).
Winter, "Formation of the Scab and the Rate of Epithelization of Superficial Wounds in the Skin of the Young Domestic Pig," Nature 193:293 (1962).
Wong et al., "Accuracy and Precision of In Vitro Volumetric Measurements by Three-Dimensional Sonography," Ivest. Rad.31:26 (1996).
Wu et al., "Metal-Chelate-Dendrimer-Antibody Constructs for Use in Radioimmunotherapy and Imaging," Bioorg. Med. Chem. Lett., 4:449 (1994).
Wyrick et al., "Entry of Genital Chlamydia trachomatis into Polarized Human Epithelial Cells," Infect. Imm. 57:2378 (1989).
Ye, et al., "Targeted gene correction: a new strategy for molecular medicine" Mol. Med. Today 4:431 (1998).
Yew et al., "Optimization of Plasmid Vectors for High-Level Expression in Lung Epithelial Cells," Human Gene Ther. 8:575 (1997).
Yin et al., "Architectural Copolymers: Rod-Shaped, Cylindrical Dendrimers," J. Am. Chem. Soc., 120:2678 (1998).
Yu, et al., "Overexpression of ErbB2 blocks Taxol-Induced Apoptosis by Upregulation of p21(cip1), which Inhibits p34 (Cdc2) Kinase," Molecular Cell, 2:581 (1998).
Zaffaroni et al., "Induction of apoptosis by taxol and cisplatin and effect on cell cycle-related proteins in cisplatin-sensitive and resistance human ovarian cancer cells," Brit. J. Cancer 77:1378 (1998).
Zhuo et al. 1999, In vitro release of 5-fluorouracil with cyclic core dendritic polymer, J. of Controlled Release 57:249-257.
Zimmerman et al., "Self-Assembling Dendrimers," Science 271:1095-1098 (1996).
Abel et al., "The Selective Concentration of Sulpha-diazine and Related Compounds in Malignant Tissue," Eur. J. Cancer 9:4 (1973).
Abrams, et al., "Programmed cell death during *Drosophila embryogenesis*," Development 117:29 (1993).
Wong et al., ."Accuracy and Precision of In Vitro Volumetric Measurements by Three-Dimensional Sonography," Ivest. Rad. 31:26 (1996).
Adlish et al., "Identification of a Putative Cell Receptor for Human Cytomegalovirus," Virology 176:337 (1990).
Akutsu et al., "Schedule-dependent Interaction Between Paclitaxel and Doxorubicin in Human Cancer Cell Lines in Vitro," Eur. J. Cancer 31A:2341 (1995).
Australian First Report on Application No. 2005287375 dated Jun. 10, 2008.
Babiuk, Shawn, Foldvari, Marianna, et al., "Cutaneous vaccination: the skin as an immunologically active tissue and the challenge of antigen delivery," Journal of Controlled Release, vol. 66 Issues 2-3, May 15, 2000 pp. 199.
Baker et al., "The Synthesis and Testing of Anti-Cancer Therapeutic Nanodevices," Kluwer Academic Publishers, Manufactured in the Netherlands 61-690 (2001).
Baldwin and Saltzman et al., "Materials for protein delivery in tissue engineering" 1998 Advanced Drug Delivery Reviews vol. 33, pp. 71-86.

Balogh and Tomalia, J. Am. Che. Soc. 120:7355 (1998).
Balogh et al., "Formation and Characterization of Dendrimer-Based Water Soluble Inorganic Nanocomposites," Proc. of ACS PMSE 77:118 (1997).
Banga et al., "Assessing the potential of skin electroporation for the delivery of protein- and gene-based drugs," Trends in Biotechnology vol. 16 Issue 10, Oct. 1, 1998 pp. 408-412.
Banker et al., "Utilization of Lipophilic Ionic Additives in Liquid Polymer Film Optodes for Selective Anion Activity Measurements," Anal. Chem. 69:990 (1997).
Barth et al., "Boron Neutron Capture Therapy of Brain Tumors: Past History, Current Status, and Future Potential," Cancer Invetigation 14:534 (1996).
Barth, et al., "Boronated Starburst Dendrimer-Monoclonal Antibody Immunoconjugates: Evaluation as a Potential Delivery System for Neutron Capture therapy," Bioconjugate Chem. 5:58 (1994).
Baumann et al., "Simultaneous Visualization of the Yellow and Green Forms of the Green Fluorescent Protein in Lving Cells," J. Histochem. Cytochem. 46:1073 (1998).
Bell, "Molecular Trees: A New Branch of Chemistry," Science 271:1077-1078 (1996).
Bielinska et al., "Regulation of in vitro gene expression using antisense oligonucleotides . . . " Nucleic Acids res 24:2176 (1996).
Bielinska et al., "The interaction of plasmid DNA with polyamidoamine dendrimers: . . . " Biochimica et Biophysica Acta 1353:180-190 (1997).
Bielinska et al. Bioconj Chem 10:843-850 (1999).
Bielinska et al., "Application of membrane-based dendrimer/DNA complexes for solid phase transfection in vitro and in vivo" May 2000 Biomaterials vol. 21, Issue 9, pp. 877-887.
Binkley et al., "FNA ligands to human nerve growth factor," Nuc. Acids Res. 23(16):3198-205 (1995).
Block, Lawrence, "Medicated Applications", Remington's Pharmaceutical Sciences, edited by Gennaro, 1990, 18th Edition, pp. 1596 and 1597.
Botchway, et al., "Novel Visible and Ultraviolet Light Photogeneration of . . . " Photochem., Photobiol. 67(7):635-40 (1998).
Bourassa et al., "Photochemistry of Roussin's Red Salt . . . " JACS 119:2853-60 (1997).
Bourne, et al., "Evaluation of the Effects of Intravascular MR Contrast Media (Gadolinium Dendrimer) on 3D Time of Flight Magnetic Resonance Angiography of the Body,"J. Magn. Reson. Imag., 6:305 (1996).
Brandl et al., "Plastics from Bacteria and for Bacteria: . . . ", Adv. Biochem Eng Biotechnol, 41:77 (1990).
Brasseur et al., "Biological Activities of Phthalocyanines . . . " Photochem., Photobiol., 47:705-11 (1988).
Braunegg et al., "Polyhydroxyalkanoates, biopolyesters from renewable resources: Physiological and engineering aspects,"J. Biotechnol 65(2-3):127 (1998).
Brazeau et al., "In vitro myotoxicity of selected cationic macromolecules used in non-viral gene delivery," Pharm Research 15:680-684 (1998).
Capala et al., "Boronated Epidermal Growth Factor as a Potential Targeting Agent for Boron Neutron Capture Therapy of Brain Tumors," Bioconjugate Chem., 7:7 (1996).
Carel et al., "Structural Requirements for C3d,g/Epstein-Barr Virus Receptor (CR2/CD21) Ligand Binding, Internalization, and Viral Infection," J. Biol. Chem. 265:12293 (1990).
Chan and Nie, "quantum Dot Bioconjugates for Ultrasensitive Nonisotopic Detection," Science 281:2016 (1998).
Chang, et al., "Synthetic Appropaches to Long-Wavelength Absorbing Photosensitizers: Porphyrinone and Derivatives," Proc. SPIE, 1203:281-86 (1990).
Chinese Office Action dated Jan. 16, 2009, CN Patent Application No. 200580034777.9.
Choate et al., "Direct Cutaneous Gene Delivery in Human Genetic Skin Disease," Human Gene Ther 8:1659 (1997).
Choi et al., "Poly(ethylene glycol)-block-poly(L-lysine) Dendrimer . . . ", Bioconjugate Chem. 10:62-65 (1999).
Cincotta, et al., "Novel Benzophenothiazinium Photosensitizers: Preliminary In-Vivo Results," SPIE Proc. SPIE 1203:202-10 (1990).

Co et al., "Isolation and biochemical characterization of the mammalian reovirus type 3 cell-surface receptor," Proc Natl. Acad. Sci 82:1494 (1985).
Cohen and Tohoku, Exp. Med. 168:351 (1992), Abstract printed on May 1, 2002 (1 page).
Cole et al., "The EBV-Hybridoma Technique and its Application to Human Lung Cancer," in Monoclonal Antibodies and Cancer Therapy, Alan R. Liss, Inc., pp. 77-96 (1985).
Cortese et al., "Identification of biologically active peptides using random libraries displayed on phage," Curr. Opin. Biotechol., 6:73 (1995).
Cote et al., "Generation of human monoclonal antibodies reactive with cellular antigens," Proc. Natl. Acad. Sci. U.S.A. 80:2026-2030 (1983).
Davies, "Synthetic materials for covering burn woulds: Progress towards perfection. Part I. Short term dressing materials," Burns 10:94 (1983).
De Leo and Ford, "Reversible Photolabilzation of NO from Chromium (III)-Coordinated Nitrite. A New Strategy for Nitric Oxide Delivery," JACS 121:1980-81 (1999).
Duncan and Malik, Control Rel. Bioact. Mater. 23:105 (1996).
Duncan and Sat, "Tumour targeting by enhanced permeability and retention (EPR) effect," Ann. Oncol. 9:39 (1998).
Duncan et al., "Polymer Conjugates for Anti-Cancer Agent and DNA Delivery," Polymer Preprints 39:180 (1998).
Dvornic and Tomalia, "Dendritic polymers divergent synthesis: starburst poly(amidoamine) dendrimers," in Salamone (ed.) The Polymeric Materials Encyclopedia: Synthesis, Proper, (1996).
EP Patent Application No. EP 01 935 316.8, Office Action dated Nov. 30, 2007.
Lester et al., "Infrared Microspectroscopic Imaging of the Cerebellum of Normal and Cytarabine Treated Rats," Cell Mol. Biol. 44:29 (1998).
Levi-Montalcini, "The Nerve Growth Factor Thirty-Five Years Later," In Vitro Cell., Devi. Biol. 23:227 (1987).
Liao, et al., "Chromophore-assisted laser inactivation of proteins is mediated by the photogeneration of free radicals," PNAS 91:2659 (1994).
Luck et al., "Plasma protein adsorption on biodegradable microspheres . . . " J. Control. Rel 55:107 (1998).
Madihally and Matthew, "Porous chitosan scaffolds for tissue engineering," Biomaterials 20(12):1133 (1999).
Majoros and Tomalia, Mar. 18, 2006 Abstract Only printed Apr. 20, 2009, "Synthesis and Characterization of Novel POPAM-PAMAM (POMAM) Hybrid Dendrimers as Reactive Modules for Nanodevice Construction" Eight Foresight Conference on Molecular Nanotechnology.
Majoros et al., "PAMAM Dendrimer-based multifunctional conjugate for cancer therapy: synthesis, characterization and functionality," Biomacromolecules, 2006, vol. 7, pp. 572-579.
Majoros, et al., "Acetylation of Poly(amidoamine) Dendrimers," Macromolecules 2003, 36, 5526-5529.
Malik et al., "A PAMAM Dendrimer-Platinate," Proc. Int'l Symp. Control. Rel. Bioact. Mater, 24:107 (1997).
Malik et al., "Dendrimers: Relationshipo between structure and biocompatibility in vitro, and preliminary studies on the biodistribution of (125)I-labelled polyamidoamine dendrimers in vivo," Journal of Controlled Relief 65:133-148 (2000).
Marlin et al., "A soluble form of intercellular adhesion molecule-1 inhibits rhinovirus infection," Nature 344:70 (1990).
Mayer et al., "Matrices for tissue engineering-scaffold structure for a bioartificial liver support system," J. Controlled Release 64(1-3):81 (2000).
Mendelsohn et al., "Cellular Receptor for Poliovirus: Molecular Cloning, . . . " Cell 56:855 (1989).
Monsigny et al., "Characterization and biological implications of membrane lectins in tumor, lymphoid and myeloid cells," Biochemie 70:1633 (1988).
Mosmann, "Rapid Colorimetric Assay for Cellular Growth and Survival: Application to Proliferation and Cytotoxity Assays," J. Immunol. Meth, 65:55 (1983).

Murphy, et al., "Photolytic Release of Nitric Oxide Modulates NMDA Receptor-mediated Transmission but Does not Induce Long-term Potentiation at Hippocampal Synapses," Neuropharm. 33:1375-85 (1994).

Naylor et al., Starburst Dendrimers. 5. Molecular Shape Control, J. Am. Chem. Soc. 111:2339-2341 (1989).

Niemiec et al., "Perifollicular Transgenic Expression of Human Interleukin-1 Rectpro Antagonist Protein following Topical Application of Novel Liposome-Plasmid DNA Formulations In Vivo," J. Pharm Sci. 86:701 (1997).

Orentas et al., "Detection of Epstein-Barr virus EBER sequence in post-transplant lymphoma patients with DNA dendrimers," Journal of Virological Methods 77:153-163 (1999).

Ottl, et al., "Preparation and Photoactivation of Caged Fluorophores and Caged Proteins Using a New Class of Heterobifunctional, Photocleavable Cross-Linking Reagents," Bioconjugate Chem. 9:143 (1998).

Page and Roy, "Synthesis and Biological Properties of Mannosylated Starburst Poly(amidoamine) Dendrimers," Bioconjugate Chem., 8:714 (1997).

Pan, et al., "Dendrimer modified magnetite nanoparticles for protein immobilization," Journal of Colloid and Interface Science, 2005, vol. 284, pp. 1-6.

Pandey, et al., "Chlorin and Porphyrine Derivatives as Potential Photosensitizers in Photodynamic Therapy," Photochem., Photobiol., 53:65-72 (1991).

Park et al., "Anti-HER2 immunoliposomes for targeted therapy of human tumors," Cancer Lett., 118:153 (1997).

Pasani et al., "Antitumor Complexes of Platinum with Carrier Molecules," Inorg. Chim. Acta 80:99 (1983).

Pavlova et al., "Biocompatible and biodegradable polyurethane polymers," Biomaterials 14(13):1024 (1993).

Pegrarn et al., Proc. Am. Soc. Clin. Oncol. 14:106 (1995).

Penault-Llorca et al., "Expression of FGF and FGF Receptor Genes in Human Breast Cancer," Int. J. Cancer 61:170 (1995).

Pillai V.N.R., "Photoremovable Protecting Groups in Organic Synthesis," Synthesis: 1-26 (1980).

Press et al., "Expression of the HER-2/neu proto-oncogene in normal human adult and fetal tissues," Oncogene 5:953 (1990).

Quintana, et al., "Design and Function of a Dendrimer-Based Therapeutic Nanodevice Targeted to Tumor Cells Through the Folate Receptor," Pharmaceutical Research, vol. 19, No. 9, Sep. 2002.

Raczka et al., "The effect of synthetic surfactant Exosurf on gene transfer in mouse lung in vivo," Gene Ther 5:1333 (1998).

Riley, "Wound Healing," Am Fam. Physician 24:107 (1981).

Rinberg "Pnuematic capillary gun for ballistic delivery of microparticles" 2005 Applied Physics Letters vol. 87 pp. 1-3.

Roberts, et al., "Preliminary biological evaluation of oplyamidoamine (PAMAM) Starburst dendrimers," J. Biomed Mater res 30:53 (1996).

Roessler et al., "Substituted β-Cyclodextrins Interact with PAMAM Dendrimer-DNA Complexes and Modify Transfection Efficiency," Biochem. 124-129 (2001).

Ruff, et al., "CD4 receptor binding peptides that block HIV infectivity cause human monocyte chemotaxis," FEBS Letters 211:17 (1987).

Ruponen et al., "Interactions of polymeric and liposomal gene delivery systems with extracellular glycosaminoglycans: physicochemical and transfection studies," Biochmica ET Biophysica Acta 1415:331-341 (1999).

Sacerdote et al., "Vasoactive Intestinal Peptide 1-12: . . . " J. of Neuroscience Research 18:102 (1987).

Segura and Shea, "Materials for Non-Viral Gene Delivery" 2001 Annual Review of Materials Research, vol. 31 pp. 25-46.

Selman et al., "Copper Benzochlorin, a Novel Photosensitizer for Photodynamic Therapy . . . " Photochem. Photobio, 57:681-85 (1993).

Sessler et al., "Tripyrroledimethine-derived ("texaphyrine"-type) . . . " Proc. SPIE, 1426:318-29 (1991).

Shchepinov et al., "Oligonucleotide dendrimers: synthesis and use as polylabelled DNA probes," Nucleic Acids Research 25:4447-4454 (1997).

Shea, "DNA delivery from polymer matrices for tissue engineering," Jun. 1999, Nature Biotechnology.

Shephey et al., "Monoclonal antibody identificaiton ofa 100-kDa membrane protein in HeLa cells and human spinal cord involved in poliovirus attachment," Proc. Natl. Acad. Sci. 85:7743 (1988).

Shortreed, et al., "Directed Energy Transfer Funnels in Dendrimetric Antenna Supermolecules," J. Phys. Chem. 101-6318 (1997).

Singh et al., "Starburst Dendrimers: Enhanced Performance and Flexibility for Immunoassays," Clin. Chem. 40:1845 (1994).

Sottosanti, "Calcium Sulfate: A Biodegradable and Biocompatible Barrier for Guided Tissue Regeneration," Compendium 13(3):226-8, 230, 232-4 (1992).

Springer et al., "Blood Group Tn-Active Macromolecules from Human . . . " Carbohydr. Res. 178:271-292 (1988).

Talanian et al., "Substrate Specificities of Caspase Family Proteases," J. Biol. Chem., 272:9677 (1997).

Eppstein et al., "Epidermal growth factor receptor occupancy inhibits vaccinia virus infection," Nature 318:663 (1985).

Esfand et al., "synthesis, Complexation and Pharmaceutical Applications of Tetra-directional Cascade Dendrimers," Pharm Sci., 2:157 (1996).

Farkas et al., "Microscopic and Mesoscopic Spectral Bio-Imaging," SPEI 2678:200 (1997).

Fidler et al., "The Implications of Angiogenesis for the Biology and Therapy of Cancer Metastatis," Cell, 79:185 (1994).

Firey and Rodgers, "Photo-Properties of a Silicon Naphthalocyanine: . . . " Photochem. Photobiol., 45:535-38 (1997).

Folkman et al., "Antiogenesis," Journ. of Biol. Chem. 267(16):10931 (1992).

Folkman et al., "Angiogenic Factors," Science, 235:442 (1987).

Folkman, "Clinical Applications of Research on Angiogenesis," New Eng. J. Med. 333(26):1757 (1995).

Fracasso, et al., "Anti-tumor effects of toxins targeted to the prostate specific membrane antigen," The Prostate, 2002, 53: 9-23.

Frechet, et al., "Self-Condensing Vinyl Polymerization: An Approach to Dendritic Materials," Science 269:1080-1083 (1995).

Frechet, "Functional Polymers and Dendrimers: Reactivity, Molecular Architechture, and Interfacial Energy," Science 263:1710-1715 (1994).

Friedman, "Gene Therapy of Cancer Through Restoration of Tumor-Suppressor Functions?J" Cancer 70:1810 (1992).

Fujiwara et al., "Therapeutic Effect of a Retroviral Wild-Type p53 Expression Vector in an Orthotopic Lung Cancer Model," J. Natl. Cancer Inst., 86:458 (1994).

Gac et al., "Synthesis, Characterisation and In Vivo Behaviour of a Norfloxacin-Poly(L-Lysine Citramide Imide) Conjugate Beraing Mannosyl Residues," J. Drug Target 7(5):393 (2000).

Garcia-Contreras et al., "Biodegradable Cisplatin Microspheres for Direct Brain Injection: Preparation and Characterization," Pharm Dev Tech 2:53 (1997).

Gerwitz et al., "Nucleic Acid Therapeutics: State of the Art and Future Prospects," Blood 92:712 (1998).

Gibb, "Apoptosis as a Measure of Chemosensitivity to Cisplatin and Taxol Therapy in Ovarian Cancer Cell Lines," Gynecologoic Oncology 65:13 (1997).

Goodwin and Meares, Cancer (suppl.) 80:2675 (1997).

Haensler et al., "Polyamidoamine Cascade Polymers Mediate Efficient Transfection of Cells in Culture," Bioconjugate Chem. 4:373-379 (1993).

Hanisch et al., "Structural Studies on Oncofetal Carbohydrate . . . " Carbohydr. Res. 178:29-47 (1988).

Hawker et al., "Unimolecular Micelles and Globular Amphiphiles: Dendritic Macromolecules as Novel Recyclable Solubilization Agents," J. Chem. Soc. Perkins Trans. 12:1287-1297 (1993).

Hinoda et al., "Immunochemical Characterization of Adenocarcinoma-Associated Antigen YH206," Cancer J. 42:653-658 (1988).

Hockenbery et al., "Bcl-2 Functions in an Antioxidant Pathway to Prevent Apoptosis," Cell 75:241 (1993).

Holister et al., "Dendrimers" 2003 Technology White Papers pp. 1-15.

Huse, et al., "Generation of a Large Combinatorial Library of the Immunoglobulin Repertoire in Phage Lambda," Science 246:1275-1281 (1989).

International Search Report mailed Sep. 8, 2008, PCT/US2007/15976.

International Search Report dated Jul. 8, 2002, PCT/US01/15204.

International Search Report dated Nov. 20, 2001, PCT/US01/40824.

International Search Report mailed Jul. 17, 2006, PCT/US05/30278.

International Search Report PCT/US2001/15204 mailed Jul. 8, 2002.

International Search Report, PCT/Us2008/061023, dated Dec. 16, 2008.

Ishida et al., "Related Glycoproteins from Normal Secretory and Malignant Breast Cells," Tumor Biol. 10:12-22 (1989).

Jain et al., "Controlled Drug Delivery by Biodegradable Poly(Ester) Devices: Different Preparative Approaches," Drug Dev Ind Pharm 24:703 (1998).

Jane et al., "Vector development: a major obstacle in human gene therapy," Annals of Med 30:413 (1998).

Jansen et al., "The Dendritic Box: Shape-Selective Liberation of Encapsulated Guests," J. Am. Chem. Soc. 117:4417-4418 1995.

Jellinek, et al., "Inhibition of Receptor Binding by High-Affinity RNA Ligands to Vascular Endothelial Growth Factor," Biochem 83(34):10450-6 (1994).

Kaner et al., "Fibroblast Growth Factor Receptor is a Portal of Cellular Entry for Herpes Simplex Virus Type 1," Science 248:1410 (1990).

Kannon and Garrett, "Moist Wound Healing with Occlusive Dressings," Ermatol. Surg. 21:583 (1995).

Kerr et al., "Apoptosis: Its Significance in Cancer and Cancer Therapy," Cancer 73:2013 (1994).

Klatzman et al., "T-lymphocyte T4 molecule behaves as the receptor for human retrovirus LAV," Nature 312:767 (1984).

Kirpotin et al., "Sterically Stabilized Anti-HER2 Immunoliposomes: Design and Targeting to Human Breast Cancer Cells in Vitro," Biochem., 36:66 (1997).

Kjeldsen et al., "Preparation and Characterization of Monoclonal Antibodies Directed to the Tumor-associated O-linked . . . " Cancer Res. 48:2214-2220 (1988).

Kohler and Milstein, "Continuous cultures of fused cells secreting antibody of predefined specificity," Nature 256:495-497 (1975).

Kozbor et al. "The production of monoclonal antibodies from human lymphocytes," Immunol. Today 4:72 (1983).

Krah, "Characterization of Octyl Glucoside-Solubilized Cell Membrane Receptors for Binding Measles Virus," Virology 172:386 (1989).

Kuhlmann et al., "Reduction o cisplatin toxitiy in cultured renal tubular cells by the bioflavonoid quercetin," Arch. Toxicol. 72:536 (1998).

Kukowska-Latallo et al., "Efficient transfer of genetic material into mammalian cells using Starburst polyamidoamine dendrimers," Proc. Natl. Acad. Sci. USA 93:4897-4902 (1996).

Lan et al., "Isolation and Properties of a Human Pancreatic Adenocarcinoma-associated . . . " Cancer Res. 45:305-310 (1985).

Lanni et al., "p53-independent apoptosis induced by paclitaxel througho an indirect mechanism," Proc. Natl. Acad. Sci., 94:9679 (1997).

Lentz, et al., "Is the Acetylcholine Rectpor a Rabies Virus Receptor," Science 215:182 (1982).

A)

B)

C)

A)

B)

C)

D)

Scheme 1. Drug releasing mechanism of the tripartite prodrug strategy

Glucuronidase
induced cleavage

Factors that affect the effectiveness of the linker

A

X = O, NH  Additional self-degradable linkers
Y = (CH$_2$)nX

B

X = O, NH  Additional self-degradable linkers
Y = (CH$_2$)nX

DENDRIMER CONJUGATES

CROSS-REFERENCE TO RELATED APPLICATIONS

The present application is a continuation of pending U.S. patent application Ser. No. 12/403,179, filed Mar. 12, 2009, which claims priority to expired U.S. Provisional Patent Application No. 61/035,949, filed Mar. 12, 2008, the contents of which are hereby incorporated by reference in their entireties.

STATEMENT REGARDING FEDERALLY SPONSORED RESEARCH OR DEVELOPMENT

This invention was made with government support under contract No. 5RO1CA119409 awarded by the National Institutes of Health. The government has certain rights in the invention.

FIELD OF THE INVENTION

The present invention relates to novel therapeutic and diagnostic dendrimers. In particular, the present invention is directed to dendrimer-linker conjugates, methods of synthesizing the same, compositions comprising the conjugates, as well as systems and methods utilizing the conjugates (e.g., in diagnostic and/or therapeutic settings (e.g., for the delivery of therapeutics, imaging, and/or targeting agents (e.g., in disease (e.g., cancer) diagnosis and/or therapy, pain therapy, etc.)). Accordingly, dendrimer-linker conjugates of the present invention may further comprise one or more components for targeting, imaging, sensing, and/or providing a therapeutic or diagnostic material and/or monitoring response to therapy.

BACKGROUND OF THE INVENTION

Cancer remains the number two cause of mortality in the United States, resulting in over 500,000 deaths per year. Despite advances in detection and treatment, cancer mortality remains high. New compositions and methods for the imaging and treatment (e.g., therapeutic) of cancer may help to reduce the rate of mortality associated with cancer.

Severe, chronic pain is observed a variety of subjects. For example, there exist large numbers of individuals with sever pain associated with arthritis, autoimmune disease, injury, cancer, and a host of other conditions.

A vast number of different types of pain medications exist. For example, a number natural and synthetic alkaloids of opium (i.e., opioids) are useful as analgesics for the treatment of severe pain. However, a number of severe side effects associated with opioid and other pain medication usage exist. For example, administration of opioid agonists often results in intestinal dysfunction due to action of the opioid agonist upon the large number of receptors in the intestinal wall. Opioids are generally known to cause nausea and vomiting as well as inhibition of normal propulsive gastrointestinal function in animals, resulting in side effects such as constipation.

Pain medication (e.g., opioid)-induced side effects are a serious problem for patients being administered pain medications (e.g., opioid analgesics) for both short term and long term pain management. For instance, more than 250,000 terminal cancer patients each year take opioids, such as morphine, for pain relief, and about half of those patients experience severe constipation. At present, patients receiving opioid pain medications face the difficult choice of suffering burdensome adverse effects (e.g., constipation) or ineffective analgesia.

There exists a need for compositions, methods and systems for delivering agents (e.g., diagnostic and/or therapeutic (e.g., cancer and/or pain therapeutics) to subjects that provide effective therapy (e.g., disease treatment, symptom relief, etc.) with reduced or eliminated side effects, even when administered in high doses.

SUMMARY

The present invention relates to novel therapeutic and diagnostic dendrimers. In particular, the present invention is directed to dendrimer-linker conjugates, methods of synthesizing the same, compositions comprising the conjugates, as well as systems and methods utilizing the conjugates (e.g., in diagnostic and/or therapeutic settings (e.g., for the delivery of therapeutics, imaging, and/or targeting agents (e.g., in disease (e.g., cancer) diagnosis and/or therapy, pain therapy, etc.)). Accordingly, dendrimer-linker conjugates of the present invention may further comprise one or more components for targeting, imaging, sensing, and/or providing a therapeutic or diagnostic material and/or monitoring response to therapy.

In particular, experiments conducted during the course of development of embodiments for the present invention demonstrated formation and use of therapeutic agents conjugated with dendrimers via a linker agent. Examples of linker agents include, but are not limited to, elimination linkers (e.g., 1,4 elimination linkers, 1,6 elimination linkers), cyclization based linkers, esterase sensitive linkers, glucoronidase sensitive linkers, hypoxia induced linkers (e.g., indolequinone), etc.

Accordingly, in certain embodiments, the present invention provides dendrimer conjugates comprising a linker, wherein said linker is conjugated to, for example, a G5 PAMAM dendrimer, a targeting agent, and a therapeutic compound. In some embodiments, the G5 PAMAM dendrimer is conjugated to an imaging agent.

The dendrimer conjugates are not limited to a particular type of linker. Examples of linker agents include, but are not limited to, elimination linkers (e.g., 1,4 elimination linkers, 1,6 elimination linkers), cyclization based linkers, esterase sensitive linkers, glucoronidase sensitive linkers, hypoxia induced linkers (e.g., indolequinone), etc. In some embodiments, the linker comprises a heteroaromatic nitrogen containing compound. In some embodiments, the linker is a branched self-elimination linker.

The dendrimer conjugates are not limited to particular therapeutic agents. In some embodiments, the therapeutic agent is Naloxone or a Naloxone pro-drug, or equivalent.

In certain embodiments, the present invention provides dendrimer conjugates comprising a G5 PAMAM dendrimer, a trigger, a linker, and a therapeutic compound. In some embodiments, the trigger is conjugated to the dendrimer and to the linker. In some embodiments, the dendrimer is conjugated to the linker that is conjugated to the trigger and to the therapeutic compound. In some embodiments, the enzyme labile bond links the trigger and the linker. In some embodiments, wherein upon cleavage of the labile bond the linkers self-degrade. In some embodiments, wherein cleavage of the linker is induced by hypoxia. In some embodiments, the linker is indolequinone.

DEFINITIONS

Figure 1:
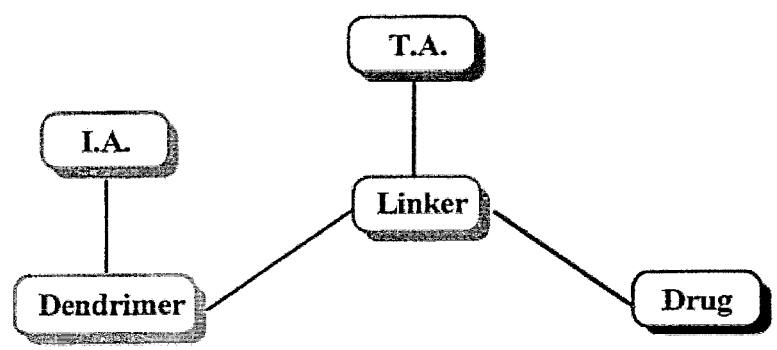
FIG. 1 shows a diagram of a dendrimer conjugate provided in some embodiments of the present invention.

To facilitate an understanding of the present invention, a number of terms and phrases are defined below:

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the terms "epithelial tissue" or "epithelium" refer to the cellular covering of internal and external surfaces of the body, including the lining of vessels and other small cavities. It consists of cells joined by small amounts of cementing substances. Epithelium is classified into types on the basis of the number of layers deep and the shape of the superficial cells.

As used herein, the term "normal epithelium of prostate" refers to prostate epithelium that does not show any detectable indication of cancerous or pre-cancerous conditions.

As used herein, the term "cancerous epithelium of prostate" refers to prostate epithelium that shows a detectable indication of cancerous or pre-cancerous conditions.

As used herein, the term "subject suspected of having cancer" refers to a subject that presents one or more symptoms indicative of a cancer (e.g., a noticeable lump or mass) or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received a preliminary diagnosis (e.g., a CT scan showing a mass) but for whom a confirmatory test (e.g., biopsy and/or histology) has not been done or for whom the stage of cancer is not known. The term further includes people who once had cancer (e.g., an individual in remission). A "subject suspected of having cancer" is sometimes diagnosed with cancer and is sometimes found to not have cancer.

As used herein, the terms "prostate specific membrane antigent" or "PSMA" refer to a membrane-bound epitope, originally identified by Horoszewicz et al. (See, e.g., Horoszewicz et al., Anticancer Res 7, 927, (1987); van Steenbrugge et al., Urol Res 17, 71 (1989); Carter et al., Proc Natl Acad Sci USA. 93(2): 749 (1996)), selectively expressed in epithelial cells of prostatic origin. Small amounts of PSMA expression have been detected in a variety of tumors (See, e.g., Chang et al., Clin Cancer Res 5, 2674 (1999)).

As used herein, the term "subject diagnosed with a cancer" refers to a subject who has been tested and found to have cancerous cells. The cancer may be diagnosed using any suitable method, including but not limited to, biopsy, x-ray, blood test, and the diagnostic methods of the present invention. A "preliminary diagnosis" is one based only on visual (e.g., CT scan or the presence of a lump) and antigen tests (e.g., PSMA).

As used herein, the term "initial diagnosis" refers to a test result of initial cancer diagnosis that reveals the presence or absence of cancerous cells (e.g., using a biopsy and histology).

As used herein, the term "prostate tumor tissue" refers to cancerous tissue of the prostate.

In some embodiments, the prostate tumor tissue is "post surgical prostate tumor tissue."

As used herein, the term "post surgical tumor tissue" refers to cancerous tissue (e.g., prostate tissue) that has been removed from a subject (e.g., during surgery).

As used herein, the term "identifying the risk of said tumor metastasizing" refers to the relative risk (e.g., the percent chance or a relative score) of a tumor (e.g., prostate tumor tissue) metastasizing.

As used herein, the term "identifying the risk of said tumor recurring" refers to the relative risk (e.g., the percent chance or a relative score) of a tumor (e.g., prostate tumor tissue) recurring in the same organ as the original tumor (e.g., prostate).

As used herein, the term "subject at risk for cancer" refers to a subject with one or more risk factors for developing a specific cancer. Risk factors include, but are not limited to, gender, age, genetic predisposition, environmental expose, and previous incidents of cancer, preexisting non-cancer diseases, and lifestyle.

As used herein, the term "characterizing cancer in subject" refers to the identification of one or more properties of a cancer sample in a subject, including but not limited to, the presence of benign, pre-cancerous or cancerous tissue and the stage of the cancer. Cancers may be characterized by identifying cancer cells with the compositions and methods of the present invention. For example, cancers may be characterized by detecting expression of PSMA with the compositions and methods of the present invention.

As used herein, the term "stage of cancer" refers to a qualitative or quantitative assessment of the level of advancement of a cancer. Criteria used to determine the stage of a cancer include, but are not limited to, the size of the tumor, whether the tumor has spread to other parts of the body and where the cancer has spread (e.g., within the same organ or region of the body or to another organ).

Several staging methods are commonly used for cancer (e.g, prostate cancer). A common classification of the spread of prostate cancer was developed by the American Urological Association (AUA). The AUA system divides prostate tumors into four stages, A to D. Stage A, microscopic cancer within prostate, is further subdivided into stages A1 and A2. Sub-stage A1 is a well-differentiated cancer confined to one site within the prostate. Treatment is generally observation, radical prostatectomy, or radiation. Sub-stage A2 is a moderately to poorly differentiated cancer at multiple sites within the prostate. Treatment is radical prostatectomy or radiation. Stage B, palpable lump within the prostate, is also further subdivided into sub-stages B1 and B2. In sub-stage B1, the cancer forms a small nodule in one lobe of the prostate. In sub-stage B2, the cancer forms large or multiple nodules, or occurs in both lobes of the prostate. Treatment for sub-stages B1 and B2 is either radical prostatectomy or radiation. Stage C is a large cancer mass involving most or all of the prostate and is also further subdivided into two sub-stages. In sub-stage C1, the cancer forms a continuous mass that may have extended beyond the prostate. In sub-stage C2, the cancer forms a continuous mass that invades the surrounding tissue. Treatment for both these sub-stages is radiation with or without drugs to address the cancer. The fourth stage, Stage D is metastatic cancer and is also subdivided into two sub-stages. In sub-stage D1, the cancer appears in the lymph nodes of the pelvis. In sub-stage D2, the cancer involves tissues beyond lymph nodes. Treatment for both of these sub-stages is systemic drugs to address the cancer as well as pain.

As used herein, the term "GLEASON score" refers to a histologic grade that refers to the microscopic characteristics of malignant prostatic tumor. Individual areas receive a grade from 1 to 5. Cells that are well differentiated are given a low grade; poorly differentiated cells are given a high grade. A primary grade is assigned to the pattern occupying the greatest area of the specimen and a secondary grade is assigned to the second-largest affected area. These two grades are then added together for an overall Gleason score (or sum). The most well-differentiated cancer would receive a Gleason score of 2 (1+1), while the most poorly differentiated cancer would receive a Gleason score of 10 (5+5).

Staging of prostate cancer can also be based on the revised criteria of TNM staging by the American Joint Committee for Cancer (AJCC) published in 1988. Staging is the process of describing the extent to which cancer has spread from the site of its origin. It is used to assess a patient's prognosis and to determine the choice of therapy. The stage of a cancer is determined by the size and location in the body of the primary tumor, and whether it has spread to other areas of the body. Staging involves using the letters T, N and M to assess tumors by the size of the primary tumor (T); the degree to which regional lymph nodes (N) are involved; and the absence or presence of distant metastases (M)—cancer that has spread from the original (primary) tumor to distant organs or distant lymph nodes. Each of these categories is further classified with a number 1 through 4 to give the total stage. Once the T, N and M are determined, a "stage" of I, II, III or IV is assigned. Stage I cancers are small, localized and usually curable. Stage II and III cancers typically are locally advanced and/or have spread to local lymph nodes. Stage IV cancers usually are metastatic (have spread to distant parts of the body) and generally are considered inoperable.

As used herein, the term "characterizing tissue in a subject" refers to the identification of one or more properties of a tissue sample (e.g., including but not limited to, the presence of cancerous tissue, the presence of pre-cancerous tissue that is likely to become cancerous, and the presence of cancerous tissue that is likely to metastasize). In some embodiments, tissues are characterized detecting expression of PSMA with the compositions and methods of the present invention.

As used herein, the term "reagent(s) capable of specifically detecting PSMA expression" refers to reagents used to detect the expression and location of PSMA. Examples of suitable reagents include but are not limited to, the dendrimers of the present invention.

As used herein, the term "instructions for using said kit for detecting cancer in said subject" includes instructions for using the reagents contained in the kit for the detection and characterization of cancer in a sample from a subject.

As used herein, the terms "computer memory" and "computer memory device" refer to any storage media readable by a computer processor. Examples of computer memory include, but are not limited to, RAM, ROM, computer chips, digital video disc (DVDs), compact discs (CDs), hard disk drives (HDD), and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the terms "processor" and "central processing unit" or "CPU" are used interchangeably and refer to a device that is able to read a program from a computer memory (e.g., ROM or other computer memory) and perform a set of steps according to the program.

As used herein, the term "providing a prognosis" refers to providing information regarding the impact of the presence of cancer (e.g., as determined by the diagnostic methods of the present invention) on a subject's future health (e.g., expected morbidity or mortality, the likelihood of getting cancer, and the risk of metastasis).

As used herein, the term "non-human animals" refers to all non-human animals including, but not limited to, vertebrates such as rodents, non-human primates, ovines, bovines, ruminants, lagomorphs, porcines, caprines, equines, canines, felines, ayes, etc.

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, dendrimers, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. As used herein, the term "adenovirus gene transfer system" refers to gene transfer systems comprising intact or altered viruses belonging to the family Adenoviridae.

As used herein, the term "site-specific recombination target sequences" refers to nucleic acid sequences that provide recognition sequences for recombination factors and the location where recombination takes place.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "transgene" refers to a heterologous gene that is integrated into the genome of an organism (e.g., a non-human animal) and that is transmitted to progeny of the organism during sexual reproduction.

As used herein, the term "transgenic organism" refers to an organism (e.g., a non-human animal) that has a transgene integrated into its genome and that transmits the transgene to its progeny during sexual reproduction.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence that encodes a gene product. The coding region may be present in a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the terms "complementary" or "complementarity" are used in reference to polynucleotides (i.e., a sequence of nucleotides) related by the base-pairing rules. For example, for the sequence "5'-A-G-T-3'," is complementary to the sequence "5'-T-C-A-3'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G}+\text{C})$, when a nucleic acid is in aqueous solution at 1 M NaCl (See e.g., Anderson and Young, Quantitative Filter Hybridization, in Nucleic Acid Hybridization (1985)). Other references include more sophisticated computations that take structural as well as sequence characteristics into account for the calculation of $T_m$.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (Kacian et al., Proc. Natl. Acad. Sci. USA 69:3038 (1972)). Other nucleic acids will not be replicated by this amplification enzyme. Similarly, in the case of T7 RNA polymerase, this amplification enzyme has a stringent specificity for its own promoters (Chamberlin et al., Nature 228:227 (1970)). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics 4:560 (1989)). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), PCR Technology, Stockton Press (1989)).

As used herein, the term "amplifiable nucleic acid" is used in reference to nucleic acids that may be amplified by any amplification method. It is contemplated that "amplifiable nucleic acid" will usually comprise "sample template."

As used herein, the term "sample template" refers to nucleic acid originating from a sample that is analyzed for the presence of "target." In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," refers to the region of nucleic acid bounded by the primers. Thus, the "target" is sought to be sorted out from other nucleic acid sequences. A "segment" is defined as a region of nucleic acid within the target sequence.

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

"Amino acid sequence" and terms such as "polypeptide" or "protein" are not meant to limit the amino acid sequence to the complete, native amino acid sequence associated with the recited protein molecule.

The term "native protein" as used herein to indicate that a protein does not contain amino acid residues encoded by vector sequences; that is, the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., Molecular Cloning: A Laboratory Manual, Cold Spring Harbor Press, NY, pp 9.31-9.58 (1989)).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al., supra, pp 7.39-7.52 (1989)).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabeled antibodies.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "overexpression" and "overexpressing" and grammatical equivalents, are used in reference to levels of mRNA to indicate a level of expression approximately 3-fold higher (or greater) than that observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 (1973)), has been modified by several groups to optimize conditions for particular types of cells. The art is well aware of these numerous modifications.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

As used herein, the term "selectable marker" refers to the use of a gene that encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene that is used in conjunction with tk⁻ cell lines, the CAD gene that is used in conjunction with CAD-deficient cells and the mammalian hypoxanthine-guanine phosphoribosyl transferase (hprt) gene that is used in conjunction with hprt⁻ cell lines. A review of the use of selectable markers in mammalian cell lines is provided in Sambrook, J. et al., Molecular Cloning: A Laboratory Manual, 2nd ed., Cold Spring Harbor Laboratory Press, New York (1989) pp. 16.9-16.15.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used herein, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using the screening methods of the present invention.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

As used herein, the term "NAALADase inhibitor" refers to any one of a multitude of inhibitors for the neuropeptidase NAALADase (N-acetylated-alpha linked acidic dipeptidase). Such inhibitors of NAALADase have been well characterized. For example, an inhibitor can be selected from the group comprising, but not limited to, those found in U.S. Pat. No. 6,011,021, herein incorporated by reference in its entirety.

As used herein, the term "nanodevice" or "nanodevices" refer, generally, to compositions comprising dendrimers of the present invention. As such, a nanodevice may refer to a composition comprising a dendrimer and metal nanoparticles (e.g., iron oxide nanoparticles (e.g., poly(styrene sulfonate) (PSS)-coated iron oxide nanoparticles)) of the present invention that may contain one or more functional groups (e.g., a therapeutic agent) conjugated to the dendrimer. A nanodevice may also refer to a composition comprising two or more different dendrimers of the present invention.

As used herein, the term "degradable linkage," when used in reference to a polymer (e.g., PEG-hRNase conjugate of the present invention), refers to a conjugate that comprises a physiologically cleavable linkage (e.g., a linkage that can be hydrolyzed (e.g., in vivo) or otherwise reversed (e.g., via enzymatic cleavage). Such physiologically cleavable linkages include, but are not limited to, ester, carbonate ester, carbamate, sulfate, phosphate, acyloxyalkyl ether, acetal, and ketal linkages (See, e.g., U.S. Pat. No. 6,838,076, herein incorporated by reference in its entirety). Similarly, the conjugate may comprise a cleavable linkage present in the linkage between the polymer and hRNase, or, may comprise a cleavable linkage present in the polymer itself (e.g., such that when cleaved, a small portion of the polymer remains on the hRNase molecule) (See, e.g., U.S. Pat. App. Nos. 20050158273 and 20050181449, each of which is herein incorporated by reference in its entirety). For example, a PEG polymer comprising an ester linkage can be utilized for conjugation to hRNase to create a PEG-hRNase conjugate (See, e.g., Kuzlowski et al., Biodrugs, 15, 419-429 (2001). A conjugate that comprises a degradable linkage of the present invention is capable of generating hRNase that is free (e.g., completely or partially free) of the polymer (e.g., in vivo after hydrolysis of the linkage).

A "physiologically cleavable" or "hydrolysable" or "degradable" bond is a bond that reacts with water (i.e., is hydrolyzed) under physiological conditions. The tendency of a bond to hydrolyze in water will depend not only on the general type of linkage connecting two central atoms but also on the substituents attached to these central atoms. Appropriate hydrolytically unstable or weak linkages include but are not limited to carboxylate ester, phosphate ester, anhydrides, acetals, ketals, acyloxyalkyl ether, imines, orthoesters, peptides and oligonucleotides.

An "enzymatically degradable linkage" means a linkage that is subject to degradation by one or more enzymes.

A "hydrolytically stable" linkage or bond refers to a chemical bond (e.g., typically a covalent bond) that is substantially stable in water (i.e., does not undergo hydrolysis under physiological conditions to any appreciable extent over an extended period of time). Examples of hydrolytically stable linkages include, but are not limited to, carbon-carbon bonds (e.g., in aliphatic chains), ethers, amides, urethanes, and the like.

DETAILED DESCRIPTION OF THE INVENTION

The present invention relates to novel therapeutic and diagnostic dendrimers. In particular, the present invention is directed to dendrimer-linker conjugates, methods of synthesizing the same, compositions comprising the conjugates, as well as systems and methods utilizing the conjugates (e.g., in diagnostic and/or therapeutic settings (e.g., for the delivery of therapeutics, imaging, and/or targeting agents (e.g., in disease (e.g., cancer) diagnosis and/or therapy, pain therapy, etc.)). Accordingly, dendrimer-linker conjugates of the present invention may further comprise one or more components for targeting, imaging, sensing, and/or providing a therapeutic or diagnostic material and/or monitoring response to therapy.

Accordingly, in some embodiments, the present invention provides a linker conjugated to a targeting agent (e.g., that can be conjugated to a dendrimer (e.g., for specific targeting of the dendrimer)). Thus, in some embodiments, the present invention provides methods of synthesizing dendrimer conjugates (e.g., PAMAM dendrimers) comprising linkers (e.g., conjugated to a trigger moiety, therapeutic moiety and/or other type of moiety) compositions comprising the same, and methods of using the same in the diagnosis, imaging and treatment of disease (e.g., cancer, inflammatory disease, chronic pain, etc.).

The present invention provides a multiplicity of linkers and targeting agents that find use in the present invention. Indeed, the present invention is not limited to any particular linker or to any particular targeting agent or to any particular dendrimer. In some embodiments, the present invention provides a dendrimer conjugated to a linker that is conjugated to a targeting agent, and methods of generating and using the same (e.g., to treat cancer, pain and/or inflammation, etc.). In some embodiments, a dendrimer conjugated to a linker that is conjugated to a targeting agent decreases the number of conjugation steps required to form a dendrimer (e.g., a dendrimer conjugate (e.g., a dendrimer conjugated to a targeting agent, imaging agent, therapeutic agent and/or sensing agent)). For example, in some embodiments, the present invention provides a customizable dendrimer wherein one or a plurality of linkers (e.g. attached to one or a plurality of targeting agents, triggering agents and/or therapeutic agents) are conjugated to a dendrimer, thereby decreasing the number of conjugation steps used to form a dendrimer (e.g., versus a dendrimer that is conjugated to a targeting moiety in one step and that is separately conjugatd to a linker (e.g., comprising a therapeutic agent, imaging agent, sensing agent or other moiety) in an additional conjugation step). In some embodiments, a linker conjugated to one or more targeting agents is conjugated to one or more additional moieties including, but not limited to, a therapeutic agent, a triggering agent, an imaging agent, a sensing agent, etc. Thus, in some embodiments, the present invention provides a dendrimer with increased load capacity (e.g., increased load of therapeutic, imaging agent, etc. on the dendrimer). In some embodiments, two or more linkers (e.g., conjugated to one or a plurality of targeting agents) are conjugated to a dendrimer via the same or different linkage (e.g., covalent linkage).

Several different schemes were evaluated for generating dendrimer conjugates wherein a dendrimer is conjugated to one or more linkers that comprise multiple sites for binding (e.g., covalent binding) moieties. For example, in one embodiment, a linker may comprise a chemical structure that allows conjugation of a targeting moiety and a therapeutic compound to the linker. Thus, in some embodiments, a dendrimer conjugate of the present invention permits control of the stoichiometry between targeting agent and therapeutic compound (e.g., generation of one to one ratio, two to one ratio, one to two ratio, one to three ratio etc. between targeting and therapeutic moieties).

In some embodiments, a dendrimer conjugated to a linker that is conjugated to a targeting agent and/or therapeutic comprises a linker that is configured to be irreversibly degraded (e.g., that is non-reversible (e.g., that permits drug delivery at the correct time and/or at the correct place)).

Figure 2:
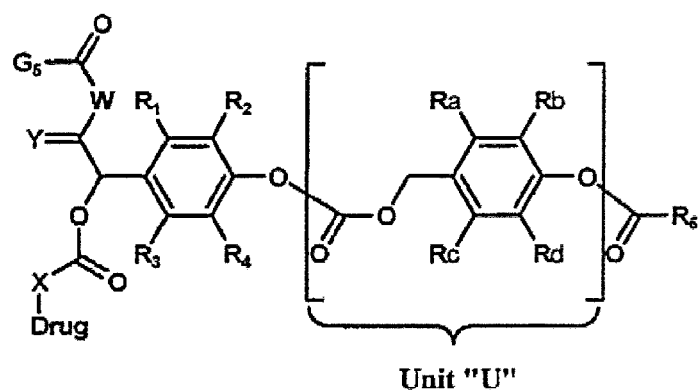
FIG. 2 shows diagrams of a dendrimer conjugate provided in some embodiments of the present invention.
Figure 1:
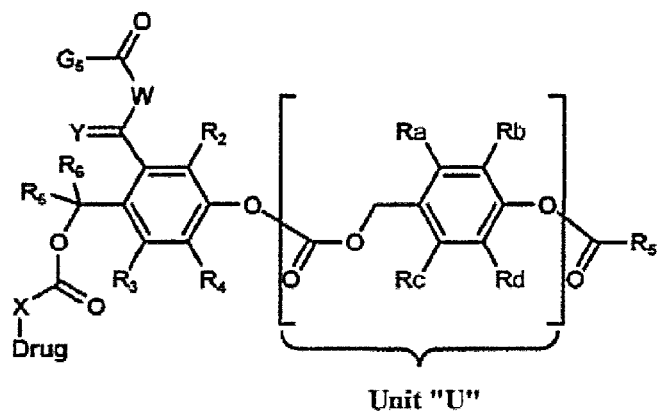
Figure 2:
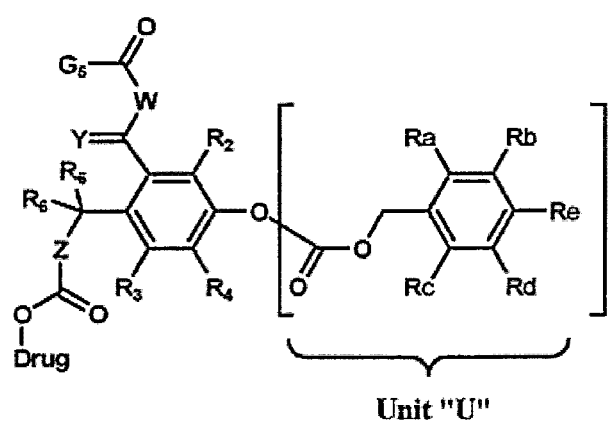

In some embodiments, the present invention provides a dendrimer conjugate as shown in FIG. 1. For example, FIG. 1 shows a targeting agent (T.A.) conjugated to a linker that is also conjugated to a drug, wherein the linker conjugated to a drug and targeting agent is conjugated to a dendrimer conjugated to an imaging agent. In some embodiments, the present invention provides a dendrimer conjugate as shown in FIG. 2 (e.g., possessing targeted anticancer therapeutic moiety). For example, FIG. 2 shows several structures of dendrimer conjugates, wherein R1, R2, R3 and R4 are each independently selected from hydrogen, halogen, and alkyl. In some embodiments, the alkyl is straight or cyclic, unsubstituted or substituted (e.g., by from 1 to 4 substituents (e.g., selected from the group comprising, but not limited to, halogen, amino, monoalkylamino, dialkylamino, hydroxy, alkoxy, nitro, aryl, cyano, carboxyl, carboxamide, monoalkylcarboxamide, dialkylcarboxamide, thiol, thioalkyl and sulfonic acid. In some embodiments, the "U" moiety is present or absent. In some embodiments, when the "U" moiety is absent, one of the R1, R2, R3 and/or R4 groups is linked to a targeting agent through a linker and/or spacer. In some embodiments, R5 is an alkyl (e.g., that is straight chained, branched, cyclic (e.g., that is substituted or unsubtituted)). In some embodiments, R6 is a hydrogen or an alkyl (e.g., of 1-4 carbons (e.g., that are straight chained or cyclic (e.g., that is substituted or unsubstituted)). In some embodiments, Ra, Rb, Rc, Rd and Re are each independently selected from hydrogen, halogen, and alkyl. In some embodiments, the alkyl is straight or cyclic, unsubstituted or substituted (e.g., by from 1 to 4 substituents (e.g., selected from halogen, amino, monoalkylamino, dialkylamino, hydroxy, alkoxy, nitro, aryl, cyano, carboxyl, carboxamide, monoalkylcarboxamide, dialkylcarboxamide, thiol, thioalkyl and sulfonic acid. In some embodiments, the "U" moiety is present or absent. In some embodiments, when the "U" moiety is absent, one of the Ra, Rb, Rc, Rd and Re groups is linked to a targeting agent through a linker and/or spacer. In some embodiments, "Y" is an oxygen atom. In some embodiments, "Y" is two hydrogen atoms. In some embodiments, G5 is a generation five poly (amidoamine) (PAMAM) dendrimer (e.g., conjugated to one or more imaging agents (e.g., FITC, etc.), although higher (e.g., G6, G7, G8, G9, G10 or higher, or lower, G4, G3, or G2 dendrimers may also be used. In some embodiments, "W" is a linker comprising 1-8 carbon and/or nitrogen atoms (e.g., straight chanined, branched, or cyclic, unsubstituted or substituted by "R" groups as described above.

Figure 3:
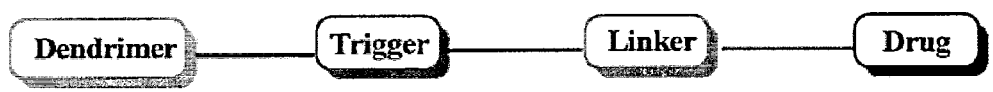
FIG. 3 shows a diagram of a dendrimer conjugate provided in some embodiments of the present invention.
Figure 4:
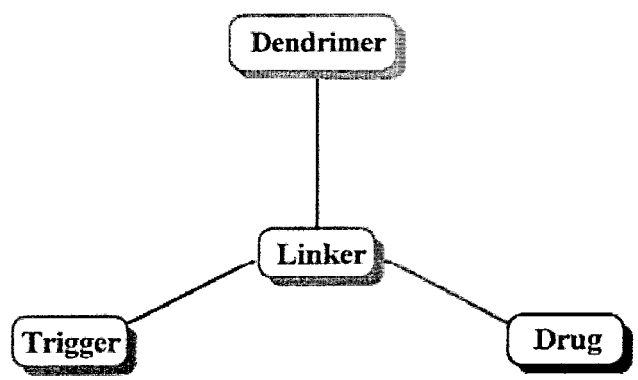
FIG. 4 shows a diagram of a dendrimer conjugate provided in some embodiments of the present invention.

In some embodiments, the present invention provides a dendrimer conjugate as shown in FIGS. 3 and 4. In particular, a dendrimer conjugate as shown in FIG. 3 comprises a dendrimer (e.g., a G5 PAMAM dendrimer conjugated to an imaging agent (e.g., FITC) and/or targeting agent) conjugated to a trigger molecule that is conjugated to a linker that is conjugated to a therapeutic. A dendrimer conjugate as shown in FIG. 4 comprises a dendrimer (e.g., a G5 PAMAM dendrimer conjugated to an imaging agent (e.g., FITC) and/or targeting agent) conjugated to a linker that is conjugated to a trigger and to a therapeutic moiety. The conjugates of FIGS. 3 and 4 are configured to be non-toxic to normal cells. For example, the conjugates are configured in such a way so as to release their therapeutic agent only at a specific, targeted site (e.g., through activation of a trigger molecule that in to leads to release of the therapeutic agent) For example, once a conjugate arrives at a target site in a subject (e.g., a tumor, or a site of inflammation), components in the target site (e.g., a tumor associated factor, or an inflammatory or pain associated factor)

interacts with the trigger moiety thereby initiating cleavage of this unit from the linker. In some embodiments, once the trigger is cleaved from the linker (e.g., by a target associated moiety), the linker proceeds through spontaneous chemical breakdown thereby releasing the therapeutic agent at the target site (e.g., in its active form). The present invention is not limited to any particular target associated moiety (e.g., that interacts with and initiates cleavage of a trigger). In some embodiments, the target associated moiety is a tumor associated factor (e.g., an enzyme (e.g., glucuronidase and/or plasmin), a cathepsin, a matrix metalloproteinase, a hormone receptor (e.g., integrin receptor, hyaluronic acid receptor, luteinizing hormone-releasing hormone receptor, etc.), cancer and/or tumor specific DNA sequence), an inflammatory associated factor (e.g., chemokine, cytokine, etc.) or other moiety.

Figure 5:
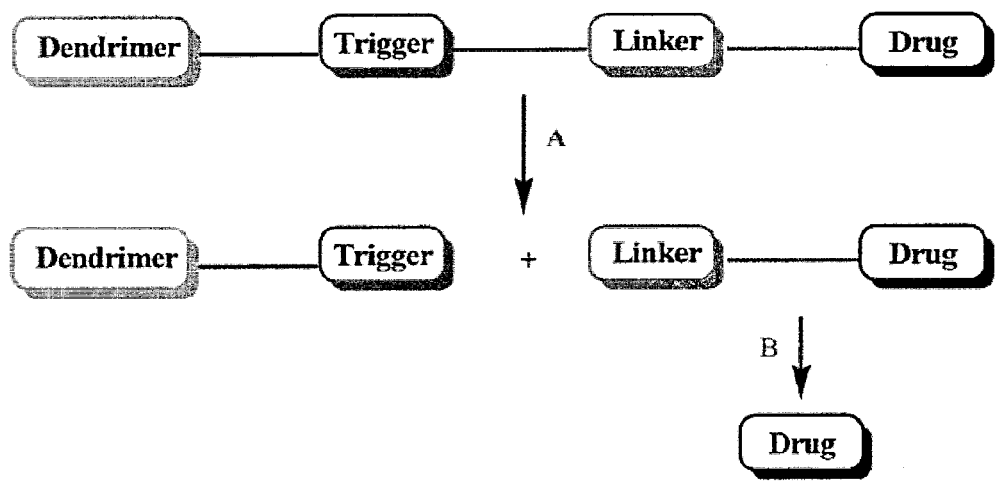
FIG. 5 shows a diagram of a dendrimer conjugate provided in some embodiments of the present invention.
Figure 6:
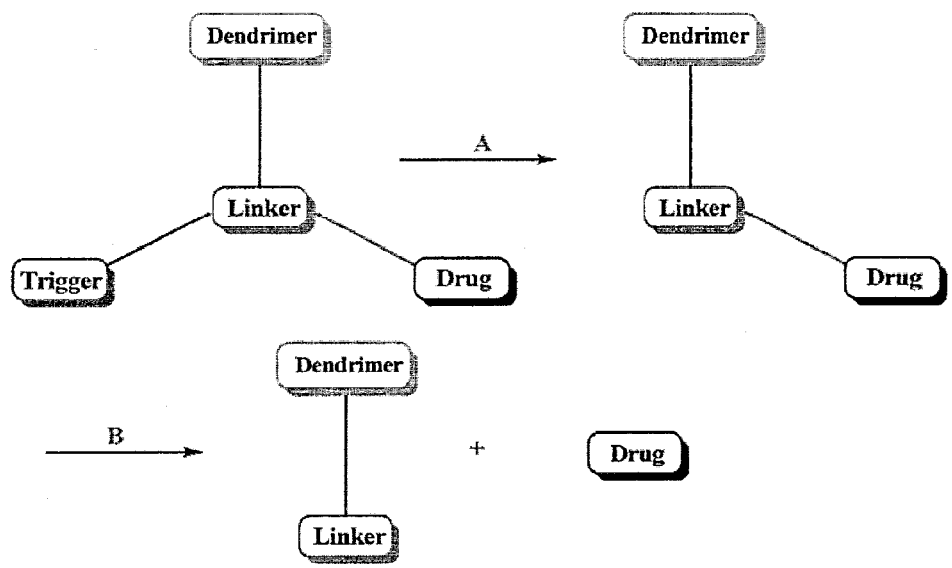
FIG. 6 shows a diagram of a dendrimer conjugate provided in some embodiments of the present invention.
Figure 7:
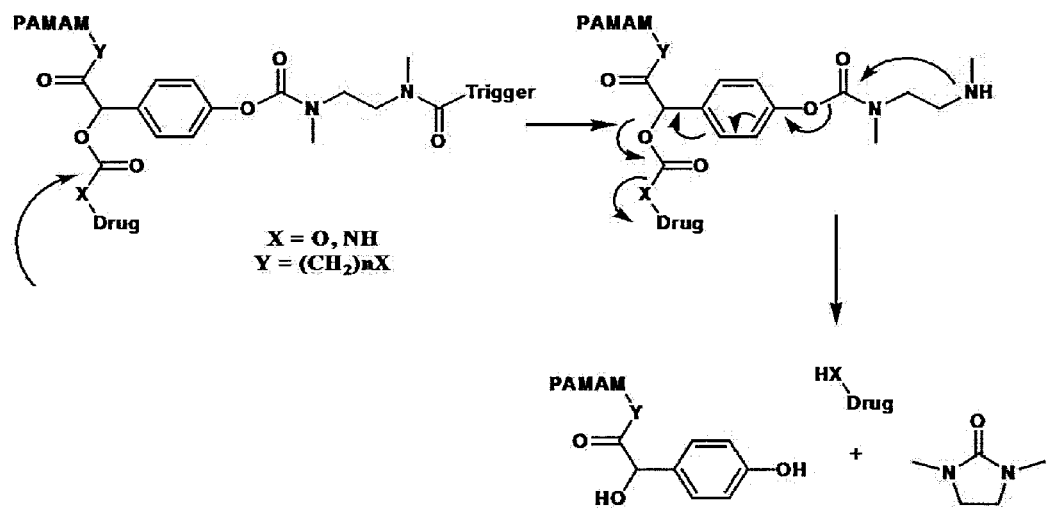
FIG. 7 shows the release of a therapeutic compound from a dendrimer conjugate in one embodiment of the invention.
Figure 8:
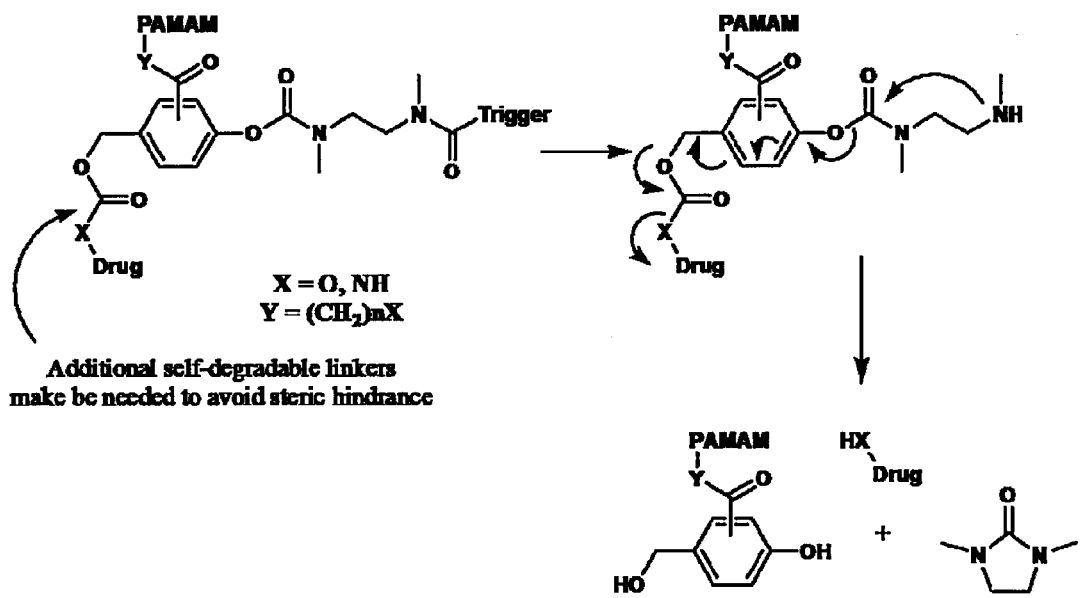
FIG. 8 shows the release of a therapeutic compound from a dendrimer conjugate in one embodiment of the invention.

Although an understanding of a mechanism of action is not necessary to practice the present invention, and the present invention is not limited to any particular mechanism of action, in some embodiments, a dendrimer conjugate as described in FIG. 3 or 4 provides a therapeutic to a site by a mechanism as shown in FIG. 5 or 6. For example, as shown in FIG. 5, a dendrimer conjugate comprising a dendrimer (e.g., a G5 PAMAM dendrimer conjugated to an imaging agent (e.g., FITC) and/or targeting agent) conjugated to a trigger molecule that is conjugated to a linker that is conjugated to a therapeutic (A) interacts with a target associated moiety thereby activating the trigger and initiating cleavage of same, releasing the linker therapeutic drug conjugate. Once cleavage of the trigger occurs, the linker (B) proceeds through a spontaneous chemical breakdown at the target site, releasing (e.g., irreversibly releasing) the therapeutic drug at the target site. In some embodiments, as shown in FIG. 6, a dendrimer conjugate comprising a dendrimer (e.g., a G5 PAMAM dendrimer conjugated to an imaging agent (e.g., FITC) and/or targeting agent) conjugated to a linker that is conjugated to a trigger and to a therapeutic moiety (A) interacts with a target associated moiety thereby activating the trigger and initiating cleavage of same, releasing a dendrimer-linker-therapeutic moiety from the trigger. Once cleavage of the trigger occurs, the linker (B) proceeds through a spontaneous chemical breakdown (e.g., to a point where the therapeutic drug is released from the dendrimer linker conjugate) at the target site, releasing (e.g., irreversibly releasing) the therapeutic drug at the target site. Several design processes for generating a dendrimer conjugate comprising a trigger are shown in FIGS. 7 and 8.

The dendrimer conjugates shown in FIGS. 3 and 4 are not limited to any particular dendrimer. Indeed, the conjugates may comprise a variety of different types of dendrimers. In some embodiments, the dendrimer is a PAMAM dendrimer (e.g., G3, G5 or G7 dendrimer). In some embodiments, one or more amino groups present on the dendrimer are linked (e.g., through a covalent bond) to one or more targeting agents (e.g., folic acid) and/or imaging agents (e.g., FITC) (e.g., as described in U.S. Pat. Nos. 6,471,968 and 7,078,461; U.S. Patent Pub. Nos. 20020165179 and 20070041934 and WO 06/033766, each of which is hereby incorporated by reference in its entirety for all purposes).

Figure 9:
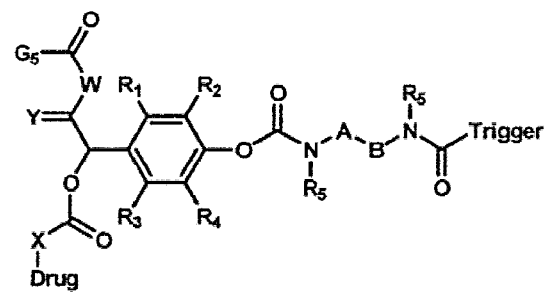
FIGS. 9A-9D show diagrams of a dendrimer conjugate provided in some embodiments of the present invention.
Figure 1:
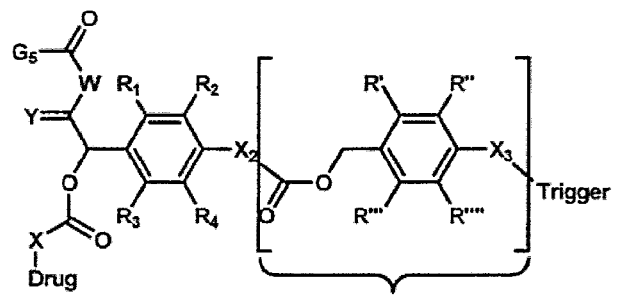
Figure 9:
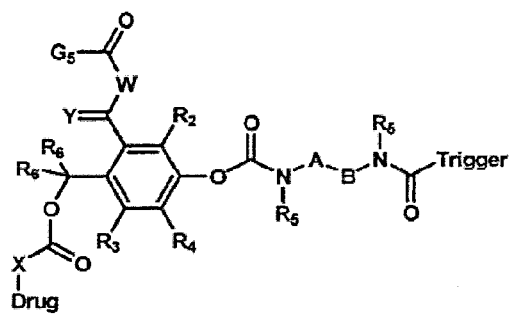
Figure 2:
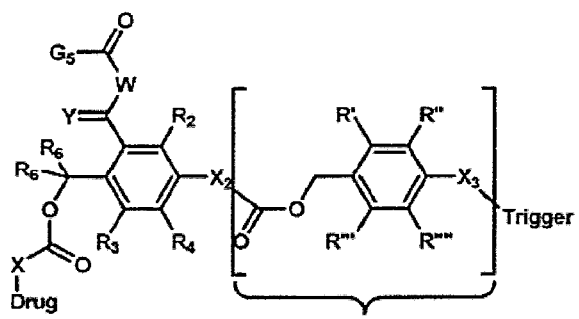

In some embodiments, the present invention provides a dendrimer conjugate as shown in FIG. 9. In particular, a dendrimer conjugate as shown in FIG. 9 comprises a dendrimer (e.g., a G5 PAMAM dendrimer conjugated to an imaging agent (e.g., FITC) and/or targeting agent) conjugated to a trigger molecule that is conjugated to a linker that is conjugated to a therapeutic, or a dendrimer (e.g., a G5 PAMAM dendrimer conjugated to an imaging agent (e.g., FITC) and/or targeting agent) conjugated to a linker that is conjugated to a trigger and to a therapeutic moiety.). For example, FIG. 9 shows several structures of dendrimer conjugates, wherein R1, R2, R3 and R4 are each independently selected from hydrogen, halogen, and alkyl. In some embodiments, the alkyl is straight or cyclic, unsubstituted or substituted (e.g., by from 1 to 4 substituents (e.g., selected from the group comprising, but not limited to, halogen, amino, monoalkylamino, dialkylamino, hydroxy, alkoxy, nitro, aryl, cyano, carboxyl, carboxamide, monoalkylcarboxamide, dialkylcarboxamide, thiol, thioalkyl and sulfonic acid. In some embodiments, R5 is an alkyl that is straight, branched or cyclic, that is unsubstituted or substituted. In some embodiments, R6 is a hydrogen or alkyl of 1-4 carbons that are straight, branched or cyclic, that is unsubstituted or substituted. In some embodiments, the two R6 are connected together to form a ring of 306 members. In some embodiments, R', R'', R''' and R'''' are each independently selected from hydrogen, halogen, and alkyl. In some embodiments, the alkyl is straight or cyclic, unsubstituted or substituted (e.g., by from 1 to 4 substituents (e.g., selected from the group comprising, but not limited to, halogen, amino, monoalkylamino, dialkylamino, hydroxy, alkoxy, nitro, aryl, cyano, carboxyl, carboxamide, monoalkylcarboxamide, dialkylcarboxamide, thiol, thioalkyl and sulfonic acid. In some embodiments, X, X2 and X3 are either oxygen or "NR", wherein "N" is a nitrogen atom, and "R" is an alkyl that is straight or branched or cyclic (e.g., substituted or unsubstituted). In some embodiments, "Y" is an oxygen atom or two hydrogen atoms. In some embodiments, A-B is an ethylene group (e.g., unsubstituted or substituted by alkyls (e.g., straight or cyclic). In some embodiments, A-B are connected by a carbon chain (e.g., of 2, 3, 4, 5, or more carbons) and/or hetero atoms (e.g., forming a saturated or unsaturated aromatic ring structure (e.g., comprising substituents such as R1, R2, R3 and R4). In some embodiments, G5 is a dendrimer (e.g., a G5 PAMAM dendrimer conjugated to an imaging agent (e.g., FITC) and/or targeting agent). As described herein, the present invention is not limited to any particular dendrimer. In some embodiments, "W" is a linker (e.g., comprising a carbon or nitrogen chain (e.g., 2, 3, 4, 5, 6, 7, 8, 9, or more carbons or nitrogens (e.g., straight or branched or cyclic (e.g., substituted or unsubstituted (e.g., with R groups as described above))).

The present invention is not limited by the type of dendrimer conjugate (e.g., comprising a trigger) for use in treating a subject. For example, the present invention contemplates dendrimer conjugates comprising one or more anticancer prodrugs developed for site specific conversion to drug based on tumor associated factors (e.g., hypoxia and pH, tumor-associated enzymes, and/or receptors). In some embodiments, dendrimer conjugates of the present invention are configured such that a prodrug (e.g., anticancer prodrug) is conjugated to a linker that is further conjugated to a targeting moiety (e.g., that targets the conjugate to a site of cancer and/or tumor). Although an understanding of the mechanism is not necessary for the present invention, and the present invention is not limited to any particular mechanism of action, in some embodiments, a trigger component serves as a precursor for site-specific activation. For example, in some embodiments, once a tumor-associated factor recognizes a trigger, cleavage and/or processing of the trigger is induced. The present invention is not limited to any particular trigger or to any particular cleavage and/or processing of the trigger. In some embodiments, the present invention provides a dendrimer conjugate comprising a trigger that is sensitive to (e.g., is cleaved by) and/or that associates with a tumor associated enzyme. In some embodiments, the present invention provides a dendrimer conjugate comprising a trigger that is sensitive to (e.g., is cleaved by) and/or that associates with a glucuronidase. Glucuronic acid can be attached to several anticancer drugs via various linkers. These anticancer drugs include, but are not limited to, doxorubicin, paclitaxel, docetaxel, 5-fluorouracil, 9-aminocamtothecin, as well as other drugs under development. These prodrugs are generally stable at physiological pH and are significantly less toxic than the parent drugs. In some embodiments, dendrimer conjugates comprising anticancer prodrugs find use for treating necrotic tumors (e.g., that liberate β-glucuronidase) or for ADEPT with antibodies that can deliver β-glucuronidase to target tumor cells. An example of an anticancer prodrug is shown in Figure such prodrugs is shown below:

In some embodiments, the present invention provides a dendrimer conjugate comprising a trigger that is sensitive to (e.g., is cleaved by) and/or that associates with a protease. The present invention is not limited to any particular protease. In some embodiments, the protease is a cathepsin. In some embodiments, a trigger comprises a Lys-Phe-PABC moiety (e.g., that acts as a trigger). In some embodiments, a Lys-Phe-PABC moiety linked to doxorubicin, mitomycin C, and paclitaxel are utilized as a trigger-therapeutic conjugate in a dendrimer conjugate provided herein (e.g., that serve as substrates for lysosomal cathepsin B or other proteases expressed (e.g., overexpressed) in tumor cells. In some embodiments, utilization of a 1,6-elimination spacer/linker is utilized (e.g., to permit release of therapeutic drug post activation of trigger).

In some embodiments, the present invention provides a dendrimer conjugate comprising a trigger that is sensitive to (e.g., is cleaved by) and/or that associates with plasmin. The serine protease plasmin is over expressed in many human tumor tissues. Tripeptide specifiers (e.g., including, but not limited to, Val-Leu-Lys) have been identified and linked to anticancer drugs through elimination or cyclization linkers.

In some embodiments, the present invention provides a dendrimer conjugate comprising a trigger that is sensitive to (e.g., is cleaved by) and/or that associates with a matrix metalloproteases (MMPs). In some embodiments, the present invention provides a dendrimer conjugate comprising a trigger that is sensitive to (e.g., is cleaved by) and/or that associates with β-Lactamase (e.g., a β-Lactamase activated cephalosporin-based prodrug).

Figure 18:
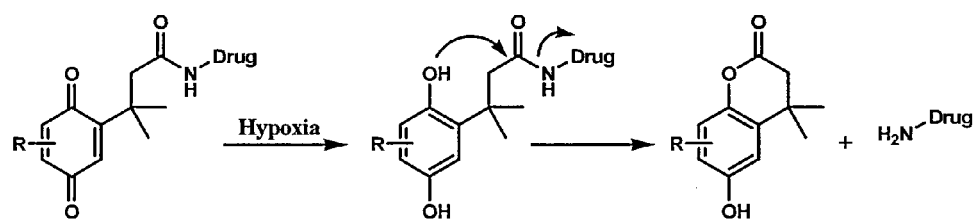
FIG. 18 shows an example of a dendrimer conjugate designed for hypoxia induced activation in one embodiment of the present invention.
Figure 19:
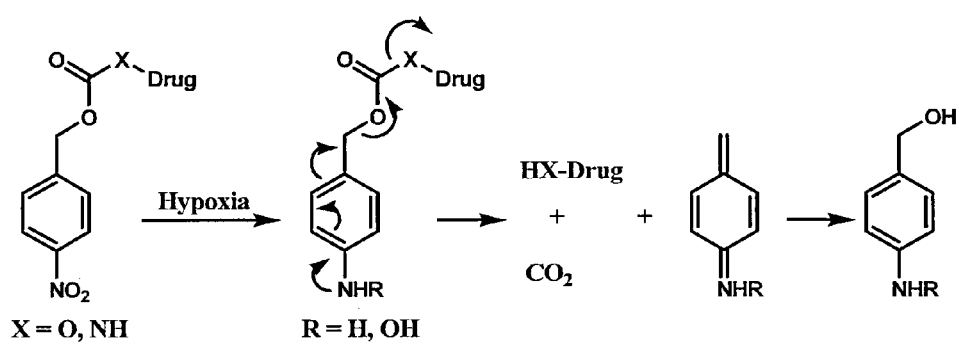
FIG. 19 shows that, in some embodiments, a heteroaromatic nitro compound present in a dendrimer conjugate of the present invention is reduced to either an amine or a hydroxylamine, thereby triggering the spontaneous release of a therapeutic agent/drug.

In some embodiments, the present invention provides a dendrimer conjugate comprising a trigger that is sensitive to (e.g., is cleaved by) hypoxia (e.g., indolequinone) (e.g., as described in Example 8). Hypoxia is a feature of several disease states, including cancer, inflammation and rheumatoid arthritis. Advances in the chemistry of bioreductive drug activation have led to the design of various hypoxia-selective drug delivery systems in which the pharmacophores of drugs are masked by reductively cleaved groups. In some embodiments, a dendrimer conjugate of the present invention utilizes a quinone, N-oxide and/or (hetero)aromatic nitro groups. For example, a quinone present in a dendrimer conjugate of the present invention is reduced to phenol under hypoxia conditions, with spontaneous formation of lactone that serves as a driving force for drug release (e.g., as shown in FIG. 18). In some embodiments, the quinone is an indolequinone. In some embodiments, a heteroaromatic nitro compound present in a dendrimer conjugate of the present invention is reduced to either an amine or a hydroxylamine, thereby triggering the spontaneous release of a therapeutic agent/drug (e.g., as shown in FIG. 19).

In some embodiments, the present invention provides a dendrimer conjugate comprising a trigger that is sensitive to (e.g., is cleaved by) and/or activated by a receptor (e.g., expressed on a target cell (e.g., a tumor cell)). Thus, in some embodiments, a dendrimer conjugate comprises a receptor binding motif conjugated to a therapeutic agent (e.g., cytotoxic drug) thereby providing target specificity. Examples include, but are not limited to, a dendrimer conjugate comprising a prodrug (e.g., of doxorubicin and/or paclitaxel) targeting integrin receptor, a hyaluronic acid receptor, and/or a hormone receptor.

In some embodiments, the present invention provides a dendrimer conjugate comprising a trigger that is sensitive to (e.g., is cleaved by) and/or activated by a nucleic acid. Nucleic acid triggered catalytic drug release can be utilized in the design of chemotherapeutic agents. Thus, in some embodiments, disease specific nucleic acid sequence is utilized as a drug releasing enzyme-like catalyst (e.g., via complex formation with a complimentary catalyst-bearing nucleic acid and/or analog).

In some embodiments, the present invention provides a dendrimer conjugate comprising a linker that connects a trigger to a therapeutic compound. In some embodiments, the linker is configured such that its decomposition leads to the liberation (e.g., non-reversible liberation) of the therapeutic agent (e.g., at the target site (e.g., site of tumor, or inflammatory site)). The linker may influence multiple characteristics of a dendrimer conjugate including, but not limited to, properties of the therapeutic agent (e.g., stability, pharmacokinetic, organ distribution, bioavailability, and/or enzyme recognition (e.g., when the therapeutic agent (e.g., prodrug)) is enzymatically activated)).

Figure 20:
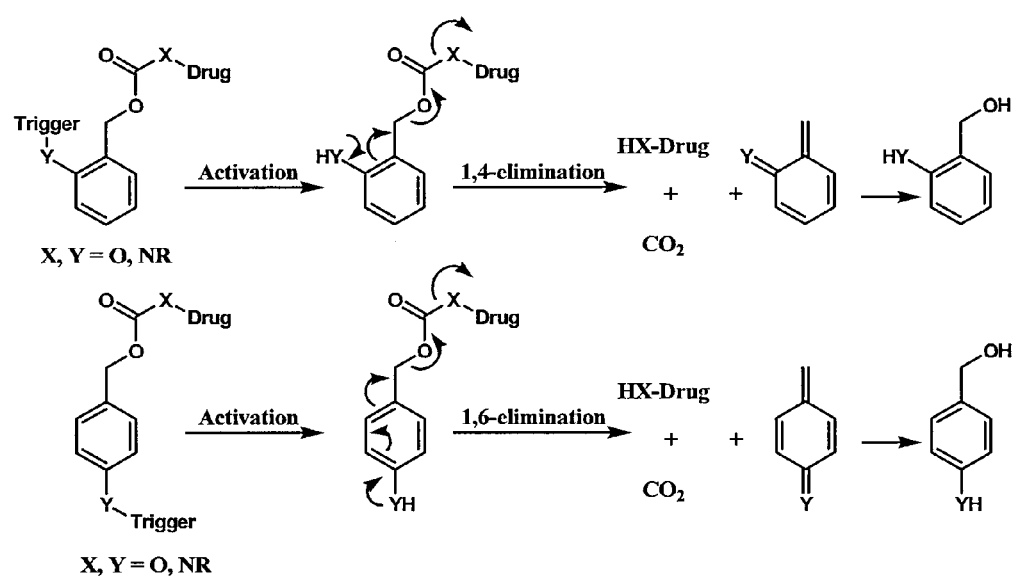
FIG. 20 depicts the activation of a dendrimer conjugate comprising either a 1,4 or a 1,6 elimination linker in embodiments of the present invention.
Figure 21:
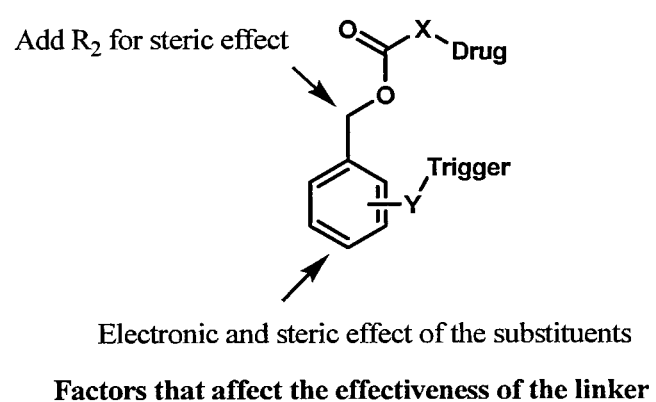
FIG. 21 shows that a spacer (R2) can be used to decrease steric hindrance in a dendrimer conjugate in some embodiments of the present invention.

In some embodiments, the linker is an elimination linker. For example, in some embodiments, in a dendrimer conjugate of the present invention, when a trigger is cleaved (e.g., enzymatically and/or chemically), a phenol or an aniline promotes a facile 1,4 or 1,6 elimination, followed by release of a $CO_2$ molecule and the unmasked therapeutic agent (e.g., drug) (See, e.g., FIG. 20). In some embodiments, a dendrimer conjugate of the present invention utilizes this configuration and/or strategy to mask one or more hydroxyl groups and/or amino groups of the therapeutic agents. In some embodiments, a linker present within a dendrimer conjugate of the present invention is fine tuned (e.g., to optimize stability and/or drug release from the conjugate). For example, the sizes of the aromatic substituents can be altered (e.g., increased or decreased) and/or alkyl substitutions at the benzylic position may be made to alter (e.g., increase or decrease) degradation of the linker and/or release of the therapeutic agent (e.g., prodrug). In some embodiments, elongated analogs (e.g., double spacers) are used (e.g., to decrease steric hindrance (e.g., for large therapeutic agents (e.g., See FIG. 21))). In some embodiments, a dendrimer conjugate of the present invention comprises an enol based linker (e.g., that undergoes an elimination reaction to release therapeutic agent (e.g., prodrug)).

Figure 22:
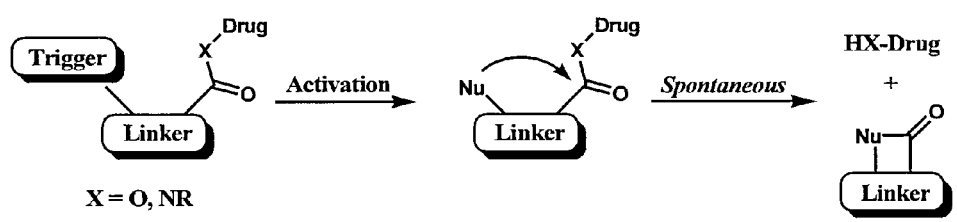
FIG. 22 depicts a dendrimer conjugate comprising a cyclization based linker in some embodiments of the present invention.
Figure 23:
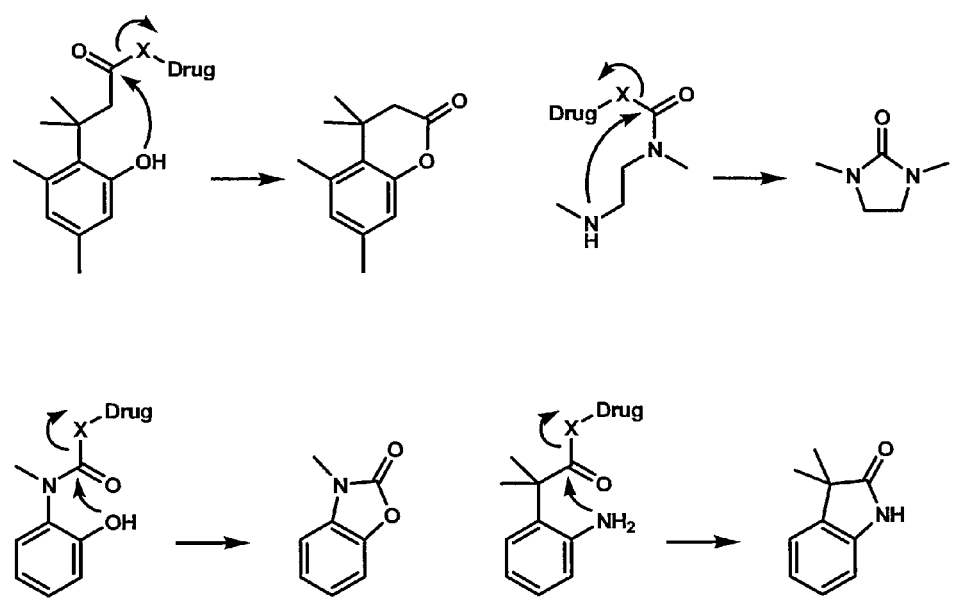
FIG. 23 depicts cyclization based linkers in some embodiments of the invention.

In some embodiments, the linker is a cyclization based linker. For example, one configuration for this approach is shown in FIG. 22. A nucleophilic group (e.g., OH or NHR) that becomes available once the trigger is cleaved attacks the carbonyl of the C(O)X-Therapeutic agent/drug (e.g., thereby leading to release of therapeutic agent-XH). function and thereby to quickly release the Drug-XH. In some embodiments, a driving force that permits the reaction to reach completion is the stability of the cyclic product. In some embodiments, a cyclization based linker of a dendrimer conjugate of the present invention include, but are not limited to, those shown in FIG. 23.

Figure 24:
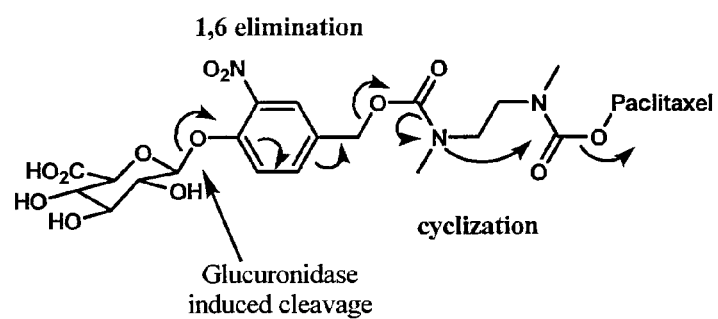
FIG. 24 depicts a linker utilized in a dendrimer conjugate in some embodiments of the present invention.

In some embodiments, a dendrimer conjugate of the present invention comprises a combination of one or more linkers. For example, in some embodiments, a dendrimer conjugate comprises a combination of two or more elimination linkers. In some embodiments, a dendrimer conjugate of the present invention comprises two or more cyclization linkers. In some embodiments, a dendrimer conjugate of the present invention comprises a one or more elimination linkers and one or more cyclization linkers, or a combination of one or more different types of linkers described herein. For example, in some embodiments, a dendrimer conjugate comprises a linker as shown in FIG. 24.

Figure 25:
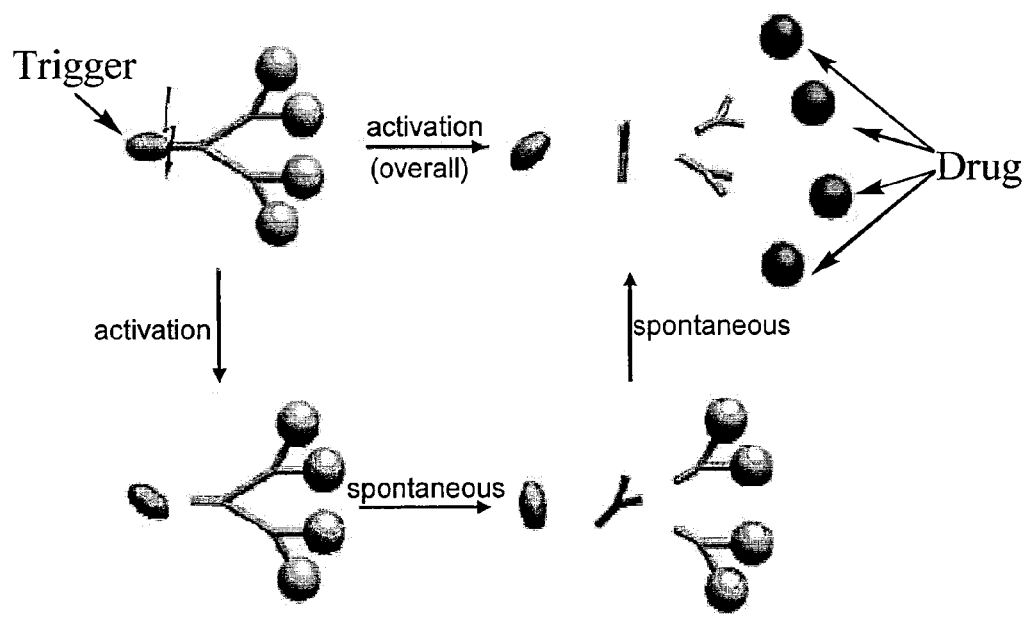
FIG. 25 shows branched self-elimination linkers utilized in a dendrimer conjugate in some embodiments of the present invention.

In some embodiments, a dendrimer conjugate of the present invention comprises branched self-elimination linkers (e.g., as shown in FIG. 25). Thus, in some embodiments, use of branched linkers provides a conjugate that can present increased concentrations of a therapeutic agent to a target site (e.g., inflammatory site, tumor site, etc.).

Figure 26:
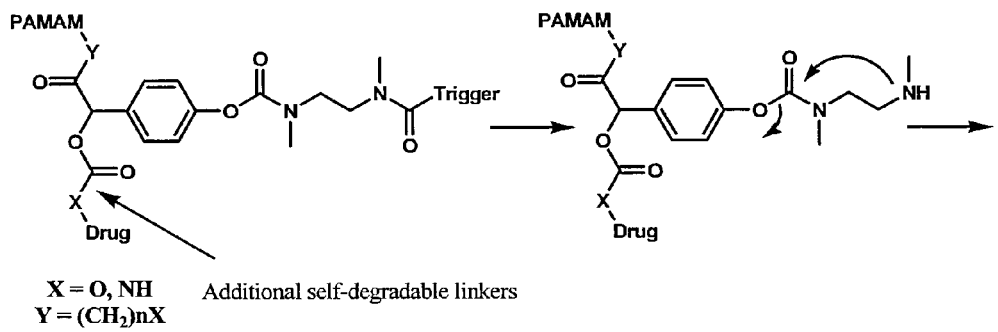
FIGS. 26A and B depicts dendrimer conjugates provided in some embodiments of the present invention.
Figure 26:
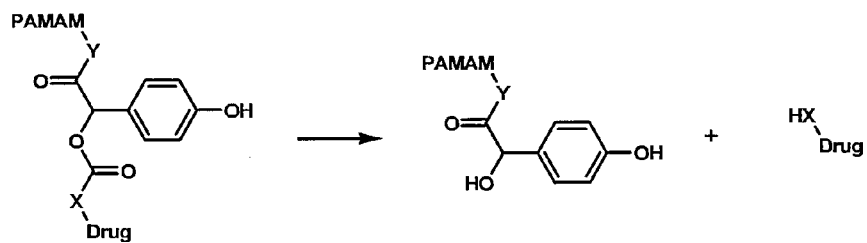
Figure 26:
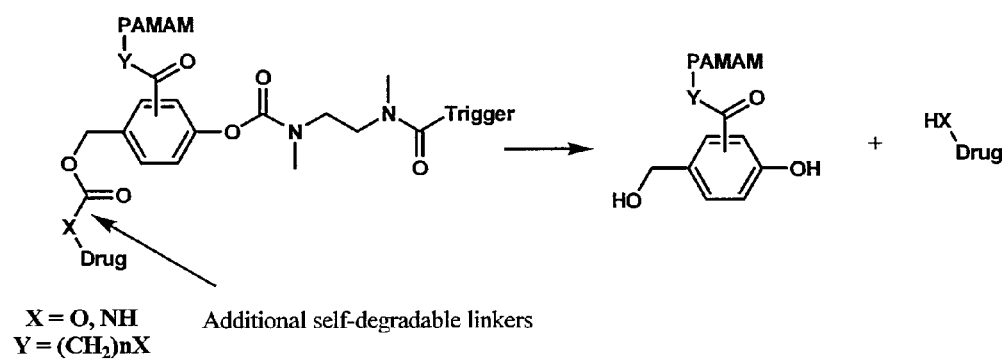

In some embodiments, a dendrimer conjugate of the present invention is generated by a process comprising conjugating a pre-formed tripartite piece (e.g., trigger, linker, and therapeutic agent) to a dendrimer (e.g., a G5 PAMAM dendrimer or other type of dendrimer described herein (e.g., conjugated to one or more different types of agents (e.g., imaging agent)). In some embodiments, linkage between a tripartite piece and a dendrimer comprises a non-cleavable bond (e.g., an ether or an amide bond (e.g., thereby decreasing unwanted activation of a trigger and/or degradation of a linker and/or release of therapeutic drug). In some embodiments, a linker (e.g., linear or other type of linker described herein) is utilized to attach a tripartite moiety (e.g., trigger, linker, and therapeutic agent) to a dendrimer (e.g., in order to increase drug release, decrease steric hindrance, and/or increase stability of the dendrimer). For example, in some embodiments, the present invention provides a dendrimer conjugate as shown in FIG. 26A-B.

Figure 27:
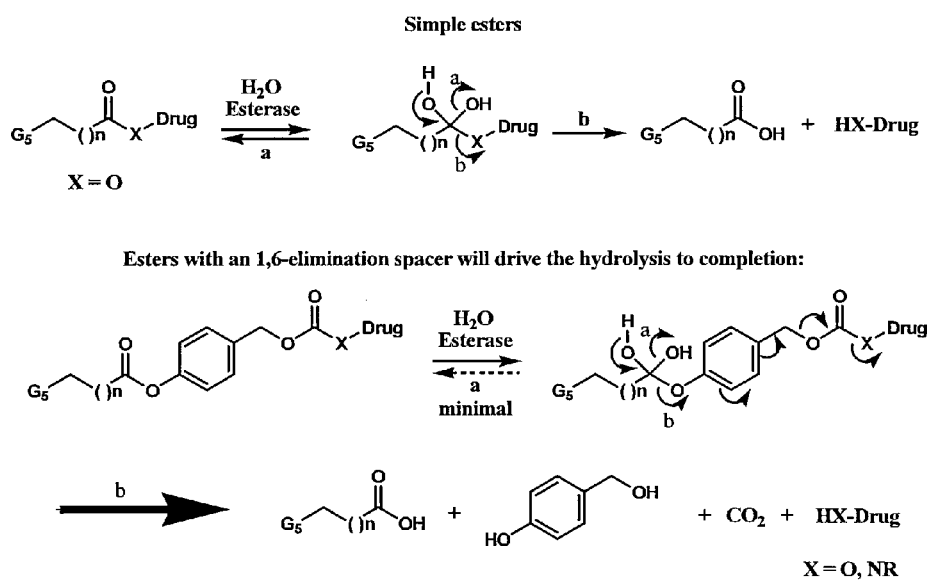
FIG. 27 shows a dendrimer comprising a simple ester (top portion of figure) and a dendrimer conjugate comprising an elimination linker (e.g., a 1, 6, elimination linker/spacer as shown in the bottom portion).

In some embodiments, a dendrimer conjugate of the present invention comprises a dendrimer conjugated to a linker (e.g., optionally conjugated to a trigger) that is conjugated to a therapeutic agent. In some embodiments, the dendrimer conjugate comprises a self-immolative connector between an ester bond (e.g., that is to be cleaved) and the therapeutic agent (e.g., thereby enhancing drug release). For example, although a mechanism is not necessary to practice the present invention and the present invention is not limited to any particular mechanism of action, in some embodiments, a dendrimer conjugate of the present invention comprising an ester linkage undergoes esterase catalyzed hydrolysis (e.g., as shown in FIG. 27 (e.g., G5 dendrimer comprising a self-degradable spacer and therapeutic agent)). Thus, in contrast to a dendrimer comprising a simple ester (e.g., a dendrimer in the top portion of FIG. 27 wherein therapeutic agent release may or may not occur, e.g., if x=NH), in some embodiments, the present invention provides a dendrimer conjugate comprising an elimination linker (e.g., a 1, 6, elimination linker/spacer as shown in the bottom portion of FIG. 27 (e.g., that permits complete hydrolysis of the linker (e.g., at a target site))).

Figure 28:
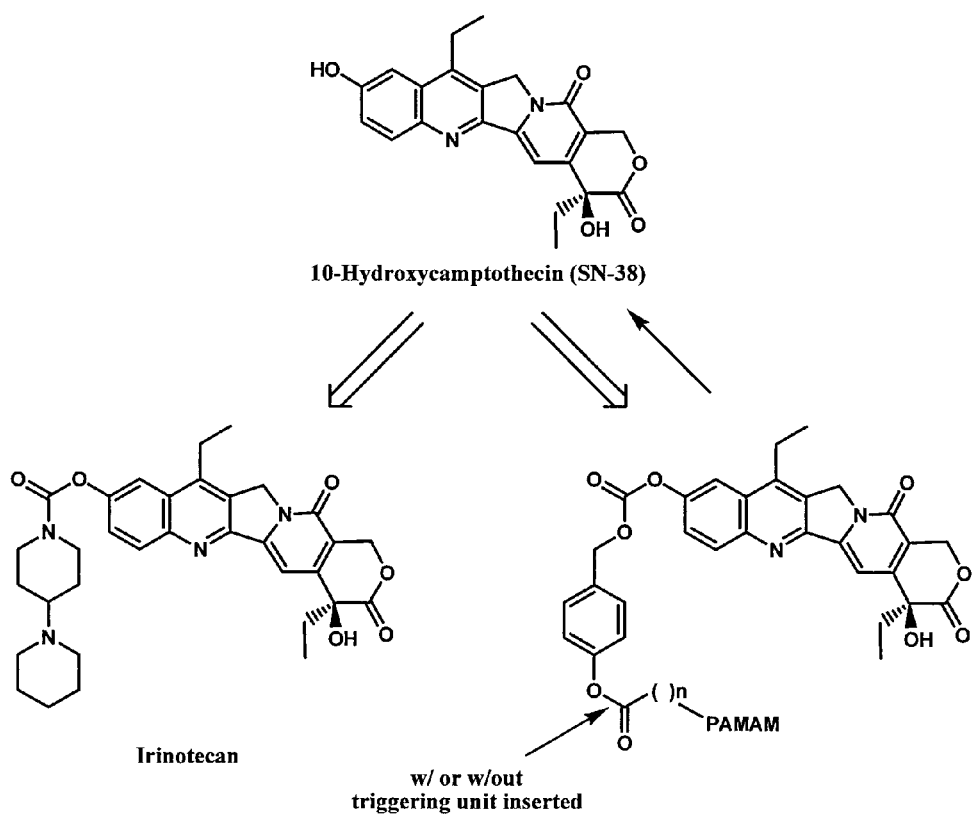
FIG. 28 shows a dendrimer conjugate comprising hydroxycamptothecin in some embodiments of the invention.

The present invention is not limited to any particular therapeutic agent that is part of a dendrimer conjugate comprising a linker as described herein. Indeed, a dendrimer conjugated comprising a linker may comprise nearly any therapeutic agent comprising a hydroxyl and/or amino group. In some embodiments, the therapeutic agent is an anti-cancer drug or agent. For example, in some embodiments, the therapeutic agent is doxorubicin (or an analog thereof) or paclitaxel (or an analog thereof). In some embodiments, a dendrimer conjugate of the invention comprises a therapeutic agent comprising a single reactive group (e.g., at a primary or secondary position). In some embodiments, a dendrimer conjugate of the present invention is synthesized utilizing a selective protection/deprotection strategy if multiple functional groups are present within a therapeutic agent. In some embodiments, a dendrimer conjugate of the present invention provides the ability to deliver a therapeutic agent that, when not in the context of the dendrimer conjugate (e.g., in the absence of conjugation to a dendrimer (e.g., a dendrimer comprising a linker and a trigger (e.g., configured to shield and/or mask the therapeutic drug and/or prohibit release of the therapeutic drug until the dendrimer reaches and reacts with a target site))) is toxic to a subject (e.g., that is too toxic to be utilized to treat a subject). Thus, in some embodiments, the present invention provides dendrimer conjugates comprising therapeutic agents that suffer from delivery issues and/or toxicity issues and/or non-specificity issues in the absence of being conjugated to a dendrimer conjugate. For example, in some embodiments, the present invention provides a dendrimer conjugate comprising a therapeutic agent comprising a compound of the camptothecin family (e.g., IRINOTECAN). IRINOTECAN is a prodrug of 10-hydroxycamptothecin (SN-38), which is 1000-fold more cytotoxic than IRINOTECAN. It has been reported that the conversion of irinotecan to hydroxycamptothecin has very low efficiency. Thus, in some embodiments, the present invention provides a dendrimer conjugate comprising hydroxycamptothecin (See, e.g., FIG. 28).

The present invention is not limited by the type of linker configuration. In some embodiments, the linker is conjugated via a free amino group via an amide linkage (e.g., formed from an active ester (e.g., the N-hydroxysuccinimide ester)). In some embodiments, an ester linkage remains in the conjugate after conjugation. In some embodiments, linkage occurs through a lysine residue. In some embodiments, conjugation occurs through a short-acting, degradable linkage. The present invention is not limited by the type of degradable linkage utilized. Indeed, a variety of linkages are contemplated to be useful in the present invention including, but not limited to, physiologically cleavable linkages including ester, carbonate ester, carbamate, sulfate, phosphate, acyloxyalkyl ether, acetal, and ketal linkages. In some embodiments, a dendrimer conjugate comprises a cleavable linkage present in the linkage between the dendrimer and linker and/or targeting agent and/or therapeutic agent present therein (e.g., such that when cleaved, no portion of the linkage remains on the dendrimer). In some embodiments, a dendrimer conjugate comprises a cleavable linkage present in the linker itself (e.g., such that when cleaved, a small portion of the linkage remains on the dendrimer).

The present invention is not limited to any particular targeting agent. In some embodiments, the targeting agent is a moiety that has affinity for a tumor associated factor. For example, a number of targeting agents are contemplated to be useful in the present invention including, but not limited to, RGD sequences, low-density lipoprotein sequences, a NAALADase inhibitor, epidermal growth factor, and other agents that bind with specificity to a target cell (e.g., a cancer cell)). In some embodiments, the targeting agent is an antibody, receptor ligand, hormone, vitamin, or antigen. However, the present invention is not limited by the nature of the targeting agent. In some embodiments, the antibody is specific for a disease-specific antigen. In some embodiments, the disease-specific antigen comprises a tumor-specific antigen. In some embodiments, the receptor ligand includes, but is not limited to, a ligand for CFTR, EGFR, estrogen receptor, FGR2, folate receptor, IL-2 receptor, glycoprotein, or VEGFR. In some embodiments, the receptor ligand is folic acid.

The present invention is not limited to cancer and/or tumor targeting agents. Indeed, dendrimers of the present invention can be targeted (e.g., via a linker conjugated to the dendrimer wherein the linker comprises a targeting agent) to a variety of target cells or tissues (e.g., to a biologically relevant environment) via conjugation to an appropriate targeting agent. For example, in some embodiments, the targeting agent is a moiety that has affinity for an inflammatory factor (e.g., a cytokine or a cytokine receptor moiety (e.g., TNF-α receptor)). In some embodiments, the targeting agent is a sugar, peptide, antibody or antibody fragment, hormone, hormone receptor, or the like.

In some embodiments of the present invention, the targeting agent includes, but is not limited to an antibody, receptor ligand, hormone, vitamin, and antigen, however, the present invention is not limited by the nature of the targeting agent. In some embodiments, the antibody is specific for a disease-specific antigen. In some embodiments, the disease-specific antigen comprises a tumor-specific antigen. In some embodiments, the receptor ligand includes, but is not limited to, a ligand for CFTR, EGFR, estrogen receptor, FGR2, folate receptor, IL-2 receptor, glycoprotein, and VEGFR. In some embodiments, the receptor ligand is folic acid.

The present invention also provides a method of treating a disease (e.g., cancer, inflammatory disease, chronic pain, autoimmune disease, etc.) comprising administering to a subject suffering from or susceptible to disease a therapeutically effective amount of a composition comprising a dendrimer conjugate (e.g., comprising a linker and/or trigger and a therapeutic agent) described herein. The present invention is not limited by the type of cancer treated using the compositions and methods of the present invention. Indeed, a variety of cancer can be treated including, but not limited to, prostate cancer, colon cancer, breast cancer, lung cancer and epithelial cancer. Similarly, the present invention is not limited by the type of inflammatory disease and/or chronic pain treated using the compositions of the present invention. Indeed, a variety of diseases can be treated including, but not limited to, arthritis (e.g., osteoarthritis, rheumatoid arthritis, etc.), inflammatory bowel disease (e.g., colitis, Chrohn's disease, etc.), autoimmune disease (e.g., lupus erythematosus, multiple sclerosis, etc.), inflammatory pelvic disease, etc.

In some embodiments, the present invention also provides a kit comprising a composition comprising dendrimer conjugate comprising a linker and/or trigger and a therapeutic agent. In some embodiments, the kit comprises a fluorescent agent or bioluminescent agent.

In some embodiments of the present invention, the therapeutic agent includes, but is not limited to, a chemotherapeutic agent, an anti-oncogenic agent, an anti-angiogenic agent, a tumor suppressor agent, an anti-microbial agent, or an expression construct comprising a nucleic acid encoding a therapeutic protein, although the present invention is not limited by the nature of the therapeutic agent. In further embodiments, the therapeutic agent is protected with a protecting group selected from photo-labile, radio-labile, and enzyme-labile protecting groups. In some embodiments, the chemotherapeutic agent is selected from a group consisting of, but not limited to, platinum complex, verapamil, podophylltoxin, carboplatin, procarbazine, mechloroethamine, cyclophosphamide, camptothecin, ifosfamide, melphalan, chlorambucil, bisulfan, nitrosurea, adriamycin, dactinomycin, daunorubicin, doxorubicin, bleomycin, plicomycin, mitomycin, bleomycin, etoposide, tamoxifen, paclitaxel, taxol, trans-platinum, 5-fluorouracil, vincristin, vinblastin, bisphosphonate (e.g., CB3717), chemotherapeutic agents with high affinity for folic acid receptors, ALIMTA (Eli Lilly), and methotrexate. In some embodiments, the anti-oncogenic agent comprises an antisense nucleic acid (e.g., RNA, molecule). In certain embodiments, the antisense nucleic acid comprises a sequence complementary to an RNA of an oncogene. In preferred embodiments, the oncogene includes, but is not limited to, abl, Bcl-2, Bcl-xL, erb, fms, gsp, hst, jun, myc, neu, raf; ras, ret, src, or trk. In some embodiments, the nucleic acid encoding a therapeutic protein encodes a factor including, but not limited to, a tumor suppressor, cytokine, receptor, inducer of apoptosis, or differentiating agent. In preferred embodiments, the tumor suppressor includes, but is not limited to, BRCA1, BRCA2, C-CAM, p16, p21, p53, p73, Rb, and p27. In preferred embodiments, the cytokine includes, but is not limited to, GMCSF, IL-1, IL-2, IL-3, IL-4, IL-5, IL-6, IL-7, IL-8, IL-9, IL-10, IL-11, IL-12, IL-13, IL-14, IL-15, β-interferon, γ-interferon, and TNF. In preferred embodiments, the receptor includes, but is not limited to, CFTR, EGFR, estrogen receptor, IL-2 receptor, and VEGFR. In preferred embodiments, the inducer of apoptosis includes, but is not limited to, AdE1B, Bad, Bak, Bax, Bid, Bik, Bim, Harakid, and ICE-CED3 protease. In some embodiments, the therapeutic agent comprises a short-half life radioisotope.

In some embodiments of the present invention, the biological monitoring agent comprises an agent that measures an effect of a therapeutic agent (e.g., directly or indirectly measures a cellular factor or reaction induced by a therapeutic agent), however, the present invention is not limited by the nature of the biological monitoring agent. In some embodiments, the monitoring agent is capable of detecting (e.g., measuring) apoptosis caused by the therapeutic agent.

In some embodiments of the present invention, the imaging agent comprises a radioactive label including, but not limited to $^{14}C$, $^{36}Cl$, $^{57}Co$, $^{58}Co$, $^{51}Cr$, $^{125}I$, $^{131}I$, $^{111}Ln$, $^{152}Eu$, $^{59}Fe$, $^{67}Ga$, $^{32}P$, $^{186}Re$, $^{35}S$, $^{75}Se$, Tc-99m, and $^{175}Yb$. In some embodiments, the imaging agent comprises a fluorescing entity. In a preferred embodiment, the imaging agent is fluorescein isothiocyanate or 6-TAMARA.

In some embodiments, dendrimer conjugates of the present invention are configured to treat disease. In preferred embodiments, dendrimer conjugates of the present invention are configured such that they are readily cleared from the subject (e.g., so that there is little to no detectable toxicity at efficacious doses). In some embodiments, the disease is a neoplastic disease, selected from, but not limited to, leukemia, acute leukemia, acute lymphocytic leukemia, acute myelocytic leukemia, myeloblastic, promyelocytic, myelomonocytic, monocytic, erythroleukemia, chronic leukemia, chronic myelocytic, (granulocytic) leukemia, chronic lymphocytic leukemia, Polycythemia vera, lymphoma, Hodgkin's disease, non-Hodgkin's disease, Multiple myeloma, Waldenstrom's macroglobulinemia, Heavy chain disease, solid tumors, sarcomas and carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, and neuroblastomaretinoblastoma. In some embodiments, the disease is an inflammatory disease selected from the group consisting of, but not limited to, eczema, inflammatory bowel disease, rheumatoid arthritis, asthma, psoriasis, ischemia/reperfusion injury, ulcerative colitis and acute respiratory distress syndrome. In some embodiments, the disease is a viral disease selected from the group consisting of, but not limited to, viral disease caused by hepatitis B, hepatitis C, rotavirus, human immunodeficiency virus type I (HIV-I), human immunodeficiency virus type II (HIV-II), human T-cell lymphotropic virus type I (HTLV-I), human T-cell lymphotropic virus type II (HTLV-II), AIDS, DNA viruses such as hepatitis type B and hepatitis type C virus; parvoviruses, such as adeno-associated virus and cytomegalovirus; papovaviruses such as papilloma virus, polyoma viruses, and SV40; adenoviruses; herpes viruses such as herpes simplex type I (HSV-I), herpes simplex type II (HSV-II), and Epstein-Barr virus; poxviruses, such as variola (smallpox) and vaccinia virus; and RNA viruses, such as human immunodeficiency virus type I (HIV-I), human immunodeficiency virus type II (HIV-II), human T-cell lymphotropic virus type I (HTLV-I), human T-cell lymphotropic virus type II (HTLV-II), influenza virus, measles virus, rabies virus, Sendai virus, picornaviruses such as poliomyelitis virus, coxsackieviruses, rhinoviruses, reoviruses, togaviruses such as rubella virus (German measles) and Semliki forest virus, arboviruses, and hepatitis type A virus.

The present invention is not limited by the type of therapeutic agent delivered via a dendrimer of the present invention. For example, a therapeutic may be any agent selected from the group comprising, but not limited to, a chemotherapeutic agent, an anti-oncogenic agent, an anti-angiogenic agent, a tumor suppressor agent, an anti-microbial agent, or an expression construct comprising a nucleic acid encoding a therapeutic protein. Illustrative examples of these types of agents are described herein.

The dendrimers of the present invention find use in the detection and treatment of a variety of cancers. Indeed, the present invention is not limited by the type of cancer to be treated. Thus, in some embodiments, the present invention provides compositions comprising dendrimer conjugates for the targeting and identification of angiogenesis associated with cancers (e.g., carcinomas). For example, in some embodiments, a dendrimer conjugate of the present invention further comprises a targeting agent (e.g., folic acid moiety) that associates with high affinity to a targeting agent ligand (e.g., receptor) on a cancer cell (e.g., carcinoma cells and/or solid tumor cells). In some embodiments, dendrimer conjugate and a targeting agent, that target and identify cancer cells and/or angiogenesis associated with cancer, further comprise a therapeutic agent that inhibits angiogenesis thereby treating the cancer. In some embodiments, treatment with dendrimers conjugates and an anti-angiogenic agent are used in combination with other dendrimers of the present invention, with other chemotherapeutic treatments, and/or as a treatment following surgical removal of a tumor or cancerous tissue. In some embodiments, a targeting moiety (e.g., folic acid or other targeting moiety described herein) posseses a high affinity for ligands (e.g., receptors or other types of proteins or molecules) present on cancer cell possessing such ligands thereby permitting the targeting, identification and treatment of disease (e.g., cancer) with little to no toxicity to surrounding healthy cells and tissue.

Dendrimer conjugates of the present invention are not limited by the type of anti-angiogenic agent used. Indeed, a variety of anti-angiogenic agents are contemplated to be useful in the compositions of the present invention including, but not limited to, Batimastat, Marimastat, AG3340, Neovastat, PEX, TIMP-1, -2, -3, -4, PAI-1, -2, uPA Ab, uPAR Ab, Amiloride, Minocycline, tetracyclines, steroids, cartilage-derived TIMP, αvβ3 Ab:LM609 and Vitaxin, RGD containing peptides, αvβ5 Ab, Endostatin, Angiostatin, aaAT, IFN-α, IFN-γ, IL-12, nitric oxide synthase inhibitors, TSP-1, TNP-470, Combretastatin A4, Thalidomide, Linomide, IFN-α, PF-4, prolactin fragment, Suramin and analogues, PPS, distamycin A analogues, FGF-2 Ab, antisense-FGF-2, Protamine, SU5416, soluble Flt-1, dominant-negative Flk-1, VEGF receptor ribosymes, VEGF Ab, Aspirin, NS-398, 6-AT, 6A5BU, 7-DX, Genistein, Lavendustin A, Ang-2, batimastat, marimastat, anti-αvβ3 monoclonal antibody (LM609) thrombospondin-1 (TSP-1) Angiostatin, endostatin, TNP-470, Combretastatin A-4, Anti-VEGF antibodies, soluble Flk-1, Flt-1 receptors, inhibitors of tyrosine kinase receptors, SU5416, heparin-binding growth factors, pentosan polysulfate, platelet-derived endothelial cell growth factor/Thymidine phosphorylase (PD-ECGF/TP), cox (e.g., cox-1 an cox-2) inhibitors (e.g., Celebrex and Vioxx), DT385, Tissue inhibitor of metalloprotease (TIMP-1, TIMP-2), Zinc, Plasminogen activator-inhibitor-1 (PAI-1), p53 Rb, Interleukin-10 Interleukin-12, Angiopoietin-2, Angiotensin, Angiotensin II (AT2 receptor), Caveolin-1, caveolin-2, Angiopoietin-2, Angiotensin, Angiotensin II (AT2 receptor), Caveolin-1, caveolin-2, Endostatin, Interferon-alpha, Isoflavones, Platelet factor-4, Prolactin (16 Kd fragment), Thrombospondin, Troponin-1, Bay 12-9566, AG3340, CGS 27023A, CGS 27023A, COL-3, (Neovastat), BMS-275291, Penicillamine, TNP-470 (fumagillin derivative), Squalamine, Combretastatin, Endostatin, Penicillamine, Farnesyl Transferase Inhibitor (FTI), -L-778,123, -SCH66336, -R115777, anti-VEGF antibody, Thalidomide, SU5416, Ribozyme, Angiozyme, SU6668, PTK787/ZK22584, Interferon-alpha, Interferon-alpha, Suramin, Vitaxin, EMD121974, Penicillamine, Tetrathiomolybdate, Captopril, serine protease inhibitors, CAI, ABT-627, CM101/ZDO101, Interleukin-12, IM862, PNU-145156E, those described in U.S. Patent App. No. 20050123605, herein incorporated by reference in its entirety, and fragments or portions of the above that retain anti-angiogenic (e.g., angiostatic or inhibitory properties).

In some embodiments, dendrimer conjugates and methods of using the same of the present invention are used in treatment and/or monitoring during cancer therapy. However, the systems and compositions of the present invention find use in the treatment and monitoring of a variety of disease states or other physiological conditions, and the present invention is not limited to use with any particular disease state or condition. Other disease states that find particular use with the present invention include, but are not limited to, cardiovascular disease, viral disease, inflammatory disease, and proliferative disorders.

In some embodiments, the present invention provides a dendrimer conjugate comprising a linker and/or trigger and a therapeutic agent that is acetylated (e.g., partially acetylated). In other embodiments, the present invention provides methods of manufacturing a dendrimer conjugate as described herein (e.g., in Examples 1-7).

Some embodiments of the present invention provide compositions comprising dendrimer conjugates further comprising one or more functional groups, the functional groups including, but not limited to, therapeutic agents, biological monitoring components, biological imaging components, targeting components, and components to identify the specific signature of cellular abnormalities. As such, in some embodiments, a therapeutic dendrimer conjugate of the present invention is made up of individual dendrimers, each with one or more functional groups being specifically conjugated with or covalently linked to the dendrimer.

The following discussion describes individual component parts of the dendrimer and methods of making and using the same in some embodiments of the present invention. To illustrate the design and use of the systems and compositions of the present invention, the discussion focuses on specific embodiments of the use of the compositions in the treatment and monitoring of cancer. These specific embodiments are intended only to illustrate certain preferred embodiments of the present invention and are not intended to limit the scope thereof.

In some embodiments, the release of a therapeutic agent is facilitated by the therapeutic component being attached to a labile protecting group, such as, for example, cisplatin or methotrexate being attached to a photolabile protecting group that becomes released by laser light directed at cells emitting a color of fluorescence (e.g., in addition to and/or in place of target activated activation of a trigger component of a dendrimer conjugate). In some embodiments, the therapeutic device also may have a component to monitor the response of the tumor to therapy. For example, where a therapeutic agent of the dendrimer induces apoptosis of a target cell (e.g., a cancer cell (e.g., a prostate cancer cell)), the caspase activity of the cells may be used to activate a green fluorescence. This allows apoptotic cells to turn orange, (combination of red and green) while residual cells remain red. Any normal cells that are induced to undergo apoptosis in collateral damage fluoresce green.

As is clear from the above example, the use of the compositions of the present invention facilitates non-intrusive sensing, signaling, and intervention for cancer and other diseases and conditions. Since specific protocols of molecular alterations in cancer cells are identified using this technique, non-intrusive sensing through the dendrimers is achieved and may then be employed automatically against various tumor phenotypes.

I. Dendrimers

In some embodiments, compositions of the present invention comprise dendrimers wherein the dendrimers. Dendrimeric polymers have been described extensively (See, e.g., Tomalia, Advanced Materials 6:529 (1994); Angew, Chem. Int. Ed. Engl., 29:138 (1990); incorporated herein by reference in their entireties). Dendrimer polymers are synthesized as defined spherical structures typically ranging from 1 to 20 nanometers in diameter. Methods for manufactureing a G5 PAMAM dendrimer with a protected core is shown (FIGS. 1-5). In preferred embodiments, the protected core diamine is NH2-CH2-CH2-NHPG. Molecular weight and the number of terminal groups increase exponentially as a function of generation (the number of layers) of the polymer (See, e.g., FIG. 9). Different types of dendrimers can be synthesized based on the core structure that initiates the polymerization process (See e.g., FIGS. 1-5).

The dendrimer core structures dictate several characteristics of the molecule such as the overall shape, density and surface functionality (See, e.g., Tomalia et al., Chem. Int. Ed. Engl., 29:5305 (1990)). Spherical dendrimers can have ammonia as a trivalent initiator core or ethylenediamine (EDA) as a tetravalent initiator core (See, e.g., FIG. 9). Recently described rod-shaped dendrimers (See, e.g., Yin et al., J. Am. Chem. Soc., 120:2678 (1998)) use polyethyleneimine linear cores of varying lengths; the longer the core, the longer the rod. Dendritic macromolecules are available commercially in kilogram quantities and are produced under current good manufacturing processes (GMP) for biotechnology applications.

Figure 10:
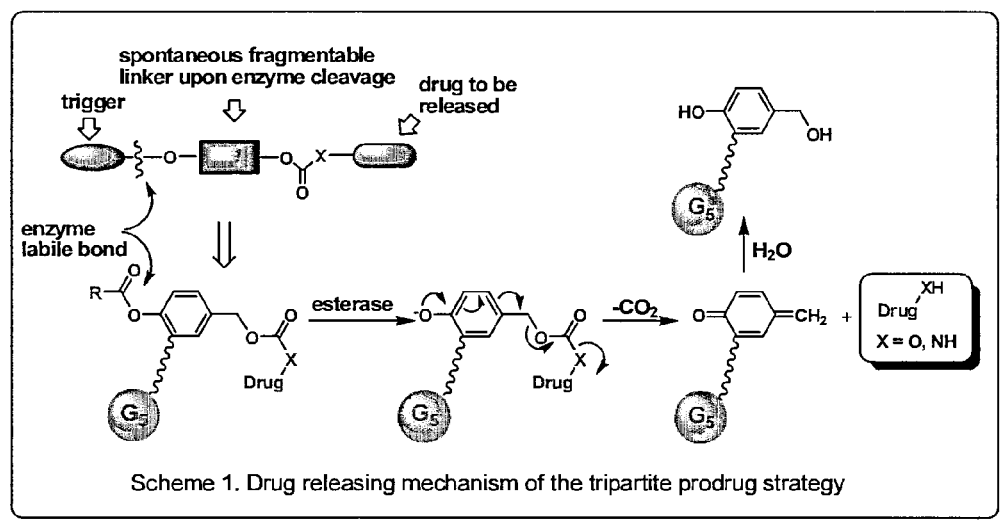
FIG. 10 shows the release of a therapeutic compound from esterase sensitive linker-dendrimer conjugate in one embodiment of the invention.
Figure 13:
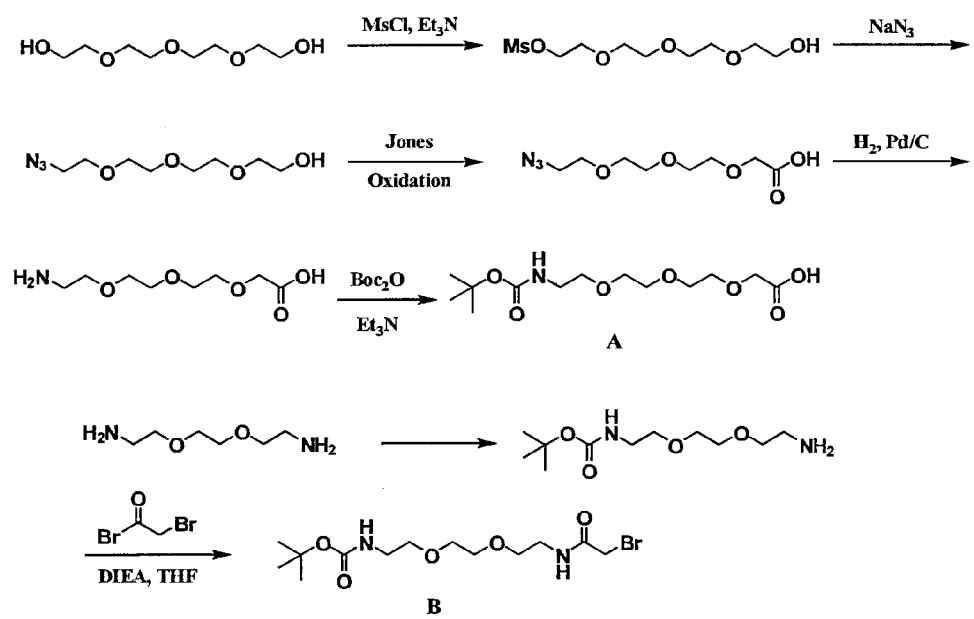
FIG. 13 shows dendrimer conjugate and methods of synthesizing the same in some embodiments of the invention.
Figure 14:
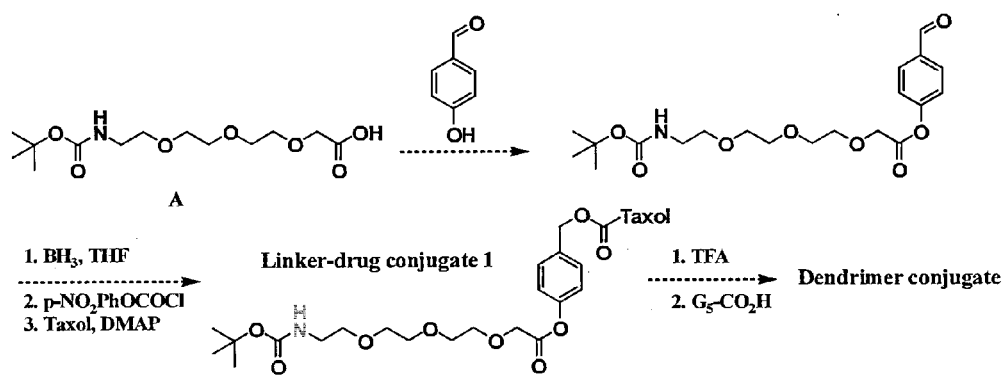
FIG. 14 shows a diagram of a dendrimer conjugate provided in some embodiments of the present invention.
Figure 17:
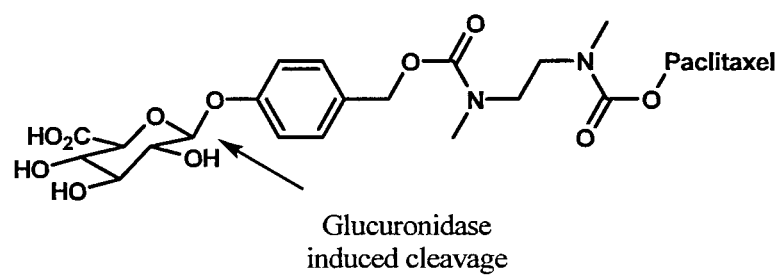
FIG. 17 shows an example of a dendrimer conjugate designed for glucuronidase triggered cleavage in one embodiment of the present invention.

Dendrimers may be characterized by a number of techniques including, but not limited to, electrospray-ionization mass spectroscopy, $^{13}$C nuclear magnetic resonance spectroscopy, $^1$H nuclear magnetic resonance spectroscopy (See, e.g., Example 5, FIG. 10(A) and Example 7, FIG. 14), high performance liquid chromatography (See, e.g., Example 5, FIG. 10(B); and Example 6, FIG. 13), size exclusion chromatography with multi-angle laser light scattering (See, e.g., Example 4, FIG. 8), ultraviolet spectrophotometry (See, e.g., Example 8, FIG. 17), capillary electrophoresis and gel electrophoresis. These tests assure the uniformity of the polymer population and are important for monitoring quality control of dendrimer manufacture for GMP applications and in vivo usage.

Numerous U.S. Patents describe methods and compositions for producing dendrimers. Examples of some of these patents are given below in order to provide a description of some dendrimer compositions that may be useful in the present invention, however it should be understood that these are merely illustrative examples and numerous other similar dendrimer compositions could be used in the present invention.

U.S. Pat. No. 4,507,466, U.S. Pat. No. 4,558,120, U.S. Pat. No. 4,568,737, and U.S. Pat. No. 4,587,329 each describe methods of making dense star polymers with terminal densities greater than conventional star polymers. These polymers have greater/more uniform reactivity than conventional star polymers, i.e. 3rd generation dense star polymers. These patents further describe the nature of the amidoamine dendrimers and the 3-dimensional molecular diameter of the dendrimers.

U.S. Pat. No. 4,631,337 describes hydrolytically stable polymers. U.S. Pat. No. 4,694,064 describes rod-shaped dendrimers. U.S. Pat. No. 4,713,975 describes dense star polymers and their use to characterize surfaces of viruses, bacteria and proteins including enzymes. Bridged dense star polymers are described in U.S. Pat. No. 4,737,550. U.S. Pat. No. 4,857,599 and U.S. Pat. No. 4,871,779 describe dense star polymers on immobilized cores useful as ion-exchange resins, chelation resins and methods of making such polymers.

U.S. Pat. No. 5,338,532 is directed to starburst conjugates of dendrimer(s) in association with at least one unit of carried agricultural, pharmaceutical or other material. This patent describes the use of dendrimers to provide means of delivery of high concentrations of carried materials per unit polymer, controlled delivery, targeted delivery and/or multiple species such as e.g., drugs antibiotics, general and specific toxins, metal ions, radionuclides, signal generators, antibodies, interleukins, hormones, interferons, viruses, viral fragments, pesticides, and antimicrobials.

U.S. Pat. No. 6,471,968 describes a dendrimer complex comprising covalently linked first and second dendrimers, with the first dendrimer comprising a first agent and the second dendrimer comprising a second agent, wherein the first dendrimer is different from the second dendrimer, and where the first agent is different than the second agent.

Other useful dendrimer type compositions are described in U.S. Pat. No. 5,387,617, U.S. Pat. No. 5,393,797, and U.S. Pat. No. 5,393,795 in which dense star polymers are modified by capping with a hydrophobic group capable of providing a hydrophobic outer shell. U.S. Pat. No. 5,527,524 discloses the use of amino terminated dendrimers in antibody conjugates.

The use of dendrimers as metal ion carriers is described in U.S. Pat. No. 5,560,929. U.S. Pat. No. 5,773,527 discloses non-crosslinked polybranched polymers having a comb-burst configuration and methods of making the same. U.S. Pat. No. 5,631,329 describes a process to produce polybranched polymer of high molecular weight by forming a first set of branched polymers protected from branching; grafting to a core; deprotecting first set branched polymer, then forming a second set of branched polymers protected from branching and grafting to the core having the first set of branched polymers, etc.

U.S. Pat. No. 5,902,863 describes dendrimer networks containing lipophilic organosilicone and hydrophilic polyanicloamine nanscopic domains. The networks are prepared from copolydendrimer precursors having PAMAM (hydrophilic) or polyproyleneimine interiors and organosilicon outer layers. These dendrimers have a controllable size, shape and spatial distribution. They are hydrophobic dendrimers with an organosilicon outer layer that can be used for specialty membrane, protective coating, composites containing organic organometallic or inorganic additives, skin patch delivery, absorbants, chromatography personal care products and agricultural products.

U.S. Pat. No. 5,795,582 describes the use of dendrimers as adjuvants for influenza antigen. Use of the dendrimers produces antibody titer levels with reduced antigen dose. U.S. Pat. No. 5,898,005 and U.S. Pat. No. 5,861,319 describe specific immunobinding assays for determining concentration of an analyte. U.S. Pat. No. 5,661,025 provides details of a self-assembling polynucleotide delivery system comprising dendrimer polycation to aid in delivery of nucleotides to target site. This patent provides methods of introducing a polynucleotide into a eukaryotic cell in vitro comprising contacting the cell with a composition comprising a polynucleotide and a dendrimer polyeation non-covalently coupled to the polynucleotide.

Dendrimer-antibody conjugates for use in in vitro diagnostic applications has previously been demonstrated (See, e.g., Singh et al., Clin. Chem., 40:1845 (1994)), for the production of dendrimer-chelant-antibody constructs, and for the development of boronated dendrimer-antibody conjugates (for neutron capture therapy); each of these latter compounds may be used as a cancer therapeutic (See, e.g., Wu et al., Bioorg. Med. Chem. Lett., 4:449 (1994); Wiener et al., Magn. Reson. Med. 31:1 (1994); Barth et al., Bioconjugate Chem. 5:58 (1994); and Barth et al.).

Some of these conjugates have also been employed in the magnetic resonance imaging of tumors (See, e.g., Wu et al., (1994) and Wiener et al., (1994), supra). Results from this work have documented that, when administered in vivo, antibodies can direct dendrimer-associated therapeutic agents to antigen-bearing tumors. Dendrimers also have been shown to specifically enter cells and carry either chemotherapeutic agents or genetic therapeutics. In particular, studies show that cisplatin encapsulated in dendrimer polymers has increased efficacy and is less toxic than cisplatin delivered by other means (See, e.g., Duncan and Malik, Control Rel. Bioact. Mater. 23:105 (1996)).

Dendrimers have also been conjugated to fluorochromes or molecular beacons and shown to enter cells. They can then be detected within the cell in a manner compatible with sensing apparatus for evaluation of physiologic changes within cells (See, e.g., Baker et al., Anal. Chem. 69:990 (1997)). Finally, dendrimers have been constructed as differentiated block copolymers where the outer portions of the molecule may be digested with either enzyme or light-induced catalysis (See, e.g., Urdea and Horn, Science 261:534 (1993)). This allows the controlled degradation of the polymer to release therapeutics at the disease site and provides a mechanism for an external trigger to release the therapeutic agents.

II. Therapeutic Agents

A wide range of therapeutic agents find use with the present invention. Any therapeutic agent that can be associated with a dendrimer and/or linker described herein may be delivered using the methods, systems, and compositions of the present invention. For example, in some embodiments the therapeutic agent is Naloxone and/or a Naloxone pro-drug.

To illustrate delivery of therapeutic agents, the following discussion focuses mainly on the delivery of methotrexate, cisplatin and taxol for the treatment of cancer. Also discussed are various photodynamic therapy compounds. However, the present invention is not limited to solely to the use of these exemplary agents. Indeed, a wide variety of agents (e.g., therapeutic agents) find use with the dendrimers of the present invention (e.g., as described herein).

i. Methotrexate, Cisplatin and Taxol

The cytotoxicity of methotrexate depends on the duration for which a threshold intracellular level is maintained (Levasseur et al., Cancer Res 58, 5749 (1998); Goldman & Matherly, Pharmacol Ther 28, 77 (1985)). Cells contain high concentrations of DHFR, and, to shut off the DHFR activity completely, anti-folate levels six orders of magnitude higher than the Ki for DHFR is required (Sierrra & Goldman, Seminars in Oncology 26, 11 (1999)). Furthermore, less than 5% of the enzyme activity is sufficient for full cellular enzymatic function (White & Goldman, Biol Chem 256, 5722 (1981)). Cisplatin and Taxol have a well-defined action of inducing apoptosis in tumor cells (See e.g., Lanni et al., Proc. Natl. Acad. Sci., 94:9679 (1997); Tortora et al., Cancer Research 57:5107 (1997); and Zaffaroni et al., Brit. J. Cancer 77:1378 (1998)). However, treatment with these and other chemotherapeutic agents is difficult to accomplish without incurring significant toxicity. The agents currently in use are generally poorly water soluble, quite toxic, and given at doses that affect normal cells as wells as diseased cells. For example, paclitaxel (Taxol), one of the most promising anticancer compounds discovered, is poorly soluble in water.

Paclitaxel has shown excellent antitumor activity in a wide variety of tumor models such as the B16 melanoma, L1210 leukemias, MX-1 mammary tumors, and CS-1 colon tumor xenografts. However, the poor aqueous solubility of paclitaxel presents a problem for human administration. Accordingly, currently used paclitaxel formulations require a cremaphor to solubilize the drug. The human clinical dose range is 200-500 mg. This dose is dissolved in a 1:1 solution of ethanol:cremaphor and diluted to one liter of fluid given intravenously. The cremaphor currently used is polyethoxylated castor oil. It is given by infusion by dissolving in the cremaphor mixture and diluting with large volumes of an aqueous vehicle. Direct administration (e.g., subcutaneous) results in local toxicity and low levels of activity. Thus, there is a need for more efficient and effective delivery systems for these chemotherapeutic agents.

The present invention overcomes these problems by providing methods and compositions for specific drug delivery. The present invention also provides the ability to administer combinations of agents (e.g., two or more different therapeutic agents) to produce an additive effect. The use of multiple agent may be used to counter disease resistance to any single agent. For example, resistance of some cancers to single drugs (taxol) has been reported (Yu et al., Molecular Cell.

2:581 (1998)). In some embodiments, the present invention provides a dendrimer conjugate comprising a linker conjugated to a chemotherapeutic agent (e.g., the therapeutic agent methotrexate). In some embodiments, a dendrimer conjugate comprising a linker conjugated to methotrexate is used to target and treat (e.g., kill) cancer cells (e.g., prostate cancer cells) within a subject. The present invention is contemplated to be useful for treating a subject with any stage of cancer (e.g., prostate cancer). In some embodiments, compositions of the present invention can be used prophylactically.

The present invention also provides the opportunity to monitor therapeutic success following delivery of a therapeutic agent (e.g., methotrexate, cisplatin and/or Taxol) to a subject. For example, measuring the ability of these drugs to induce apoptosis in vitro is reported to be a marker for in vivo efficacy (See, e.g., Gibb, Gynecologic Oncology 65:13 (1997)). Therefore, in addition to the targeted delivery of a therapeutic agent (e.g., either one, two or all of the above mentioned drugs) to provide effective anti-tumor therapy and reduction of toxicity, the effectiveness of the therapy can be gauged by a biological monitoring agent of the present invention (e.g., that monitor the induction of apoptosis). It is contemplated that dendrimer conjugates comprising a therapeutic agent and/or imaging agents and/or biological imaging agents are active against a wide-range of tumor types including, but not limited to, prostate cancer, breast cancer, colon cancer, lung cancer, epithelial cancer, etc.

Although the above discussion describes the specific therapeutic agents methotrexate, cisplatin and Taxol, any pharmaceutical that is routinely used in a cancer therapy context finds use in the present invention. In treating cancer according to the invention, the therapeutic component of the dendrimer may comprise compounds including, but not limited to, adriamycin, 5-fluorouracil, etoposide, camptothecin, actinomycin-D, mitomycin C, or more preferably, cisplatin. The agent may be prepared and used as a combined therapeutic composition, or kit, by combining it with an immunotherapeutic agent, as described herein.

In some embodiments of the present invention, a dendrimer conjugate comprising linker is contemplated to comprise (e.g., be conjugated to via a linker) one or more agents that directly cross-link nucleic acids (e.g., DNA) to facilitate DNA damage leading to a synergistic, antineoplastic agents of the present invention. Agents such as cisplatin, and other DNA alkylating agents may be used. Cisplatin has been widely used to treat cancer, with efficacious doses used in clinical applications of 20 mg/$M^2$ for 5 days every three weeks for a total of three courses. The dendrimers may be delivered via any suitable method, including, but not limited to, injection intravenously, subcutaneously, intratumorally, intraperitoneally, or topically (e.g., to mucosal surfaces).

Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25-75 Mg/$M^2$ at 21 day intervals for adriamycin, to 35-50 Mg/$M^2$ for etoposide intravenously or double the intravenous dose orally.

Agents that disrupt the synthesis and fidelity of nucleic acid precursors and subunits also lead to DNA damage and find use as chemotherapeutic agents in the present invention. A number of nucleic acid precursors have been developed. Particularly useful are agents that have undergone extensive testing and are readily available. As such, agents such as 5-fluorouracil (5-FU) are preferentially used by neoplastic tissue, making this agent particularly useful for targeting to neoplastic cells. The doses delivered may range from 3 to 15 mg/kg/day, although other doses may vary considerably according to various factors including stage of disease, amenability of the cells to the therapy, amount of resistance to the agents and the like.

The anti-cancer therapeutic agents that find use in the present invention are those that are amenable to incorporation into dendrimer structures or are otherwise associated with dendrimer structures such that they can be delivered into a subject, tissue, or cell without loss of fidelity of its anticancer effect. For a more detailed description of cancer therapeutic agents such as a platinum complex, verapamil, podophyllotoxin, carboplatin, procarbazine, mechlorethamine, cyclophosphamide, camptothecin, ifosfamide, melphalan, chlorambucil, bisulfan, nitrosurea, adriamycin, dactinomycin, daunorubicin, doxorubicin, bleomycin, plicomycin, mitomycin, etoposide (VP16), tamoxifen, taxol, transplatinum, 5-fluorouracil, vincristin, vinblastin and methotrexate and other similar anti-cancer agents, those of skill in the art are referred to any number of instructive manuals including, but not limited to, the Physician's Desk reference and to Goodman and Gilman's "Pharmaceutical Basis of Therapeutics" ninth edition, Eds. Hardman et al., 1996.

In some embodiments, the drugs are preferably attached to the dendrimers and/or linkers conjugated to the dendrimers with photocleavable linkers. For example, several heterobifunctional, photocleavable linkers that find use with the present invention are described by Ottl et al. (Ottl et al., Bioconjugate Chem., 9:143 (1998)). These linkers can be either water or organic soluble. They contain an activated ester that can react with amines or alcohols and an epoxide that can react with a thiol group. In between the two groups is a 3,4-dimethoxy6-nitrophenyl photoisomerization group, which, when exposed to near-ultraviolet light (365 nm), releases the amine or alcohol in intact form. Thus, the therapeutic agent, when linked to the compositions of the present invention using such linkers, may be released in biologically active or activatable form through exposure of the target area to near-ultraviolet light.

In some embodiments, methotrexate is conjugated to a dendrimer and/or to a linker conjugated to a dendrimer via an ester bond. In an exemplary embodiment, the alcohol group of taxol is reacted with the activated ester of the organic-soluble linker. This product in turn is reacted with the partially-thiolated surface of appropriate dendrimers (the primary amines of the dendrimers can be partially converted to thiol-containing groups by reaction with a sub-stoichiometric amount of 2-iminothiolano). In the case of cisplatin, the amino groups of the drug are reacted with the water-soluble form of the linker. If the amino groups are not reactive enough, a primary amino-containing active analog of cisplatin, such as Pt(II) sulfadiazine dichloride (Pasani et al., Inorg. Chim. Acta 80:99 (1983) and Abel et al, Eur. J. Cancer 9:4 (1973)) can be used. Thus conjugated, the drug is inactive and will not harm normal cells. When the conjugate is localized within tumor cells, it is exposed to laser light of the appropriate near-UV wavelength, causing the active drug to be released into the cell.

Similarly, in other embodiments of the present invention, the amino groups of cisplatin (or an analog thereof) is linked with a very hydrophobic photocleavable protecting group, such as the 2-nitrobenzyloxycarbonyl group (Pillai, V. N. R. Synthesis: 1-26 (1980)). With this hydrophobic group attached, the drug is loaded into and very preferentially retained by the hydrophobic cavities within the PAMAM dendrimer (See e.g., Esfand et al., Pharm. Sci., 2:157 (1996)), insulated from the aqueous environment. When exposed to near-LV light (about 365 nm), the hydrophobic group is cleaved, leaving the intact drug. Since the drug itself is hydrophilic, it diffuses out of the dendrimer and into the tumor cell, where it initiates apoptosis.

An alternative to photocleavable linkers are enzyme cleavable linkers. A number of photocleavable linkers have been demonstrated as effective anti-tumor conjugates and can be prepared by attaching cancer therapeutics, such as doxorubicin, to water-soluble polymers with appropriate short peptide linkers (See e.g., Vasey et al., Clin. Cancer Res., 5:83 (1999)). The linkers are stable outside of the cell, but are cleaved by thiolproteases once within the cell. In some embodiments, the conjugate PK1 is used. As an alternative to the photocleavable linker strategy, enzyme-degradable linkers, such as Gly-Phe-Leu-Gly may be used.

The present invention is not limited by the nature of the therapeutic technique. For example, other conjugates that find use with the present invention include, but are not limited to, using conjugated boron clusters for BNCT (Capala et al., Bioconjugate Chem., 7:7 (1996)), the use of radioisotopes, and conjugation of toxins such as ricin to the dendrimer conjugate.

ii. Photodynamic Therapy

Photodynamic therapeutic agents may also be used as therapeutic agents in the present invention. In some embodiments, the dendrimer conjugates of the present invention containing photodynamic compounds are illuminated, resulting in the production of singlet oxygen and free radicals that diffuse out of the fiberless radiative effector to act on the biological target (e.g., tumor cells or bacterial cells). Some preferred photodynamic compounds include, but are not limited to, those that can participate in a type H photochemical reaction:

$PS + h\nu \rightarrow PS^*(1)$

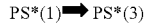

$PS^*(1) \rightarrow PS^*(3)$

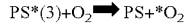

$PS^*(3) + O_2 \rightarrow PS + {}^*O_2$

${}^*O_2 + T \rightarrow$ cytotoxity where PS=photosenstizer, PS*(1)=excited singlet state of PS, PS*(3)=excited triplet state of PS, hv=light quantum, *O$_2$=excited singlet state of oxygen, and T=biological target. Other photodynamic compounds useful in the present invention include those that cause cytotoxity by a different mechanism than singlet oxygen production (e.g., copper benzochlorin, Selman, et al., Photochem. Photobiol., 57:681-85 (1993), incorporated herein by reference). Examples of photodynamic compounds that find use in the present invention include, but are not limited to Photofrin 2, phtalocyanins (See e.g., Brasseur et al., Photochem. Photobiol., 47:705-11 (1988)), benzoporphyrin, tetrahydroxyphenylporphyrins, naphtalocyanines (See e.g., Firey and Rodgers, Photochem. Photobiol., 45:535-38 (1987)), sapphyrins (See, e.g., Sessler et al., Proc. SPIE, 1426:318-29 (1991)), porphinones (See, e.g., Chang et al., Proc. SPIE, 1203:281-86 (1990)), tin etiopurpurin, ether substituted porphyrins (See, e.g., Pandey et al., Photochem. Photobiol., 53:65-72 (1991)), and cationic dyes such as the phenoxazines (See e.g., Cincotta et al., SPIE Proc., 1203:202-10 (1990)).

III. Signature Identifying Agents

In some embodiments, dendrimer conjugates of the present invention contain one or more signature identifying agents that are activated by, or are able to interact with, a signature component ("signature"). In preferred embodiments, the signature identifying agent is an antibody, preferably a monoclonal antibody, that specifically binds the signature (e.g., cell surface molecule specific to a cell to be targeted).

In some embodiments of the present invention, tumor cells are identified. Tumor cells have a wide variety of signatures, including the defined expression of cancer-specific antigens such as Mucl, HER-2 and mutated p53 in breast cancer. These act as specific signatures for the cancer, being present in 30% (HER-2) to 70% (mutated p53) of breast cancers. In some embodiments, a dendrimer of the present invention comprises a monoclonal antibody that specifically binds to a mutated version of p53 that is present in breast cancer. In some embodiments, a dendrimer of the present invention comprises an antibody (e.g., monoclonal antibody) with high affinity for a signature including, but not limited to, Mucl and HER-2.

In some embodiments of the present invention, cancer cells expressing susceptibility genes are identified. For example, in some embodiments, there are two breast cancer susceptibility genes that are used as specific signatures for breast cancer: BRCA1 on chromosome 17 and BRCA2 on chromosome 13. When an individual carries a mutation in either BRCA1 or BRCA2, they are at an increased risk of being diagnosed with breast or ovarian cancer at some point in their lives. These genes participate in repairing radiation-induced breaks in double-stranded DNA. It is thought that mutations in BRCA1 or BRCA2 might disable this mechanism, leading to more errors in DNA replication and ultimately to cancerous growth.

In addition, the expression of a number of different cell surface receptors find use as targets for the binding and uptake of a dendrimer conjugate. Such receptors include, but are not limited to, EGF receptor, folate receptor, FGR receptor 2, and the like.

In some embodiments of the present invention, changes in gene expression associated with chromosomal abborations are the signature component. For example, Burkitt lymphoma results from chromosome translocations that involve the Myc gene. A chromosome translocation means that a chromosome is broken, which allows it to associate with parts of other chromosomes. The classic chromosome translocation in Burkitt lymophoma involves chromosome 8, the site of the Myc gene. This changes the pattern of Myc expression, thereby disrupting its usual function in controlling cell growth and proliferation.

In other embodiments, gene expression associated with colon cancer are identified as the signature component. Two key genes are known to be involved in colon cancer: MSH2 on chromosome 2 and MLH1 on chromosome 3. Normally, the protein products of these genes help to repair mistakes made in DNA replication. If the MSH2 and MLH1 proteins are mutated, the mistakes in replication remain unrepaired, leading to damaged DNA and colon cancer. MEN1 gene, involved in multiple endocrine neoplasia, has been known for several years to be found on chromosome 11, was more finely mapped in 1997, and serves as a signature for such cancers. In preferred embodiments of the present invention, an antibody specific for the altered protein or for the expressed gene to be detected is complexed with nanodevices of the present invention.

In yet another embodiment, adenocarcinoma of the colon has defined expression of CEA and mutated p53, both well-documented tumor signatures. The mutations of p53 in some of these cell lines are similar to that observed in some of the breast cancer cells and allows for the sharing of a p53 sensing component between the two nanodevices for each of these cancers (i.e., in assembling the nanodevice, dendrimers comprising the same signature identifying agent may be used for each cancer type). Both colon and breast cancer cells may be reliably studied using cell lines to produce tumors in nude mice, allowing for optimization and characterization in animals.

From the discussion above it is clear that there are many different tumor signatures that find use with the present invention, some of which are specific to a particular type of cancer and others which are promiscuous in their origin. The present invention is not limited to any particular tumor signature or any other disease-specific signature. For example, tumor suppressors that find use as signatures in the present invention include, but are not limited to, p53, Mucl, CEA, p16, p21, p27, CCAM, RB, APC, DCC, NF-1, NF-2, WT-1, MEN-1, MEN-H, p73, VHL, FCC and MCC.

IV. Biological Imaging Component

In some embodiments of the present invention, a dendrimer conjugate comprises at least one imaging agent that can be readily imaged. The present invention is not limited by the nature of the imaging component used. In some embodiments of the present invention, imaging modules comprise surface modifications of quantum dots (See e.g., Chan and Nie, Science 281:2016 (1998)) such as zinc sulfide-capped cadmium selenide coupled to biomolecules (Sooklal, Adv. Mater., 10:1083 (1998)).

In some embodiments, the imaging module comprises dendrimers produced according to the "nanocomposite" concept (See, e.g., Balogh et al., Proc. of ACS PMSE 77:118 (1997) and Balogh and Tomalia, J. Am. Che. Soc., 120:7355 (1998)). In these embodiments, dendrimers are produced by reactive encapsulation, where a reactant is preorganized by the dendrimer template and is then subsequently immobilized in/on the polymer molecule by a second reactant. Size, shape, size distribution and surface functionality of these nanoparticles are determined and controlled by the dendritic macromolecules. These materials have the solubility and compatibility of the host and have the optical or physiological properties of the guest molecule (i.e., the molecule that permits imaging). While the dendrimer host may vary according to the medium, it is possible to load the dendrimer hosts with different compounds and at various guest concentration levels. Complexes and composites may involve the use of a variety of metals or other inorganic materials. The high electron density of these materials considerably simplifies the imaging by electron microscopy and related scattering techniques. In addition, properties of inorganic atoms introduce new and measurable properties for imaging in either the presence or absence of interfering biological materials. In some embodiments of the present invention, encapsulation of gold, silver, cobalt, iron atoms/molecules and/or organic dye molecules such as fluorescein are encapsulated into dendrimers for use as nanoscopi composite labels/tracers, although any material that facilitates imaging or detection may be employed. In a preferred embodiment, the imaging agent is fluorescein isothiocyanate.

In some embodiments of the present invention, imaging is based on the passive or active observation of local differences in density of selected physical properties of the investigated complex matter. These differences may be due to a different shape (e.g., mass density detected by atomic force microscopy), altered composition (e.g. radiopaques detected by X-ray), distinct light emission (e.g., fluorochromes detected by spectrophotometry), different diffraction (e.g., electron-beam detected by TEM), contrasted absorption (e.g., light detected by optical methods), or special radiation emission (e.g., isotope methods), etc. Thus, quality and sensitivity of imaging depend on the property observed and on the technique used. The imaging techniques for cancerous cells have to provide sufficient levels of sensitivity to is observe small, local concentrations of selected cells. The earliest identification of cancer signatures requires high selectivity (i.e., highly specific recognition provided by appropriate targeting) and the highest possible sensitivity.

A. Magnetic Resonance Imaging

In some embodiments, once a targeted dendrimer conjugate has attached to (or been internalized into) a target cell (e.g., tumor cell and or inflammatory cell), one or more modules on the device serve to image its location. Dendrimers have already been employed as biomedical imaging agents, perhaps most notably for magnetic resonance imaging (MRI) contrast enhancement agents (See e.g., Wiener et al., Mag. Reson. Med. 31:1 (1994); an example using PAMAM dendrimers). These agents are typically constructed by conjugating chelated paramagnetic ions, such as Gd(III)-diethylenetriaminepentaacetic acid (Gd(III)-DTPA), to water-soluble dendrimers. Other paramagnetic ions that may be useful in this context include, but are not limited to, gadolinium, manganese, copper, chromium, iron, cobalt, erbium, nickel, europium, technetium, indium, samarium, dysprosium, ruthenium, ytterbium, yttrium, and holmium ions and combinations thereof. In some embodiments of the present invention, a dendrimer conjugate is also conjugated to a targeting group, such as epidermal growth factor (EGF), to make the conjugate specifically bind to the desired cell type (e.g., in the case of EGF, EGFR-expressing tumor cells). In a preferred embodiment of the present invention, DTPA is attached to dendrimers via the isothiocyanate of DTPA as described by Wiener (Wiener et al., Mag. Reson. Med. 31:1 (1994)).

Dendrimeric MRI agents are particularly effective due to the polyvalency, size and architecture of dendrimers, which results in molecules with large proton relaxation enhancements, high molecular relaxivity, and a high effective concentration of paramagnetic ions at the target site. Dendrimeric gadolinium contrast agents have even been used to differentiate between benign and malignant breast tumors using dynamic MRI, based on how the vasculature for the latter type of tumor images more densely (Adam et al., Ivest. Rad. 31:26 (1996)). Thus, MRI provides a particularly useful imaging system of the present invention.

B. Microscopic Imaging

Static structural microscopic imaging of cancerous cells and tissues has traditionally been performed outside of the patient. Classical histology of tissue biopsies provides a fine illustrative example, and has proven a powerful adjunct to cancer diagnosis and treatment. After removal, a specimen is sliced thin (e.g., less than 40 microns), stained, fixed, and examined by a pathologist. If images are obtained, they are most often 2-D transmission bright-field projection images. Specialized dyes are employed to provide selective contrast, which is almost absent from the unstained tissue, and to also provide for the identification of aberrant cellular constituents. Quantifying sub-cellular structural features by using computer-assisted analysis, such as in nuclear ploidy determination, is often confounded by the loss of histologic context owing to the thinness of the specimen and the overall lack of 3-D information. Despite the limitations of the static imaging approach, it has been invaluable to allow for the identification of neoplasia in biopsied tissue. Furthermore, its use is often the crucial factor in the decision to perform invasive and risky combinations of chemotherapy, surgical procedures, and radiation treatments, which are often accompanied by severe collateral tissue damage, complications, and even patient death.

A dendrimer conjugate of the present invention allows functional microscopic imaging of tumors and provide improved methods for imaging. The methods find use in vivo, in vitro, and ex vivo. For example, in one embodiment of the present invention, dendrimer conjugates of the present invention are designed to emit light or other detectable signals upon exposure to light. Although the labeled dendrimers may be physically smaller than the optical resolution limit of the microscopy technique, they become self-luminous objects when excited and are readily observable and measurable using optical techniques. In some embodiments of the present invention, sensing fluorescent biosensors in a microscope involves the use of tunable excitation and emission filters and multiwavelength sources (See, e.g., Farkas et al., SPEI 2678: 200 (1997)). In embodiments where the imaging agents are present in deeper tissue, longer wavelengths in the Near-infrared (NMR) are used (See e.g., Lester et al., Cell Mol. Biol. 44:29 (1998)). Dendrimeric biosensing in the Near-IR has been demonstrated with dendrimeric biosensing antenna-like architectures (See, e.g., Shortreed et al., J. Phys. Chem., 101:6318 (1997)). Biosensors that find use with the present invention include, but are not limited to, fluorescent dyes and molecular beacons.

In some embodiments of the present invention, in vivo imaging is accomplished using functional imaging techniques. Functional imaging is a complementary and potentially more powerful techniques as compared to static structural imaging. Functional imaging is best known for its application at the macroscopic scale, with examples including functional Magnetic Resonance Imaging (fMRI) and Positron Emission Tomography (PET). However, functional microscopic imaging may also be conducted and find use in in vivo and ex vivo analysis of living tissue. Functional microscopic imaging is an efficient combination of 3-D imaging, 3-D spatial multispectral volumetric assignment, and temporal sampling: in short a type of 3-D spectral microscopic movie loop. Interestingly, cells and tissues autofluoresce. When excited by several wavelengths, providing much of the basic 3-D structure needed to characterize several cellular components (e.g., the nucleus) without specific labeling. Oblique light illumination is also useful to collect structural information and is used routinely. As opposed to structural spectral microimaging, functional spectral microimaging may be used with biosensors, which act to localize physiologic signals within the cell or tissue. For example, in some embodiments of the present invention, biosensor-comprising dendrimers of the present invention are used to image upregulated receptor families such as the folate or EGF classes. In such embodiments, functional biosensing therefore involves the detection of physiological abnormalities relevant to carcinogenesis or malignancy, even at early stages. A number of physiological conditions may be imaged using the compositions and methods of the present invention including, but not limited to, detection of nanoscopic dendrimeric biosensors for pH, oxygen concentration, $Ca^{2+}$ concentration, and other physiologically relevant analytes.

V. Biological Monitoring Component

The biological monitoring or sensing component of a dendrimer conjugate of the present invention is one that can monitor the particular response in a target cell (e.g., tumor cell) induced by an agent (e.g., a therapeutic agent provided by the therapeutic component of the dendrimer conjugate). While the present invention is not limited to any particular monitoring system, the invention is illustrated by methods and compositions for monitoring cancer treatments. In preferred embodiments of the present invention, the agent induces apoptosis in cells and monitoring involves the detection of apoptosis. In particular embodiments, the monitoring component is an agent that fluoresces at a particular wavelength when apoptosis occurs. For example, in a preferred embodiment, caspase activity activates green fluorescence in the monitoring component. Apoptotic cancer cells, which have turned red as a result of being targeted by a particular signature with a red label, turn orange while residual cancer cells remain red. Normal cells induced to undergo apoptosis (e.g., through collateral damage), if present, will fluoresce green.

In these embodiments, fluorescent groups such as fluorescein are employed in the monitoring component. Fluorescein is easily attached to the dendrimer surface via the isothiocyanate derivatives, available from MOLECULAR PROBES, Inc. This allows the dendrimer conjugate to be imaged with the cells via confocal microscopy. Sensing of the effectiveness of the dendrimer conjugates is preferably achieved by using fluorogenic peptide enzyme substrates. For example, apoptosis caused by the therapeutic agents results in the production of the peptidase caspase-1 (ICE). CALBIOCHEM sells a number of peptide substrates for this enzyme that release a fluorescent moiety. A particularly useful peptide for use in the present invention is:

(SEQ ID NO: 1)
MCA-Tyr-Glu-Val-Asp-Gly-Trp-Lys-(DNP)-NH$_2$ where MCA is the (7-methoxycoumarin-4-yl)acetyl and DNP is the 2,4-dinitrophenyl group (See, e.g., Talanian et al., J. Biol. Chem., 272: 9677 (1997)). In this peptide, the MCA group has greatly attenuated fluorescence, due to fluorogenic resonance energy transfer (FRET) to the DNP group. When the enzyme cleaves the peptide between the aspartic acid and glycine residues, the MCA and DNP are separated, and the MCA group strongly fluoresces green (excitation maximum at 325 nm and emission maximum at 392 nm).

In some embodiments of the present invention, the lysine end of the peptide is linked to the dendrimer conjugate, so that the MCA group is released into the cytosol when it is cleaved. The lysine end of the peptide is a useful synthetic handle for conjugation because, for example, it can react with the activated ester group of a bifunctional linker such as Mal-PEG-OSu. Thus the appearance of green fluorescence in the target cells produced using these methods provides a clear indication that apoptosis has begun (if the cell already has a red color from the presence of aggregated quantum dots, the cell turns orange from the combined colors).

Additional fluorescent dyes that find use with the present invention include, but are not limited to, acridine orange, reported as sensitive to DNA changes in apoptotic cells (Abrams et al., Development 117:29 (1993)) and cis-parinaric acid, sensitive to the lipid peroxidation that accompanies apoptosis (Hockenbery et al., Cell 75:241 (1993)). It should be noted that the peptide and the fluorescent dyes are merely exemplary. It is contemplated that any peptide that effectively acts as a substrate for a caspase produced as a result of apoptosis finds use with the present invention.

VI. Targeting Agents

As described above, another component of the present invention is that the dendrimer conjugate compositions are able to specifically target a particular cell type (e.g., tumor cell). In some embodiments, the dendrimer conjugate targets neoplastic cells through a cell surface moiety and is taken into the cell through receptor mediated endocytosis.

In some embodiments of the present invention, targeting groups are conjugated to dendrimers and/or linkers conjugated to the dendrimers with either short (e.g., direct coupling), medium (e.g. using small-molecule bifunctional linkers such as SPDP, sold by PIERCE CHEMICAL Company), or long (e.g., PEG bifunctional linkers, sold by NEKTAR, Inc.) linkages. Since dendrimers have surfaces with a large number of functional groups, more than one targeting group and/or linker may be attached to each dendrimer. As a result, multiple binding events may occur between the dendrimer conjugate and the target cell. In these embodiments, the dendrimer conjugates have a very high affinity for their target cells via this "cooperative binding" or polyvalent interaction effect.

For steric reasons, in some embodiments, the smaller the ligands, the more can be attached to the surface of a dendrimer and/or linkers attached thereto. Recently, Wiener reported that dendrimers with attached folic acid would specifically accumulate on the surface and within tumor cells expressing the high-affinity folate receptor (hFR) (See, e.g., Wiener et al., Invest. Radiol., 32:748 (1997)). The hFR receptor is expressed or upregulated on epithelial tumors, including breast cancers. Control cells lacking hFR showed no significant accumulation of folate-derivatized dendrimers. Folic acid can be attached to full generation PAMAM dendrimers via a carbodiimide coupling reaction. Folic acid is a good targeting candidate for the dendrimers, with its small size and a simple conjugation procedure.

Antibodies can be generated to allow for the targeting of antigens or immunogens (e.g., tumor, tissue or pathogen specific antigens) on various biological targets (e.g., pathogens, tumor cells, normal tissue). Such antibodies include, but are not limited to polyclonal, monoclonal, chimeric, single chain, Fab fragments, and an Fab expression library.

In some embodiments, the antibodies recognize tumor specific epitopes (e.g., TAG-72 (See, e.g., Kjeldsen et al., Cancer Res. 48:2214-2220 (1988); U.S. Pat. Nos. 5,892,020; 5,892,019; and 5,512,443); human carcinoma antigen (See, e.g., U.S. Pat. Nos. 5,693,763; 5,545,530; and 5,808,005); TP1 and TP3 antigens from osteocarcinoma cells (See, e.g., U.S. Pat. No. 5,855,866); Thomsen-Friedenreich (TF) antigen from adenocarcinoma cells (See, e.g., U.S. Pat. No. 5,110,911); "KC-4 antigen" from human prostrate adenocarcinoma (See, e.g., U.S. Pat. Nos. 4,708,930 and 4,743,543); a human colorectal cancer antigen (See, e.g., U.S. Pat. No. 4,921,789); CA125 antigen from cystadenocarcinoma (See, e.g., U.S. Pat. No. 4,921,790); DF3 antigen from human breast carcinoma (See, e.g., U.S. Pat. Nos. 4,963,484 and 5,053,489); a human breast tumor antigen (See, e.g., U.S. Pat. No. 4,939,240); p97 antigen of human melanoma (See, e.g., U.S. Pat. No. 4,918, 164); carcinoma or orosomucoid-related antigen (CORA) (See, e.g., U.S. Pat. No. 4,914,021); a human pulmonary carcinoma antigen that reacts with human squamous cell lung carcinoma but not with human small cell lung carcinoma (See, e.g., U.S. Pat. No. 4,892,935); T and Tn haptens in glycoproteins of human breast carcinoma (See, e.g., Springer et al., Carbohydr. Res. 178:271-292 (1988)), MSA breast carcinoma glycoprotein termed (See, e.g., Tjandra et al., Br. J. Surg. 75:811-817 (1988)); MFGM breast carcinoma antigen (See, e.g., Ishida et al., Tumor Biol. 10:12-22 (1989)); DU-PAN-2 pancreatic carcinoma antigen (See, e.g., Lan et al., Cancer Res. 45:305-310 (1985)); CA125 ovarian carcinoma antigen (See, e.g., Hanisch et al., Carbohydr. Res. 178:29-47 (1988)); YH206 lung carcinoma antigen (See, e.g., Hinoda et al., (1988) Cancer J. 42:653-658 (1988)). Each of the foregoing references are specifically incorporated herein by reference.

Various procedures known in the art are used for the production of polyclonal antibodies. For the production of antibody, various host animals can be immunized by injection with the peptide corresponding to the desired epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin (KLH)). Various adjuvants are used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

For preparation of monoclonal antibodies, any technique that provides for the production of antibody molecules by continuous cell lines in culture may be used (See e.g., Harlow and Lane, Antibodies: A Laboratory Manual, Cold Spring Harbor Laboratory Press, Cold Spring Harbor, N.Y.). These include, but are not limited to, the hybridoma technique originally developed by Kohler and Milstein (Kohler and Milstein, Nature 256:495-497 (1975)), as well as the trioma technique, the human B-cell hybridoma technique (See e.g., Kozbor et al. Immunol. Today 4:72 (1983)), and the EBV-hybridoma technique to produce human monoclonal antibodies (Cole et al., in Monoclonal Antibodies and Cancer Therapy, Alan R. Liss, Inc., pp. 77-96 (1985)).

In an additional embodiment of the invention, monoclonal antibodies can be produced in germ-free animals utilizing recent technology (See e.g., PCT/US90/02545). According to the invention, human antibodies may be used and can be obtained by using human hybridomas (Cote et al., Proc. Natl. Acad. Sci. U.S.A. 80:2026-2030 (1983)) or by transforming human B cells with EBV virus in vitro (Cole et al., in Monoclonal Antibodies and Cancer Therapy, Alan R. Liss, pp. 77-96 (1985)).

According to the invention, techniques described for the production of single chain antibodies (U.S. Pat. No. 4,946, 778; herein incorporated by reference) can be adapted to produce specific single chain antibodies. An additional embodiment of the invention utilizes the techniques described for the construction of Fab expression libraries (Huse et al., Science 246:1275-1281 (1989)) to allow rapid and easy identification of monoclonal Fab fragments with the desired specificity.

Antibody fragments that contain the idiotype (antigen binding region) of the antibody molecule can be generated by known techniques. For example, such fragments include but are not limited to: the F(ab')2 fragment that can be produced by pepsin digestion of the antibody molecule; the Fab' fragments that can be generated by reducing the disulfide bridges of the F(ab')2 fragment, and the Fab fragments that can be generated by treating the antibody molecule with papain and a reducing agent.

In the production of antibodies, screening for the desired antibody can be accomplished by techniques known in the art (e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), Western Blots, precipitation reactions, agglutination assays (e.g., gel agglutination assays, hemagglutination assays, etc.), complement fixation assays, immunofluorescence assays, protein A assays, and immunoelectrophoresis assays, etc.).

The dendrimer conjugates of the present invention have many advantages over liposomes, such as their greater stability, better control of their size and polydispersity, and generally lower toxicity and immunogenicity (See e.g., Duncan et al, Polymer Preprints 39:180 (1998)). Thus, in some embodiments of the present invention, anti-HER2 antibody fragments, as well as other targeting antibodies are conjugated to dendrimers, as targeting agents for the nanodevices of the present invention.

The bifunctional linkers SPDP and SMCC and the longer Mal-PEG-OSu linkers are particularly useful for antibody-dendrimer conjugation. In addition, many tumor cells contain surface lectins that bind to oligosaccharides, with specific recognition arising chiefly from the terminal carbohydrate residues of the latter (See, e.g., Sharon and L is, Science 246:227 (1989)). Attaching appropriate monosaccharides to nonglycosylated proteins such as BSA provides a conjugate that binds to tumor lectin much more tightly than the free monosaccharide (See, e.g., Monsigny et al., Biochemie 70:1633 (1988)).

Mannosylated PAMAM dendrimers bind mannoside-binding lectin up to 400 more avidly than monomeric mannosides (See, e.g., Page and Roy, Bioconjugate Chem., 8:714 (1997)). Sialylated dendrimers and other dendritic polymers bind to and inhibit a variety of sialate-binding viruses both in vitro and in vivo. By conjugating multiple monosaccharide residues (e.g., α-galactoside, for galactose-binding cells) to dendrimers, polyvalent conjugates are created with a high affinity for the corresponding type of tumor cell. The attachment reaction are easily carried out via reaction of the terminal amines with commercially-available α-galactosidyl-phenylisothiocyanate. The small size of the carbohydrates allows a high concentration to be present on the dendrimer surface.

Related to the targeting approaches described above is the "pretargeting" approach (See e.g., Goodwin and Meares, Cancer (suppl.) 80:2675 (1997)). An example of this strategy involves initial treatment of a subject with conjugates of tumor-specific monoclonal antibodies and streptavidin. Remaining soluble conjugate is removed from the bloodstream with an appropriate biotinylated clearing agent. When the tumor-localized conjugate is all that remains, a radiolabeled, biotinylated agent is introduced, which in turn localizes at the tumor sites by the strong and specific biotin-streptavidin interaction. Thus, the radioactive dose is maximized in dose proximity to the cancer cells and minimized in the rest of the body where it can harm healthy cells.

It has been shown that if streptavidin molecules bound to a polystyrene well are first treated with a biotinylated dendrimer, and then radiolabeled streptavidinis introduced, up to four of the labeled streptavidin molecules are bound per polystyrene-bound streptavidin (See, e.g., Wilbur et al., Bioconjugate Chem., 9:813 (1998)). Thus, biotinylated dendrimers may be used in the methods of the present invention, acting as a polyvalent receptor for the radiolabel in vivo, with a resulting amplification of the radioactive dosage per bound antibody conjugate. In the preferred embodiments of the present invention, one or more multiply-biotinylated module(s) on the clustered dendrimer presents a polyvalent target for radiolabeled or boronated (See, e.g., Barth et al., Cancer Investigation 14:534 (1996)) avidin or streptavidin, again resulting in an amplified dose of radiation for the tumor cells.

Dendrimers may also be used as clearing agents by, for example, partially biotinylating a dendrimer that has a polyvalent galactose or mannose surface. The conjugate-clearing agent complex would then have a very strong affinity for the corresponding hepatocyte receptors.

In other embodiments of the present invention, an enhanced permeability and retention (EPR) method is used in targeting. The enhanced permeability and retention (EPR) effect is a more "passive" way of targeting tumors (See, e.g., Duncan and Sat, Ann. Oncol., 9:39 (1998)). The EPR effect is the selective concentration of macromolecules and small particles in the tumor microenvironment, caused by the hyperpermeable vasculature and poor lymphatic drainage of tumors. The dendrimer compositions of the present invention provide ideal polymers for this application, in that they are relatively rigid, of narrow polydispersity, of controlled size and surface chemistry, and have interior "cargo" space that can carry and then release antitumor drugs. In fact, PAMAM dendrimer-platinates have been shown to accumulate in solid tumors (Pt levels about 50 times higher than those obtained with cisplatin) and have in vivo activity in solid tumor models for which cisplatin has no effect (See, e.g., Malik et al., Proc. Intl. Symp. Control. Rel. Bioact. Mater., 24:107 (1997) and Duncan et al., Polymer Preprints 39:180 (1998)).

VII. Synthesis and Conjugation

The present section provides a description of the synthesis and formation of dendrimer conjugates described above (See, e.g., Examples 1-7).

In some embodiments of the present invention, the preparation of PAMAM dendrimers is performed according to a typical divergent (building up the macromolecule from an initiator core) synthesis. It involves a two-step growth sequence that includes of a Michael addition of amino groups to the double bond of methyl acrylate (MA) followed by the amidation of the resulting terminal carbomethoxy, —($CO_2$ $CH_3$) group, with ethylenediamine (EDA).

In the first step of this process, ammonia is allowed to react under an inert nitrogen atmosphere with MA (molar ratio: 1:4.25) at 47° C. for 48 hours. The resulting compound is referred to as generation=0, the star-branched PAMAM tri-ester. The next step involves reacting the tri-ester with an excess of EDA to produce the star-branched PAMAM tri-amine (G=O). This reaction is performed under an inert atmosphere (nitrogen) in methanol and requires 48 hours at 0° C. for completion. Reiteration of this Michael addition and amidation sequence produces generation=1.

Preparation of this tri-Amine Completes the First Full Cycle of the Divergent Synthesis of PAMAM dendrimers. Repetition of this reaction sequence results in the synthesis of larger generation (G=1-5) dendrimers (i.e., ester- and amine-terminated molecules, respectively). For example, the second iteration of this sequence produces generation 1, with an hexa-ester and hexa-amine surface, respectively. The same reactions are performed in the same way as for all subsequent generations from 1 to 9, building up layers of branch cells giving a core-shell architecture with precise molecular weights and numbers of terminal groups as shown above. Carboxylate-surfaced dendrimers can be produced by hydrolysis of ester-terminated PAMAM dendrimers, or reaction of succinic anhydride with amine-surfaced dendrimers (e.g., full generation PAMAM, POPAM or POPAM-PAMAM hybrid dendrimers).

Various dendrimers can be synthesized based on the core structure that initiates the polymerization process. These core structures dictate several important characteristics of the dendrimer molecule such as the overall shape, density, and surface functionality (See, e.g., Tomalia et al., Angew. Chem. Int. Ed. Engl., 29:5305 (1990)). Spherical dendrimers derived from ammonia possess trivalent initiator cores, whereas EDA is a tetra-valent initiator core. Recently, rod-shaped dendrimers have been reported which are based upon linear poly (ethyleneimine) cores of varying lengths the longer the core, the longer the rod (See, e.g., Yin et al., J. Am. Chem. Soc., 120:2678 (1998)).

In some embodiments, dendrimers of the present invention comprise a protected core diamine. In some embodiments, the protected initiator core diamine is NH2-($CH_2$)$_n$-NHPG, (n=1-10). In other embodiments, the intitor core is selected from the group comprising, but not limited to, NH2-(CH2)$_n$-NH2 (n=1-10), NH2-((CH2)$_n$NH2)$_3$ (n=1-10), or unsubstituted or substituted 1,2-; 1,3-; or 1,4-phenylenedi-n-alkylamine, with a monoprotected diamine (e.g., NH2-(CH2)$_n$-NHPG) used during the amide formation of each generation. In these approaches, the protected diamine allows for the large scale production of dendrimers without the production of non-uniform nanostructures that can make characterization and analysis difficult. By limiting the reactivity of the diamine to only one terminus, the opportunities of dimmer/polymer formation and intramolecular reactions are obviated without the need of employing large excesses of diamine. The terminus monoprotected intermediates can be readily purified since the protecting groups provide suitable handle for productive purifications by classical techniques like crystallization and or chromatography.

The protected intermediates can be deprotected in a deprotection step, and the resulting generation of the dendrimer subjected to the next iterative chemical reaction without the need for purification. The invention is not limited to a particular protecting group. Indeed a variety of protecting groups are contemplated including, but not limited to, t-butoxycarbamate (N-t-Boc), allyloxycarbamate (N-Alloc), benzylcarbamate (N-Cbz), 9-fluorenylmethylcarbamate (FMOC), or phthalimide (Phth). In preferred embodiments of the present invention, the protecting group is benzylcarbamate (N-Cbz). N-Cbz is ideal for the present invention since it alone can be easily cleaved under "neutral" conditions by catalytic hydrogenation (Pd/C) without resorting to strongly acidic or basic conditions needed to remove an F-MOC group. The use of protected monomers finds particular use in high through-put production runs because a lower amount of monomer can be used, reducing production costs.

The dendrimers may be characterized for size and uniformity by any suitable analytical techniques. These include, but are not limited to, atomic force microscopy (AFM), electrospray-ionization mass spectroscopy, MALDI-TOF mass spectroscopy, $^{13}$C nuclear magnetic resonance spectroscopy, high performance liquid chromatography (HPLC) size exclusion chromatography (SEC) (equipped with multi-angle laser light scattering, dual UV and refractive index detectors), capillary electrophoresis and get electrophoresis. These analytical methods assure the uniformity of the dendrimer population and are important in the quality control of dendrimer production for eventual use in in vivo applications. Most importantly, extensive work has been performed with dendrimers showing no evidence of toxicity when administered intravenously (Roberts et al., J. Biomed. Mater. Res., 30:53 (1996) and Boume et al., J. Magnetic Resonance Imaging, 6:305 (1996)).

VIII. Evaluation of Anti-Tumor Efficacy and Toxicity of Dendrimers

The anti-tumor effects of various therapeutic agents on cancer cell lines and primary cell cultures may be evaluated using the nanodevices of the present invention. For example, in preferred embodiments, assays are conducted, in vitro, using established tumor cell line models or primary culture cells.

A. Quantifying the Induction of Apoptosis of Human Tumor Cells In Vitro

In an exemplary embodiment of the present invention, the dendrimer conjugates of the present invention are used to assay apoptosis of human tumor cells in vitro. Testing for apoptosis in the cells determines the efficacy of the therapeutic agent. Multiple aspects of apoptosis can and should be measured. These aspects include those described above, as well as aspects including, but are not limited to, measurement of phosphatidylserine (PS) translocation from the inner to outer surface of plasma membrane, measurement of DNA fragmentation, detection of apoptosis related proteins, and measurement of Caspase-3 activity.

B. In Vitro Toxicology

In some embodiments of the present invention, to gain a general perspective into the safety of a particular dendrimer conjugate platform or component of that system, toxicity testing is performed. Toxicological information may be derived from numerous sources including, but not limited to, historical databases, in vitro testing, and in vivo animal studies.

In vitro toxicological methods have gained popularity in recent years due to increasing desires for alternatives to animal experimentation and an increased perception to the potential ethical, commercial, and scientific value. In vitro toxicity testing systems have numerous advantages including improved efficiency, reduced cost, and reduced variability between experiments. These systems also reduce animal usage, eliminate confounding systemic effects (e.g., immunity), and control environmental conditions.

Although any in vitro testing system may be used with the present invention, the most common approach utilized for in vitro examination is the use of cultured cell models. These systems include freshly isolated cells, primary cells, or transformed cell cultures. Cell culture as the primary means of studying in vitro toxicology is advantageous due to rapid screening of multiple cultures, usefulness in identifying and assessing toxic effects at the cellular, subcellular, or molecular level. In vitro cell culture methods commonly indicate basic cellular toxicity through measurement of membrane integrity, metabolic activities, and subcellular perturbations. Commonly used indicators for membrane integrity include cell viability (cell count), clonal expansion tests, trypan blue exclusion, intracellular enzyme release (e.g. lactate dehydrogenase), membrane permeability of small ions ($K^1$, $Ca^{2+}$), and intracellular Ala accumulation of small molecules (e.g., $^{51}Cr$, succinate). Subcellular perturbations include monitoring mitochondrial enzyme activity levels via, for example, the MTT test, determining cellular adenine triphosphate (ATP) levels, neutral red uptake into lysosomes, and quantification of total protein synthesis. Metabolic activity indicators include glutathione content, lipid peroxidation, and lactate/pyruvate ratio.

C. MTT Assay

The MTT assay is a fast, accurate, and reliable methodology for obtaining cell viability measurements. The MTT assay was first developed by Mosmann (See, e.g., Mosmann, J. Immunol. Meth., 65:55 (1983)). It is a simple colorimetric assay numerous laboratories have utilized for obtaining toxicity results (See e.g., Kuhlmann et al., Arch. Toxicol., 72:536 (1998)). Briefly, the mitochondria produce ATP to provide sufficient energy for the cell. In order to do this, the mitochondria metabolize pyruvate to produce acetyl CoA. Within the mitochondria, acetyl CoA reacts with various enzymes in the tricarboxylic acid cycle resulting in subsequent production of ATP. One of the enzymes particularly useful in the MTT assay is succinate dehydrogenase. MTT (3-(4,5-dimethylthiazol-2-yl)-2 diphenyl tetrazolium bromide) is a yellow substrate that is cleaved by succinate dehydrogenase forming a purple formazan product. The alteration in pigment identifies changes in mitochondria function. Nonviable cells are unable to produce formazan, and therefore, the amount produced directly correlates to the quantity of viable cells. Absorbance at 540 nm is utilized to measure the amount of formazan product.

The results of the in vitro tests can be compared to in vivo toxicity tests in order to extrapolate to live animal conditions.

Typically, acute toxicity from a single dose of the substance is assessed. Animals are monitored over 14 days for any signs of toxicity (increased temperature, breathing difficulty, death, etc). Traditionally, the standard of acute toxicity is the median lethal dose ($LD_{50}$), which is the predicted dose at which half of the treated population would be killed. The determination of this dose occurs by exposing test animals to a geometric series of doses under controlled conditions. Other tests include subacute toxicity testing, which measures the animal's response to repeated doses of the nanodevice for no longer than 14 days. Subchronic toxicity testing involves testing of a repeated dose for 90 days. Chronic toxicity testing is similar to subchronic testing but may last for over a 90-day period. In vivo testing can also be conducted to determine toxicity with respect to certain tissues. For example, in some embodiments of the present invention tumor toxicity (i.e., effect of the compositions of the present invention on the survival of tumor tissue) is determined (e.g., by detecting changes in the size and/or growth of tumor tissues).

IX. Gene Therapy Vectors

In some embodiments of the present invention, the dendrimer conjugates comprise transgenes for delivery and expression to a target cell or tissue, in vitro, ex vivo, or in vivo. In such embodiments, rather than containing the actual protein, the dendrimer complex comprises an expression vector construct containing, for example, a heterologous DNA encoding a gene of interest and the various regulatory elements that facilitate the production of the particular protein of interest in the target cells.

In some embodiments, the gene is a therapeutic gene that is used, for example, to treat cancer, to replace a defective gene, or a marker or reporter gene that is used for selection or monitoring purposes. In the context of a gene therapy vector, the gene may be a heterologous piece of DNA. The heterologous DNA may be derived from more than one source (i.e., a multigene construct or a fusion protein). Further, the heterologous DNA may include a regulatory sequence derived from one source and the gene derived from a different source.

Tissue-specific promoters may be used to effect transcription in specific tissues or cells so as to reduce potential toxicity or undesirable effects to non-targeted tissues. For example, promoters such as the PSA, probasin, prostatic acid phosphatase or prostate-specific glandular kallikrein (hK2) may be used to target gene expression in the prostate. Similarly, promoters may be used to target gene expression in other tissues (e.g., insulin, elastin amylase, pdr-1, pdx-1 and glucokinase promoters target to the pancreas; albumin PEPCK, HBV enhancer, alpha fetoproteinapolipoprotein C, alpha-1 antitrypsin, vitellogenin, NF-AB and transthyretin promoters target to the liver; myosin H chain, muscle creatine kinase, dystrophin, calpain p94, skeletal alpha-actin, fast troponin 1 promoters target to skeletal muscle; keratin promoters target the skin; sm22 alpha; SM-.alpha.-actin promoters target smooth muscle; CFTR; human cytokeratin 18 (K18); pulmonary surfactant proteins A, B and Q CC-10; P1 promoters target lung tissue; endothelin-1; E-selectin; von Willebrand factor; KDR/flk-1 target the endothelium; tyrosinase targets melanocytes).

The nucleic acid may be either cDNA or genomic DNA. The nucleic acid can encode any suitable therapeutic protein. Preferably, the nucleic acid encodes a tumor suppressor, cytokine, receptor, inducer of apoptosis, or differentiating agent. The nucleic acid may be an antisense nucleic acid. In such embodiments, the antisense nucleic acid may be incorporated into the nanodevice of the present invention outside of the context of an expression vector.

In preferred embodiments, the nucleic acid encodes a tumor suppressor, cytokines, receptors, or inducers of apoptosis. Suitable tumor suppressors include BRCA1, BRCA2, C-CAM, p16, p211 p53, p73, or Rb. Suitable cytokines include GMCSF, IL-1, IL-2, IL-3, IL-4, IL-5, IL6, IL-7, IL-8, IL-9, IL-10, IL-11, IL-12, IL-13, IL-14, IL-15, β-interferon, γ-interferon, or TNF. Suitable receptors include CFTR, EGFR, estrogen receptor, IL-2 receptor, or VEGFR. Suitable inducers of apoptosis include AdE1B, Bad, Bak, Bax, Bid, Bik, Bim, Harakiri, or ICE-CED3 protease.

X. Methods of Combined Therapy

Tumor cell resistance to DNA damaging agents represents a major problem in clinical oncology. Dendrimer conjugates of the present invention provide means of ameliorating this problem by effectively administering a combined therapy approach. However, it should be noted that traditional combination therapy may be employed in combination with the nanodevices of the present invention. For example, in some embodiments of the present invention, dendrimer conjugates may be used before, after, or in combination with the traditional therapies.

To kill cells, inhibit cell growth, or metastasis, or angiogenesis, or otherwise reverse or reduce the malignant phenotype of tumor cells using the methods and compositions of the present invention in combination therapy, one contacts a "target" cell with the nanodevices compositions described herein and at least one other agent. These compositions are provided in a combined amount effective to kill or inhibit proliferation of the cell. This process may involve contacting the cells with the immunotherapeutic agent and the agent(s) or factor(s) at the same time. This may be achieved by contacting the cell with a single composition or pharmacological formulation that includes both agents, or by contacting the cell with two distinct compositions or formulations, at the same time, wherein one composition includes, for example, an expression construct and the other includes a therapeutic agent.

Alternatively, dendrimer conjugate treatment may precede or follow the other agent treatment by intervals ranging from minutes to weeks. In embodiments where the other agent and immunotherapy are applied separately to the cell, one would generally ensure that a significant period of time did not expire between the time of each delivery, such that the agent and nanodevice would still be able to exert an advantageously combined effect on the cell. In such instances, it is contemplated that cells are contacted with both modalities within about 12-24 hours of each other and, more preferably, within about 6-12 hours of each other, with a delay time of only about 12 hours being most preferred. In some situations, it may be desirable to extend the time period for treatment significantly, however, where several days (2 to 7) to several weeks (1 to 8) lapse between the respective administrations.

In some embodiments, more than one administration of the immunotherapeutic composition of the present invention or the other agent are utilized. Various combinations may be employed, where the dendrimer is "A" and the other agent is "B", as exemplified below: A/B/A, B/A/B, B/B/A, A/A/B, B/A/A, A/B/B, B/B/B/A, B/B/A/B, A/A/B/B, A/B/A/B, A/B/B/A, B/B/A/A, B/A/B/A, B/A/A/B, B/B/B/A, A/A/A/B, B/A/A/A, A/B/A/A, A/A/B/A, A/B/B/B, B/A/B/B, B/B/A/B.

Other combinations are contemplated. Again, to achieve cell killing, both agents are delivered to a cell in a combined amount effective to kill or disable the cell.

Other factors that may be used in combination therapy with the dendrimer conjugates of the present invention include, but are not limited to, factors that cause DNA damage such as .gamma.-rays, X-rays, and/or the directed delivery of radioisotopes to tumor cells. Other forms of DNA damaging factors are also contemplated such as microwaves and UV-irradiation. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells. The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

In preferred embodiments of the present invention, the regional delivery of the dendrimer conjugates to patients with cancers is utilized to maximize the therapeutic effectiveness of the delivered agent. Similarly, the chemo- or radiotherapy may be directed to particular, affected region of the subjects body. Alternatively, systemic delivery of the immunotherapeutic composition and/or the agent may be appropriate in certain circumstances, for example, where extensive metastasis has occurred.

In addition to combining the dendrimer conjugates with chemo- and radiotherapies, it also is contemplated that traditional gene therapies are used. For example, targeting of p53 or p16 mutations along with treatment of the dendrimer conjugates provides an improved anti-cancer treatment. The present invention contemplates the co-treatment with other tumor-related genes including, but not limited to, p21, Rb, APC, DCC, NF-I, NF-2, BCRA2, p16, FHIT, WT-I, MEN-I, MEN-H, BRCA1, VHL, FCC, MCC, ras, myc, neu, raf erb, src, fms, jun, trk, ret, gsp, hst, bcl, and abl.

In vivo and ex vivo treatments are applied using the appropriate methods worked out for the gene delivery of a particular construct for a particular subject. For example, for viral vectors, one typically delivers $1\times10^4$, $1\times10^5$, $1\times10^6$, $1\times10^7$, $1\times10^8$, $1\times10^9$, $1\times10^{10}$, $1\times10^{11}$ or $1\times10^{12}$ infectious particles to the patient. Similar figures may be extrapolated for liposomal or other non-viral formulations by comparing relative uptake efficiencies.

An attractive feature of the present invention is that the therapeutic compositions may be delivered to local sites in a patient by a medical device. Medical devices that are suitable for use in the present invention include known devices for the localized delivery of therapeutic agents. Such devices include, but are not limited to, catheters such as injection catheters, balloon catheters, double balloon catheters, microporous balloon catheters, channel balloon catheters, infusion catheters, perfusion catheters, etc., which are, for example, coated with the therapeutic agents or through which the agents are administered; needle injection devices such as hypodermic needles and needle injection catheters; needleless injection devices such as jet injectors; coated stents, bifurcated stents, vascular grafts, stent grafts, etc.; and coated vaso-occlusive devices such as wire coils.

Exemplary devices are described in U.S. Pat. Nos. 5,935, 114; 5,908,413; 5,792,105; 5,693,014; 5,674,192; 5,876,445; 5,913,894; 5,868,719; 5,851,228; 5,843,089; 5,800,519; 5,800,508; 5,800,391; 5,354,308; 5,755,722; 5,733,303; 5,866,561; 5,857,998; 5,843,003; and 5,933,145; the entire contents of which are incorporated herein by reference. Exemplary stents that are commercially available and may be used in the present application include the RADIUS (SCIMED LIFE SYSTEMS, Inc.), the SYMPHONY (Boston Scientific Corporation), the Wallstent (Schneider Inc.), the PRECEDENT H (Boston Scientific Corporation) and the NIR (Medinol Inc.). Such devices are delivered to and/or implanted at target locations within the body by known techniques.

XI. Photodynamic Therapy

In some embodiments, the therapeutic complexes of the present invention comprise a photodynamic compound and a targeting agent that is administered to a patient. In some embodiments, the targeting agent is then allowed a period of time to bind the "target" cell (e.g. about 1 minute to 24 hours) resulting in the formation of a target cell-target agent complex. In some embodiments, the therapeutic complexes comprising the targeting agent and photodynamic compound are then illuminated (e.g., with a red laser, incandescent lamp, X-rays, or filtered sunlight). In some embodiments, the light is aimed at the jugular vein or some other superficial blood or lymphatic vessel. In some embodiments, the singlet oxygen and free radicals diffuse from the photodynamic compound to the target cell (e.g. cancer cell or pathogen) causing its destruction.

XII. Pharmaceutical Formulations

Where clinical applications are contemplated, in some embodiments of the present invention, the dendrimer conjugates are prepared as part of a pharmaceutical composition in a form appropriate for the intended application. Generally, this entails preparing compositions that are essentially free of pyrogens, as well as other impurities that could be harmful to humans or animals. However, in some embodiments of the present invention, a straight dendrimer formulation may be administered using one or more of the routes described herein.

In preferred embodiments, the dendrimer conjugates are used in conjunction with appropriate salts and buffers to render delivery of the compositions in a stable manner to allow for uptake by target cells. Buffers also are employed when the dendrimer conjugates are introduced into a patient. Aqueous compositions comprise an effective amount of the dendrimer conjugates to cells dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. Except insofar as any conventional media or agent is incompatible with the vectors or cells of the present invention, its use in therapeutic compositions is contemplated. Supplementary active ingredients may also be incorporated into the compositions.

In some embodiments of the present invention, the active compositions include classic pharmaceutical preparations. Administration of these compositions according to the present invention is via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection.

The active dendrimer conjugates may also be administered parenterally or intraperitoneally or intratumorally. Solutions of the active compounds as free base or pharmacologically acceptable salts are prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

In some embodiments, a therapeutic agent is released from dendrimer conjugates within a target cell (e.g., within an endosome). This type of intracellular release (e.g., endosomal disruption of a linker-therapeutic conjugate) is contemplated to provide additional specificity for the compositions and methods of the present invention. In some embodiments, the dendrimer conjugates of the present invention contain between 100-150 primary amines on the surface. Thus, the present invention provides dendrimers with multiple (e.g., 100-150) reactive sites for the conjugation of linkers and/or functional groups comprising, but not limited to, therapeutic agents, targeting agents, imaging agents and biological monitoring agents.

The compositions and methods of the present invention are contemplated to be equally effective whether or not the dendrimer conjugates of the present invention comprise a fluorescein (e.g. FITC) imaging agent. Thus, each functional group present in a dendrimer composition is able to work independently of the other functional groups. Thus, the present invention provides dendrimer conjugates that can comprise multiple combinations of targeting, therapeutic, imaging, and biological monitoring functional groups.

The present invention also provides a very effective and specific method of delivering molecules (e.g., therapeutic and imaging functional groups) to the interior of target cells (e.g., cancer cells). Thus, in some embodiments, the present invention provides methods of therapy that comprise or require delivery of molecules into a cell in order to function (e.g., delivery of genetic material such as siRNAs).

The pharmaceutical forms suitable for injectable use include sterile aqueous solutions or dispersions and sterile powders for the extemporaneous preparation of sterile injectable solutions or dispersions. The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it may be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, dendrimer conjugates are administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution is suitably buffered, if necessary, and the liquid diluent first rendered isotonic with sufficient saline or glucose. These particular aqueous solutions are especially suitable for intravenous, intramuscular, subcutaneous and intraperitoneal administration. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). In some embodiments of the present invention, the active particles or agents are formulated within a therapeutic mixture to comprise about 0.0001 to 1.0 milligrams, or about 0.001 to 0.1 milligrams, or about 0.1 to 1.0 or even about 10 milligrams per dose or so. Multiple doses may be administered.

Additional formulations that are suitable for other modes of administration include vaginal suppositories and pessaries. A rectal pessary or suppository may also be used. Suppositories are solid dosage forms of various weights and shapes, usually medicated, for insertion into the rectum, vagina or the urethra. After insertion, suppositories soften, melt or dissolve in the cavity fluids. In general, for suppositories, traditional binders and carriers may include, for example, polyalkylene glycols or triglycerides; such suppositories may be formed from mixtures containing the active ingredient in the range of 0.5% to 10%, preferably 1%-2%. Vaginal suppositories or pessaries are usually globular or oviform and weighing about 5 g each. Vaginal medications are available in a variety of physical forms, e.g., creams, gels or liquids, which depart from the classical concept of suppositories. In addition, suppositories may be used in connection with colon cancer. The dendrimer conjugates also may be formulated as inhalants for the treatment of lung cancer and such like.

XIII. Method of Treatment or Prevention of Cancer and Pathogenic Diseases

In some embodiments of the present invention methods and compositions are provided for the treatment of tumors in cancer therapy. It is contemplated that the present therapy can be employed in the treatment of any cancer for which a specific signature has been identified or which can be targeted. Cell proliferative disorders, or cancers, contemplated to be treatable with the methods of the present invention include human sarcomas and carcinomas, including, but not limited to, fibrosarcoma, myxosarcoma, liposarcoma, chondrosarcoma, osteogenic sarcoma, chordoma, angiosarcoma, endotheliosarcoma, lymphangiosarcoma, Ewing's tumor, lymphangioendotheliosarcoma, synovioma, mesothelioma, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilns' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease.

It is contemplated that the present therapy can be employed in the treatment of any pathogenic disease for which a specific signature has been identified or which can be targeted for a given pathogen. Examples of pathogens contemplated to be treatable with the methods of the present invention include, but are not limited to, *Legionella peomophilia, Mycobacterium tuberculosis, Clostridium tetani, Hemophilus influenzae, Neisseria gonorrhoeae, Treponema pallidum, Bacillus anthracis, Vibrio cholerae, Borrelia burgdorferi, Cornebacterium diphtheria, Staphylococcus aureus*, human papilloma virus, human immunodeficiency virus, rubella virus, polio virus, and the like.

EXPERIMENTAL

The following examples are provided in order to demonstrate and further illustrate certain preferred embodiments and aspects of the present invention and are not to be construed as limiting the scope thereof.

Example 1

Experiments were conducted during development of embodiments of the invention in order to analyze and characterize various schemes for generating dendrimer conjugates wherein a dendrimer is conjugated to one or more linkers that comprise multiple sites for binding (e.g., covalent binding) moieties. A drug releasing mechanism for esterase sensitive linker-dendrimer conjugates was analyzed (See e.g., FIG. 10). In some embodiments, once the ester bond is cleaved (e.g., by esterases (e.g., present at a target site (e.g., intrinsic to the target))), irreversible decomposition of the linkers leads to release of drug and/or therapeutic agent (e.g., at the target site).

Figure 11:
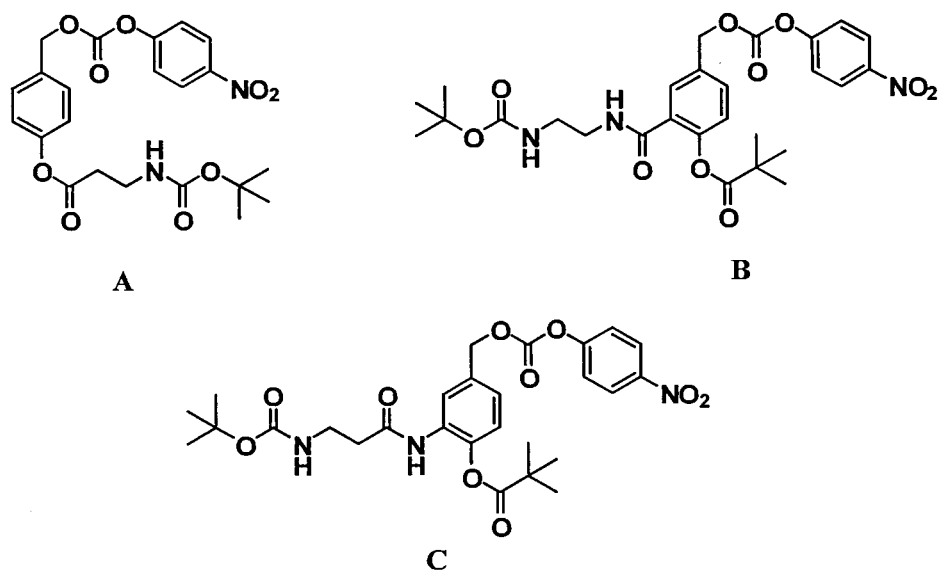
FIG. 11 shows examples of several (A, B, and C) elimination linkers designed for esterase triggered cleavage.

Three elimination linkers (See FIG. 11, A-C) designed for esterase triggered cleavage were synthesized. In some embodiments, the linkers are conjugated to a therapeutic agent and/or to a dendrimer (e.g., G5 dendrimer).

Example 2

Synthesis of Esterase Sensitive Linker 11A

A synthesis scheme of a dendrimer (e.g., G5 PAMAM dendrimer) conjugated to a therapeutic agent (e.g., TAXOL) with an esterase sensitive linker (esterase sensitive elimination linker 11A) is shown below.

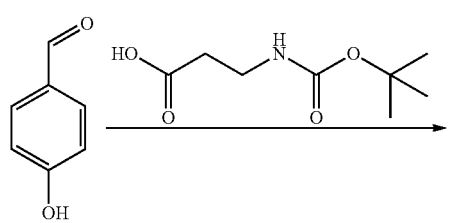

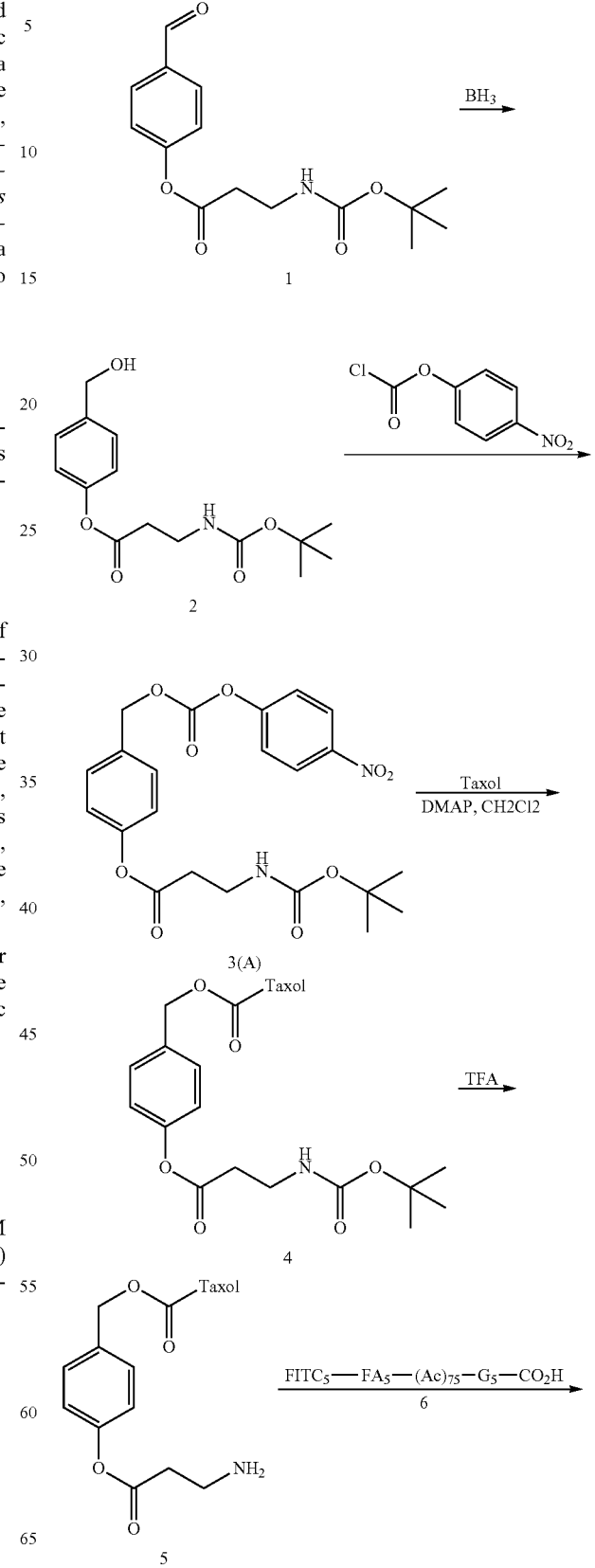

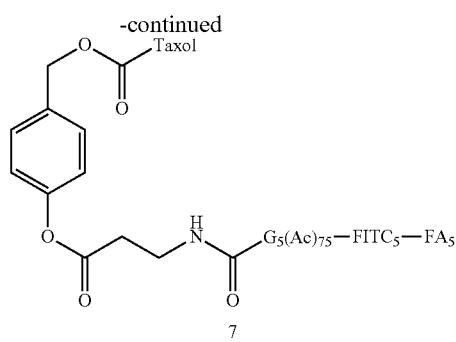

7

Step 1:

A 50 mL, solution of Boc-β-alanine (500 mg, 2.64 mmol), EDC (506 mg, 2.64 mmol), and DMAP (322 mg, 2.64 mmol) in methylene chloride was stirred at 0° C. for 20 min. 4-Hydroxybenzaldehyde (323 mg, 2.64 mmol) was then added slowly. The reaction mixture was stirred at 0° C. for 2 hour before it was warmed to RT and continued for over night. The reaction mixture was then diluted with EtOAc and H₂O and extractive work up to give a crude product which was purified by silica gel chromatography to afford a clear oil (712 mg, 92%).

MS (EI) m/e=294 (M+1)

Step 2:

The aldehyde 1 (775 mg, 2.64 mmol) was dissolved in 40 mL of dry THF and was cooled to 0° C. Boran in THF (1N solution, 2.64 mL) was added dropwise. The reaction mixture was for 2 h. MeOH (5 mL) was added slowly and the reaction mixture was warmed to RT in 1 h. Solvent was evaporated and the product was purified by chromatograph to afford the product as a white solid (625 mg, 80%).

MS (EI) m/e=296 (M+1)

Step 3:

The benzyl alcohol 2 (456 mg, 1.54 mmol) and p-nitrobenzyl chloroformate (934 mg, 4.63 mmol) were dissolved in 20 mL of methylene chloride. Pyridine (0.42 mL, 5.19 mmol) was added. White precipitate was formed during the addition process. The reaction mixture was stirred at RT over night. The reaction mixture was then diluted with EtOAc and water. Layers were separated and the aqueous layer was extracted with EtOAc×3. Combined organic solution was washed with 1N HCl, sat'd NaHCO₃ and brine. The crude mixture was purified by silica gel chromatography eluting with 15-25% EtOAc in Hexanes to afford the product as clear oil (520 mg, 73%).

MS (EI) m/e=461 (M+1)

Step 4:

Taxol (9.3 mg, 0.0103575 mmol) and 3 (4.75 mg, 0.0103575 mmol) were dissolved in dry methylene chloride (1 mL). A solution of DMAP (2.5 mg, 0.02715 mmol) in methylene chloride (1 mL) was added dropwise at room temperature. After addition, a light yellow color appeared. The reaction mixture was allowed to stir at room temperature for 3 hours when TLC indicated the reaction was complete. The reaction mixture was extracted with methylene chloride and water. The organic layers were combined and dried over MgSO₄. Solvent was evaporated after filtration. The residue was purified by column chromatography (silica gel, EtOAc: Hexanes 1:1) and pure product (10 mg, yield 82%) was obtained.

MS (EI) m/e=1197.5 (M+Na).

Step 5:

Taxol-linker conjugate 4 (10.0 mg, 0.008514 mmol) was dissolved in methylene chloride (1 mL). To above solution was added TFA (120 µL). The reaction mixture was stirred at room temperature and was checked with TLC until the reaction was complete in 20 minutes. The solvent was evaporated and the residue was purified by column chromatography (silica gel, CH₂Cl₂:MeOH 10:1). Product 5 was isolated as a white solid (8.0 mg, yield 87.4%).

MS (EI) m/e=1075.4 (M+H).

Step 6:

G5-Ac-Fl-FA-COOH (6), prepared as reported previously, (15.3 mg, 0.0004636 mmol) was dissolved in H₂O (5.2 mL), EDM (10.6 mg, 0.03488 mmol) was added. The reaction mixture was stirred for 2 hour at room temperature. A solution of 5 (10 mg, 0.0093 mmol) in DMF (4.3 mL) and DMSO (3.4 mL) was added dropwise. The reaction was allowed to stir at room temperature for three days. The solvent was removed by membrane filtration through a 10,000 MWCO membrane. The residue was further purified by passing through a Sephdex G-25 column and extensively washed with PBS buffer and water. Lyophilization gave final product 7 as orange colored solid (15.1 mg, yield 90%).

Example 3

Synthesis of Esterase Sensitive Linker 11B

A synthesis scheme of a dendrimer (e.g., G5 PAMAM dendrimer) conjugated to a therapeutic agent (e.g., Taxol) with an esterase sensitive linker (esterase sensitive elimination linker 11B) is shown below.

Scheme 2. Synthesis of dendrimer-Taxol conjugate through an esterase-sensitive linker 11

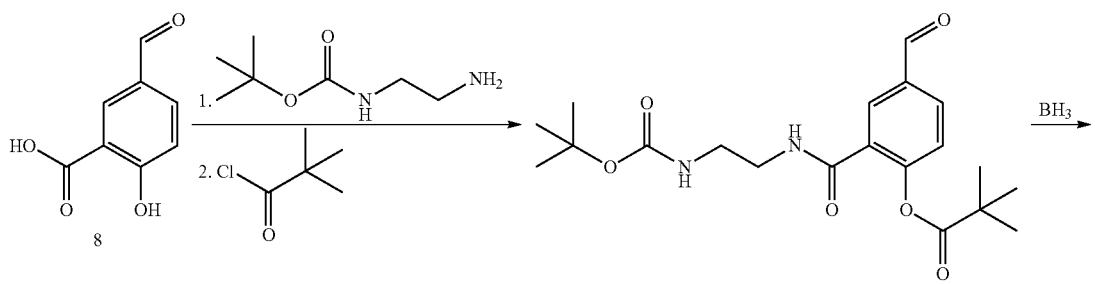

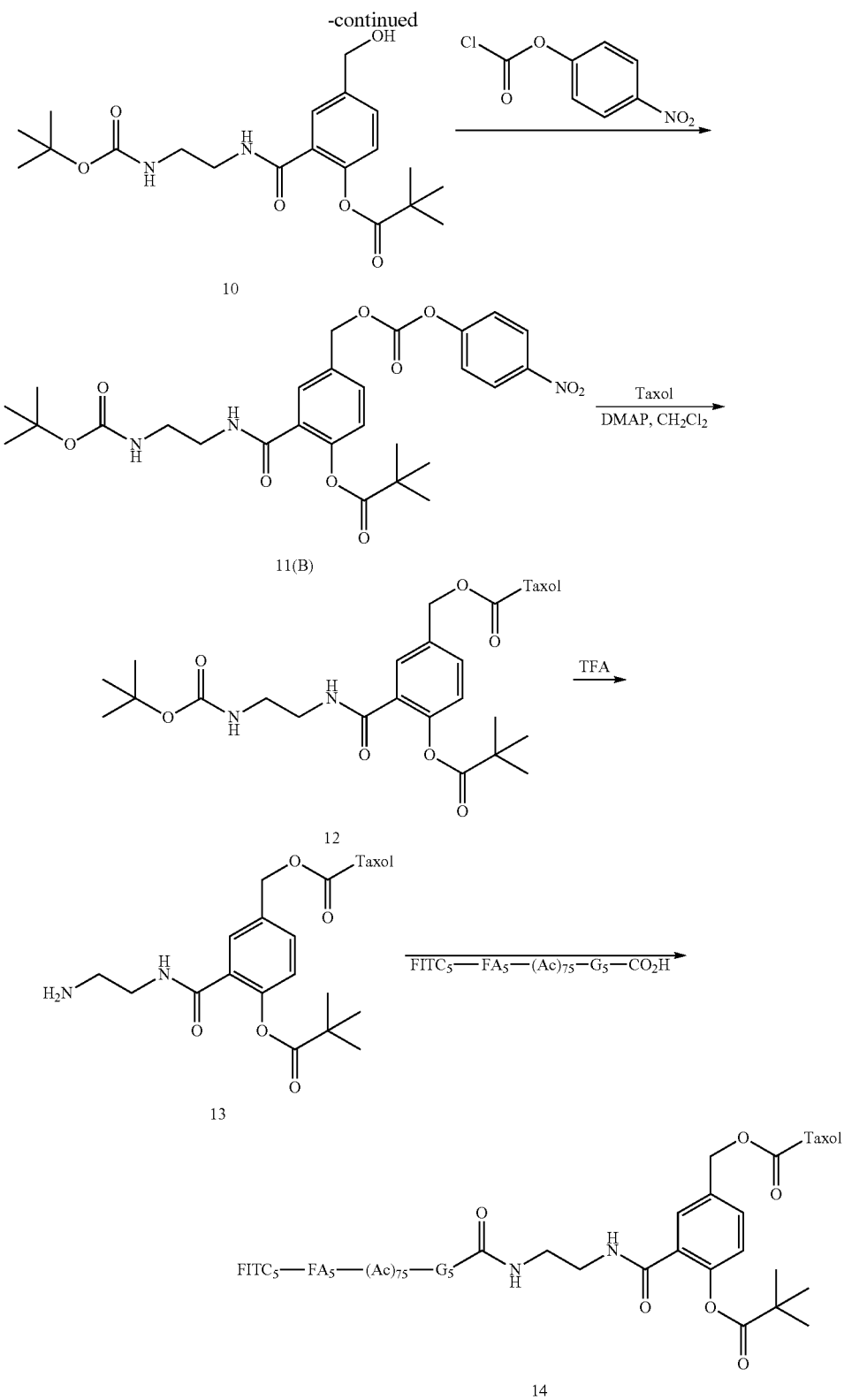

Step 1:

A mixture of 5-formyl-2-hydroxybenzoic acid 8 (1.66 g, 10 mmol), mono-Boc-ethylene diamine (1.60 g, 10 mmol), EDC methiodide (2.97 g, 10 mmol), and HOBT (1.35 g, 10 mmol) was dissolved in 40 mL of DMF at 0° C. The solution was stirred at this temperature for 1 h before it was warmed to RT. Stirring was continued for over night. The orange-yellow colored reaction mixture was cooled to 0° C. Triethylamine (2.8 mL, 20 mmol) was added followed by pivaloyl chloride (2.5 mL, 20 mmol). The reaction mixture was stirred for 2 hours and it was quenched by addition of 50 ml of water. EtOAc (200 mL) was added and the layers were separated. The aqueous layer was extracted with EtOAc×3. The combined organics was washed with 1N HCl, saturated NaHCO$_3$ solution, and brine sequentially and was dried with MgSO$_4$. After solvent was evaporated, the residue was purified by silica gel chromatography to afford the product 9 as a pale yellow solid (3.33 g, 85% 2 steps).

MS (EI) ink=xxx (M+1)

Step 2:

The aldehyde 9 (2.04 g, 5.20 mmol) was dissolved in 60 mL of dry THF and was cooled to 0° C. Boran in THF (1N solution, 5.46 mL) was added dropwise. The reaction mixture was for 2 h. MeOH (10 mL) was added slowly and the reaction mixture was warmed to RT in 2 h. Solvent was evaporated and the product was purified by chromatograph to afford the product as a white solid (2.02 g, 98%).

MS (EI) m/e=xxx (M+1)

Step 3:

The benzyl alcohol 10 (1.185 g, 3.0 mmol) and p-nitrobenzyl chloroformate (908 mg, 4.50 mmol) were dissolved in 30 mL of methylene chloride. Pyridine (0.49 mL, 6.0 mmol) was added. White precipitate was formed during the addition process. The reaction mixture was stirred at RT over night. The reaction mixture was then diluted with EtOAc and water. Layers were separated and the aqueous layer was extracted with EtOAc×3. Combined organic solution was washed with 1N HCl, sat'd NaHCO$_3$ and brine. The crude mixture was purified by silica gel chromatography eluting with 15-25% EtOAc in Hexanes to afford the product 11 as white solid (1.38 g, 82%).

MS (EI) m/e=560 (M+1)

Step 4:

In a 5 mL round bottle flask, taxol (20 mg, 0.02227 mmol) and linker 11 (35.8 mg, 0.02810 mmol) were dissolved in dry methylene chloride (2 mL). A solution of DMAP (5.7 mg, 0.04666 mmol) in methylene chloride (1 mL) was added dropwise at room temperature. After addition, a light yellow appeared. The reaction mixture was allowed to stir at room temperature for 3 hours. The reaction was monitored with TLC until the reaction was complete. The reaction mixture was extracted with methylene chloride and water. The organic layer was collected and dried over MgSO$_4$ and evaporated. The residue was purified by column chromatography (silica gel, AcOEt:Hexanes 1:1) and pure product (25.3 mg, yield 89%) was obtained.

MS (EI) m/e=1296.5 (M+Na).

Step 5:

To the taxol-linker conjugate 12 (12 mg, 0.009426 mmol) in methylene chloride (1 mL) was added TFA (120 µL). The reaction mixture was stirred at room temperature for 20 minutes and was checked with TLC until the reaction was complete. The solvent was evaporated and the residue was purified by column chromatography (silica gel, CH$_2$Cl$_2$:MeOH 10:1). Product 13 was isolated as a white solid (9.8 mg, yield 88%).

MS (EI) m/e=1174.5 (M+H).

Step 6:

G5-Ac-FI-FA-COOH (6), prepared as reported previously, (13.8 mg, 0.00041818 mmol) was dissolved in H$_2$O (5.2 mL), EDM (9.32 mg, 0.03136 mmol) was added. The reaction mixture was stirred for 2 hour at room temperature. A solution of 13 (9.8 mg, 0.0093 mmol) in DMF (4.3 mL) and DMSO (3.4 mL) was added dropwise. The reaction was allowed to stir at room temperature for three days. The solvent was removed by membrane filtration through a 10,000 MWCO membrane. The residue was further purified by passing through a Sephdex G-25 column and extensively washed with PBS buffer and water. Lyophilization gave final product 14 as orange colored solid (15.1 mg, yield 87%).

Example 4

Synthesis of Esterase Sensitive Linker 11C

A synthesis scheme of a dendrimer (e.g., G5 PAMAM dendrimer) conjugated to a therapeutic agent (e.g., Taxol) with an esterase sensitive linker (esterase sensitive elimination linker 11C) is shown below.

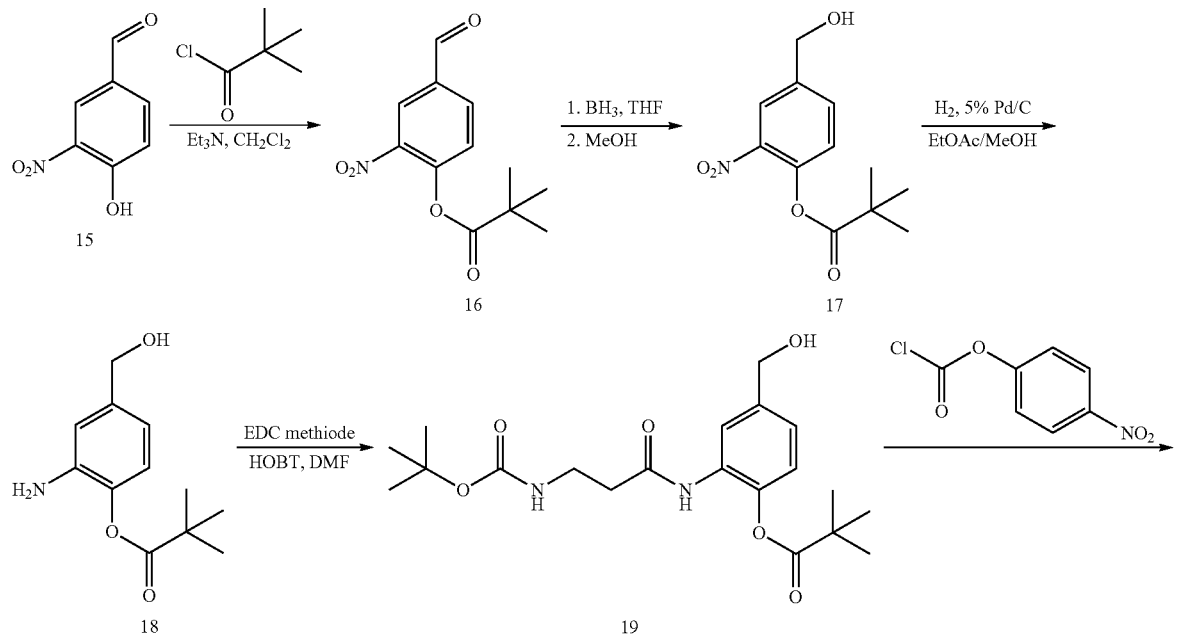

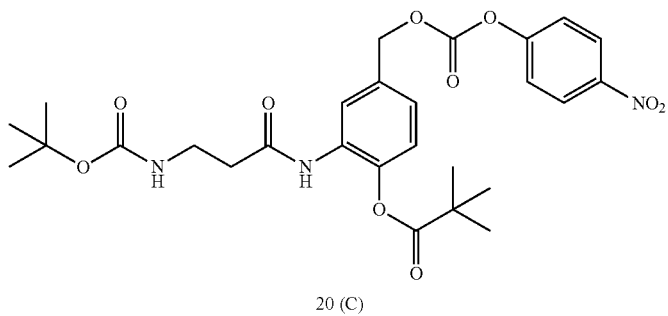

20 (C)

Example 5

Additional Self-Immorlative Linkers

The present invention is not limited by the type of self-immorlative linkers utilized. For example, cyclization based linkers can be used. Although a mechanism is not necessary to practice the present invention and the present invention is not limited to any particular mechanism, in some embodiments, a mechanism as shown below is utilized in a conjugate of the present invention:

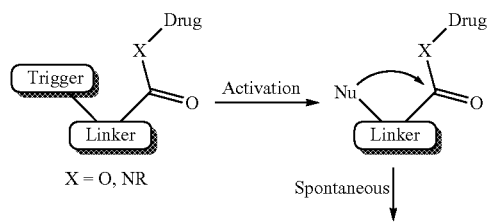

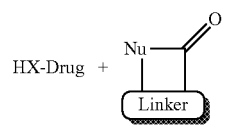

Thus, in some embodiments, the present invention provides synthesis of dendrimer conjugates utilizing cyclization linkers (e.g., designed as esterase cleavage substrates) as shown below:

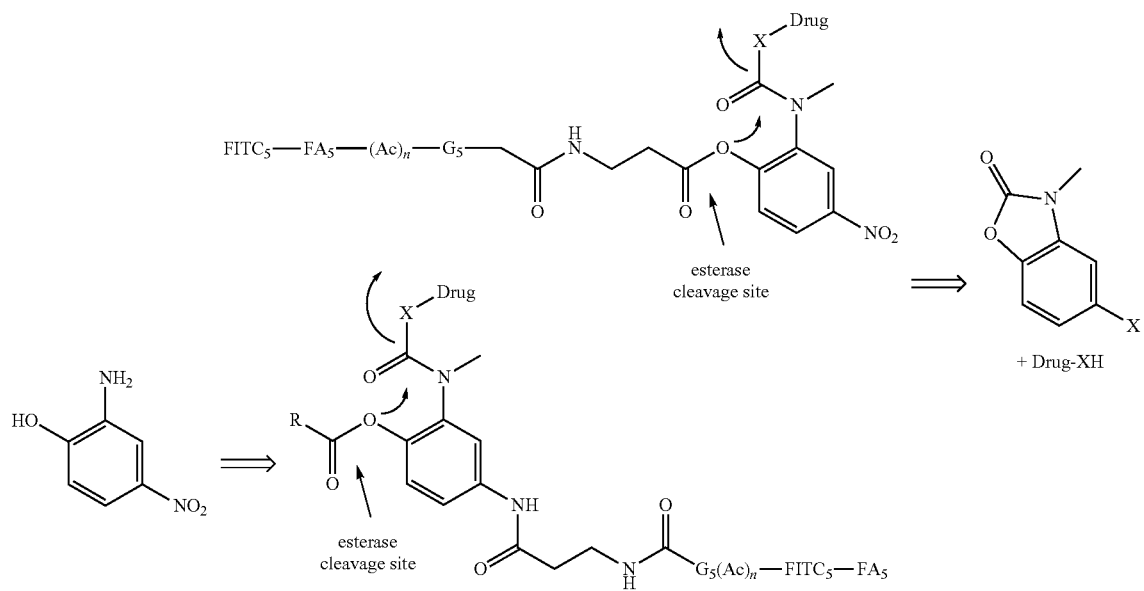

In some embodiments, the present invention provides syntheses of linkers C and D as shown below.

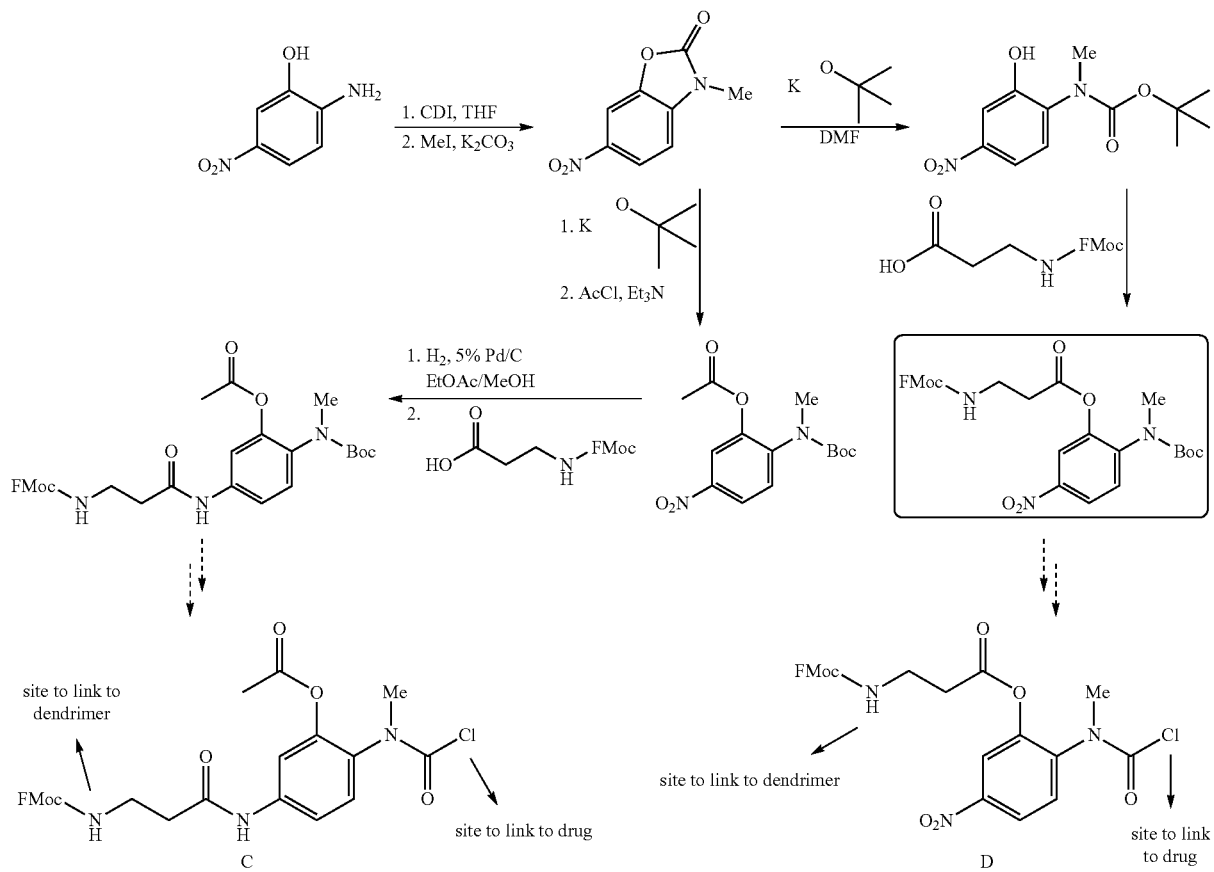

Example 6

Characterization of Dendrimer Conjugates

Experiments were conducted during development of embodiments of the invention in order to characterize release of drug from a dendrimer conjugate comprising a linker-drug component. The linker-drug components were characterized under esterase incubation conditions, utilizing HPLC as an analytical tool to monitor drug release. This approach provides an assessment regarding structural influences of the linkers. For example, characteristics of drug release from a linker (e.g., in the absence of a dendrimer) provides information regarding drug release from a linker conjugated to a dendrimer.

For example, the experiments were conducted to characterize the following two conjugates:

First Generation Linker-Drug(-Dendrimer) Conjugates

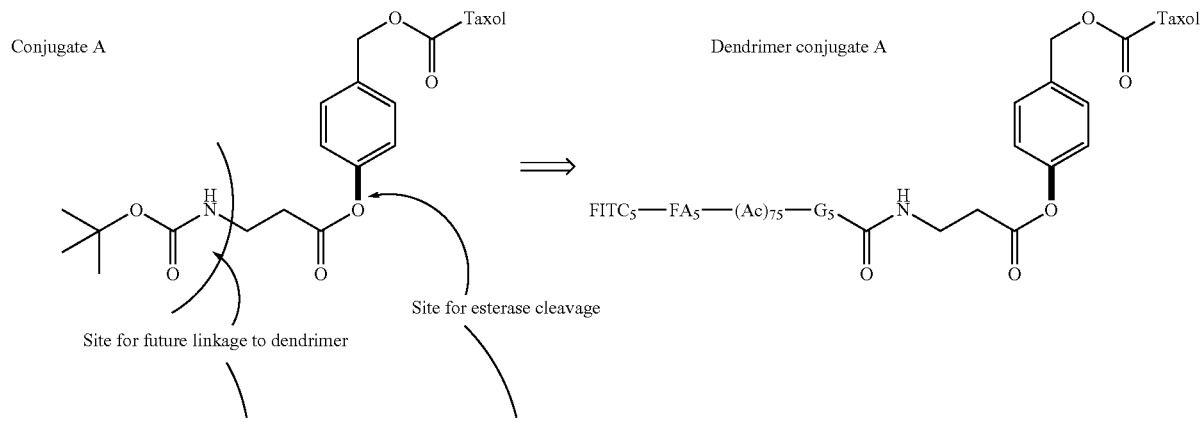

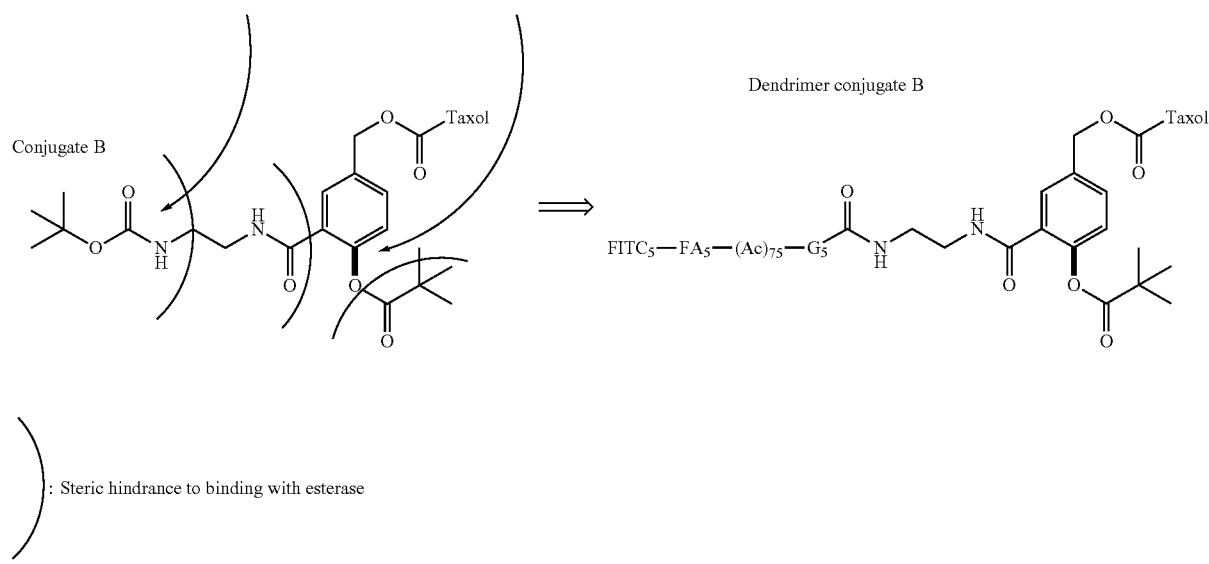

: Steric hindrance to binding with esterase

Figure 12:
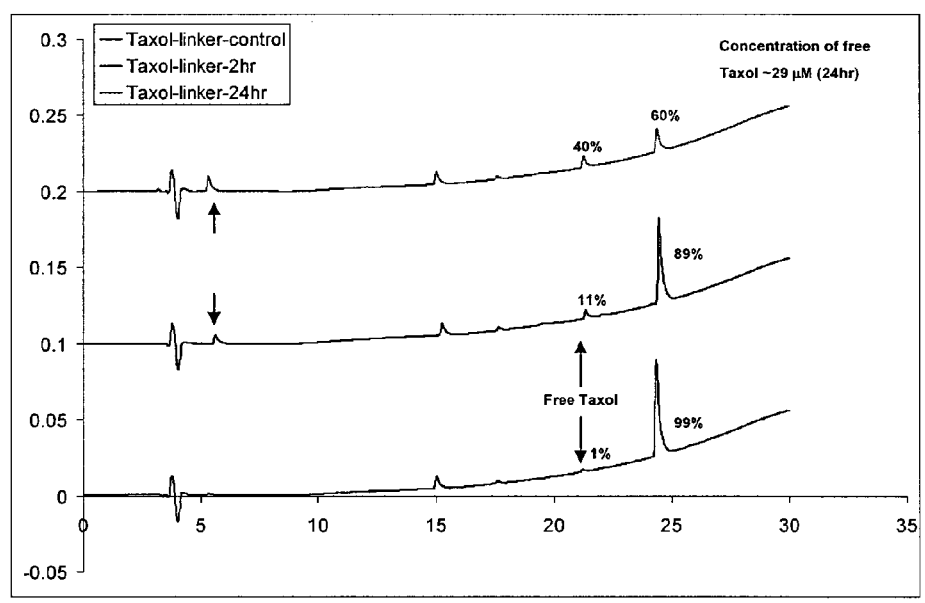
FIG. 12 shows the characterization of therapeutic compound release from dendrimer conjugates of the present invention.

When incubated with pig liver esterase for 2 hours, conjugate B showed minimal release and conjugate A showed ~11% release. Furthermore, conjugate A showed around 40% release at 24 h (See, e.g., FIG. 12).

Example 7

Second Generation Linkers

Characterization of linkers as described in Example 6 indicated that steric hindrance issues were inhibiting release of a therapeutic from the conjugates (e.g., due, in some embodiments, to inaccessibility of esterase to the linker). Based on this data, alternative approaches were generated and characterized. For example, in some embodiments, in order to relieve steric hindrance, lengths of the linkers were extended. Thus, the present invention provides additional, "second generation" linkers as described below.

Second Generation Linker-Drug(-Dendrimer) Conjugates Rational

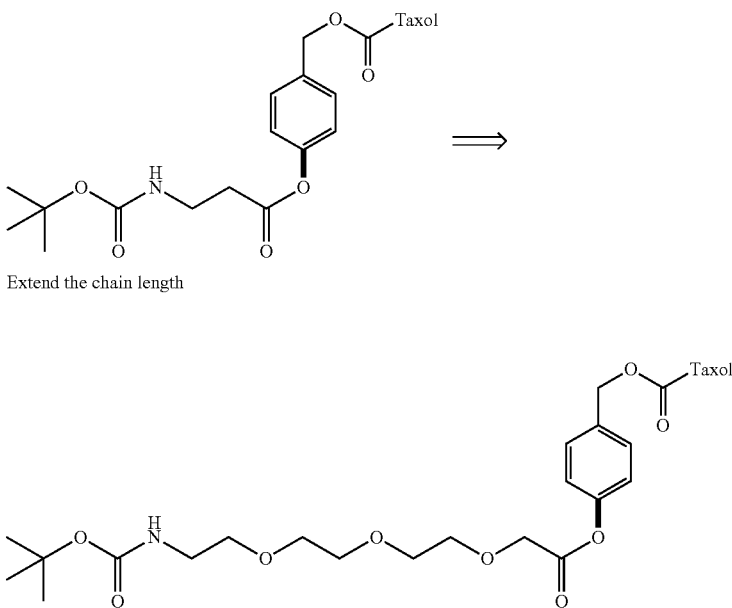

Extend the chain length

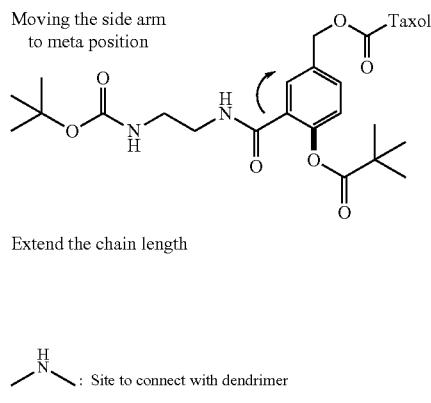

Moving the side arm to meta position

Extend the chain length

: Site to connect with dendrimer

R = Me, t-Bu

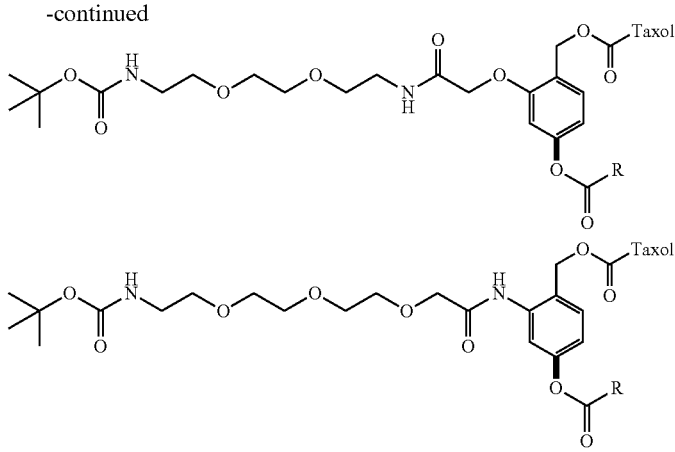

Figure 15:
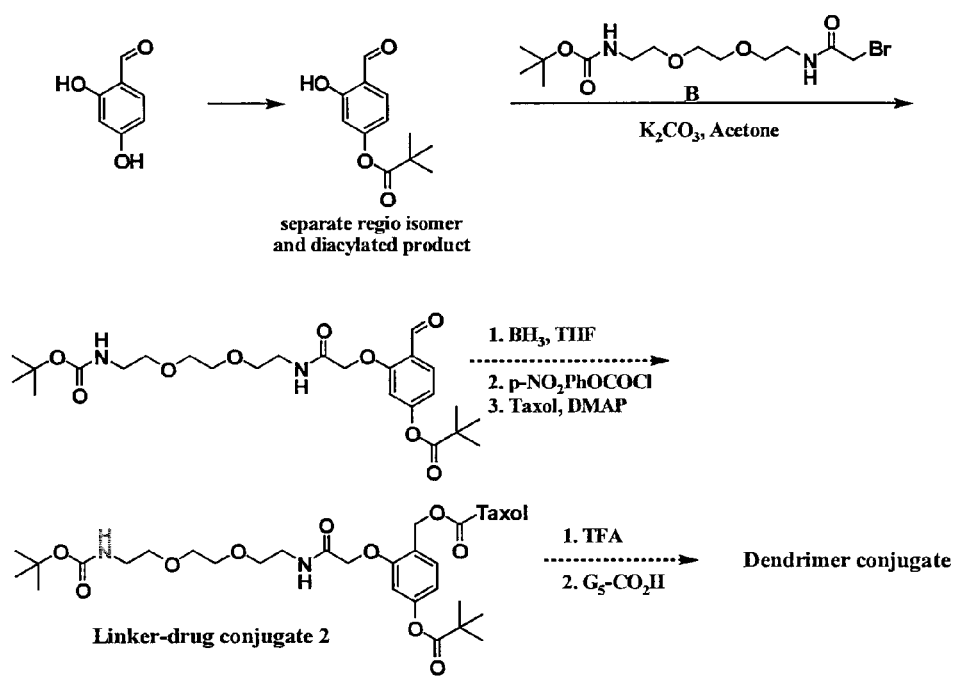
FIG. 15 shows a diagram of a dendrimer conjugate provided in some embodiments of the present invention.
Figure 16:
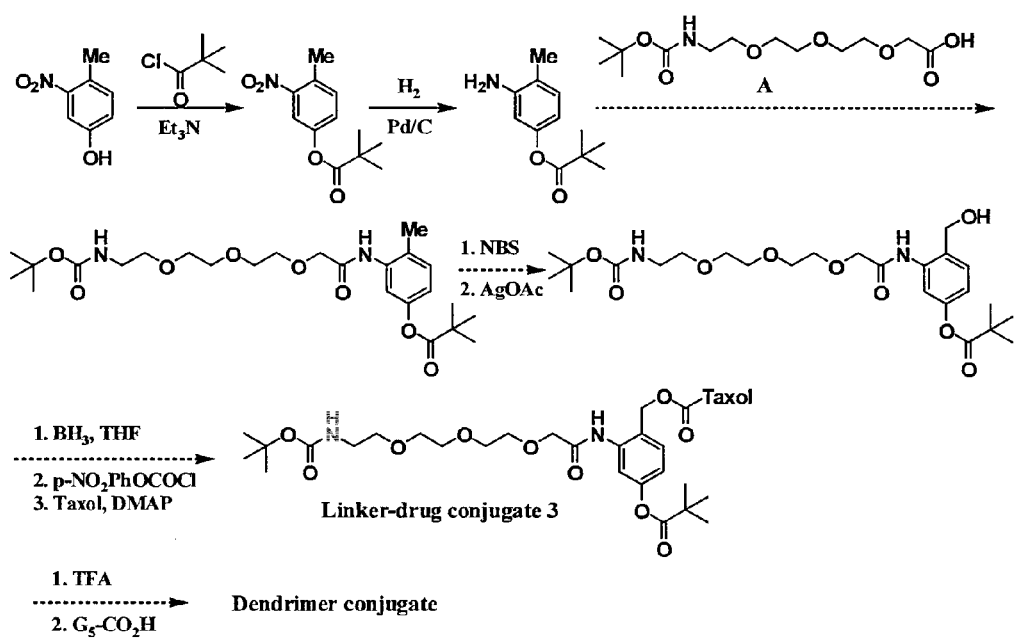
FIG. 16 shows a diagram of a dendrimer conjugate provided in some embodiments of the present invention.

Thus, in some embodiments, the present invention provides conjugates and methods of synthesizing and utilizing (e.g., therapeutically) the same with extended linkages as shown in FIG. 13. In some embodiments the present invention provides conjugates as shown in FIGS. 14-16.

Example 8

Hypoxia Induced Linkers

Figure 29:
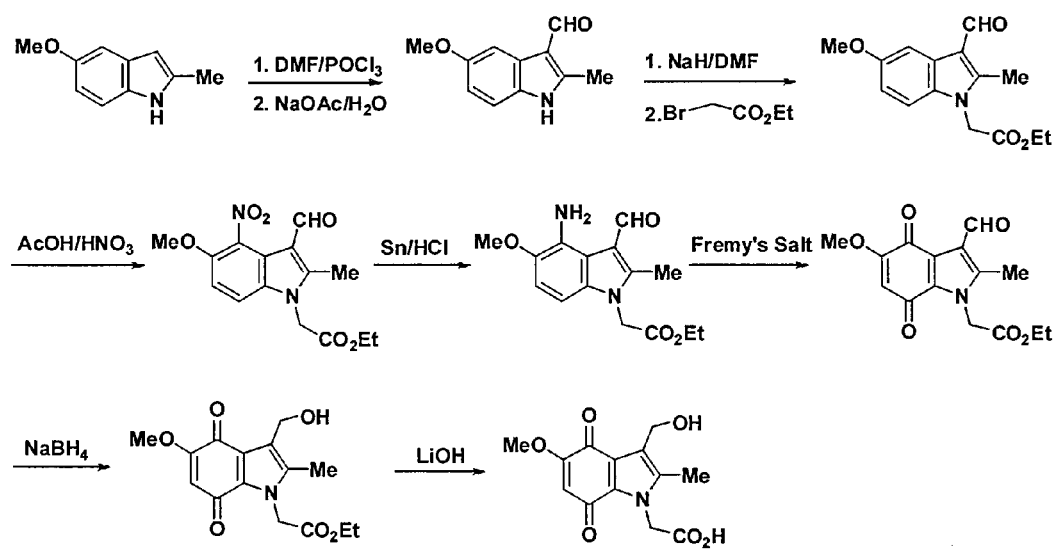
FIG. 29 shows a synthesis scheme for generating a dendrimer comprising a hypoxia induced linker.
Figure 30:
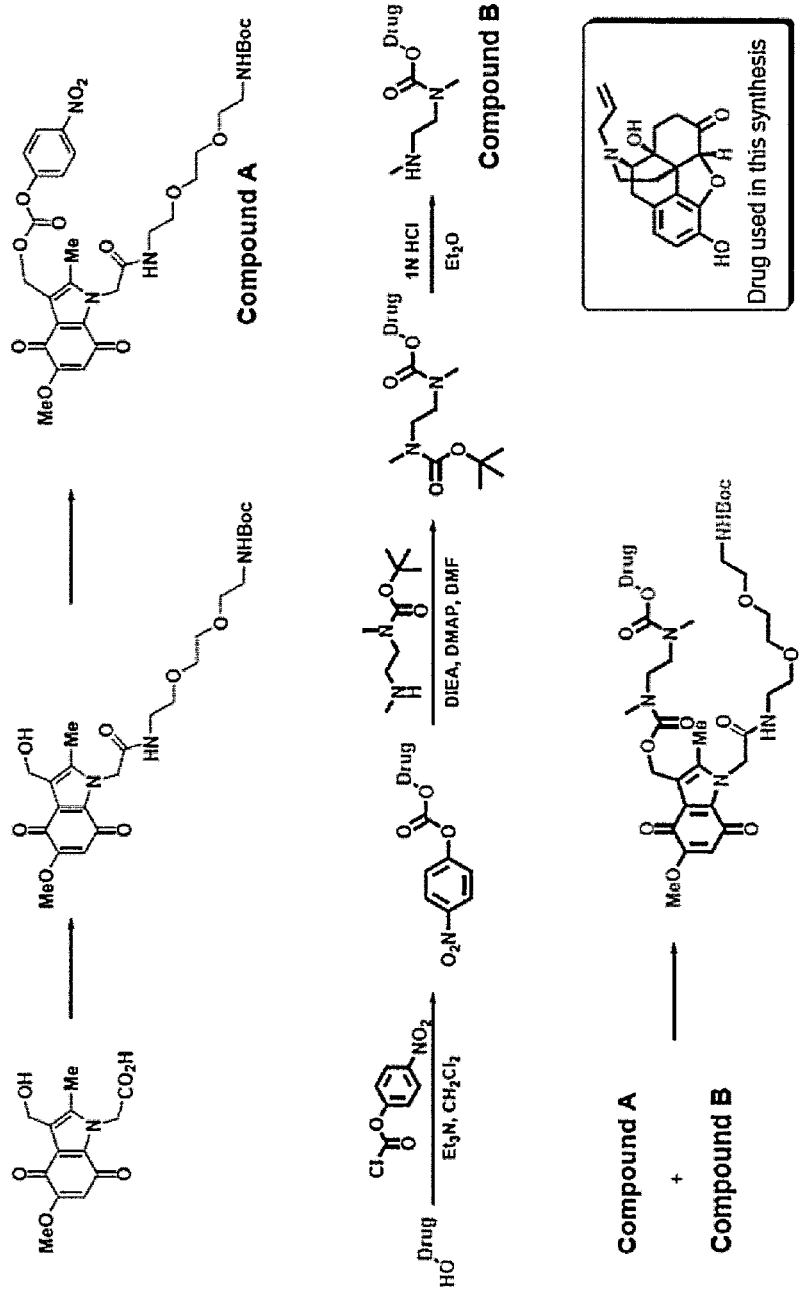
FIG. 30 shows a synthesis scheme for generating a dendrimer comprising a hypoxia induced linker.
Figure 31:
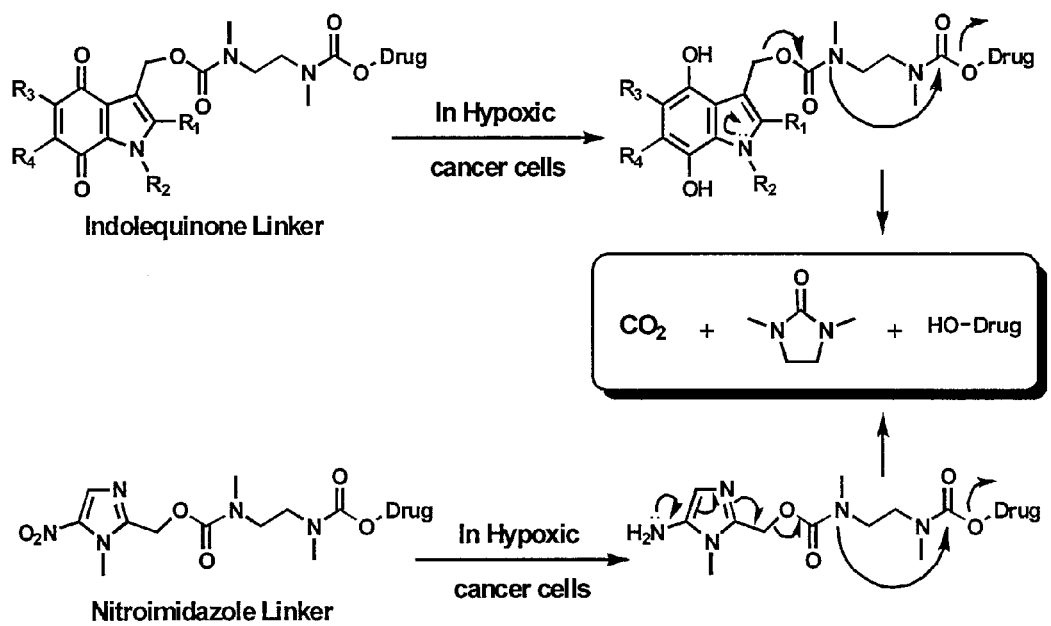
FIG. 31 shows a diagram depicting a mechanism of release of a therapeutic agent from a dendrimer comprising a hypoxia sensitive linker.

The present invention also provides dendrimers comprising small molecule linkers triggered by hypoxic environments (e.g., in and/or around cancer cells). In some embodiments, a dendrimer of the present invention comprises a indolequinone linker. In some embodiments, a dendrimer comprising a hypoxia cleavable linker is generated according to the synthesis scheme shown in FIG. 29. In some embodiments, a dendrimer comprising a hypoxia cleavable linker is generated according to the synthesis scheme shown in FIG. 30. The present invention is not limited to any particular mechanism of release of a therapeutic agent from a dendrimer comprising a linker triggered by a hypoxic environment. Indeed, a variety of mechanisms are contemplated including, but not limited to, a mechanism shown in FIG. 31.

Figure 32:
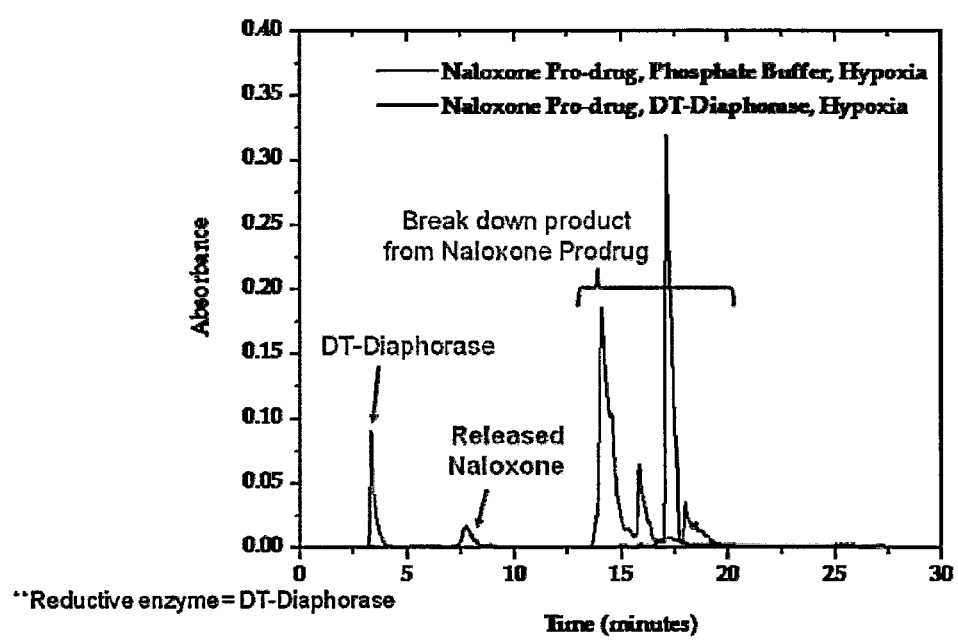
FIG. 32 shows release of Naloxone from [dendrimer-indolequinone linker-Naloxone prodrug] using the reductive enzyme DT-diaphorase.
Figure 33:
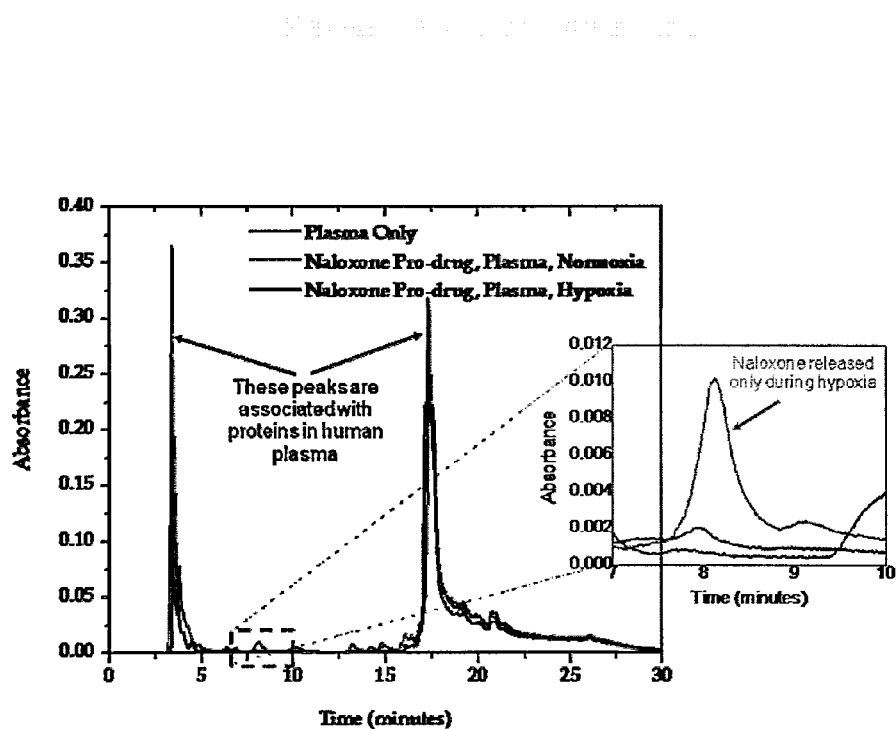
FIG. 33 shows release of Naloxone from [dendrimer-indolequinone linker-Naloxone prodrug] in human plasma under hypoxic conditions, but not under normoxic conditions.
Figure 34:
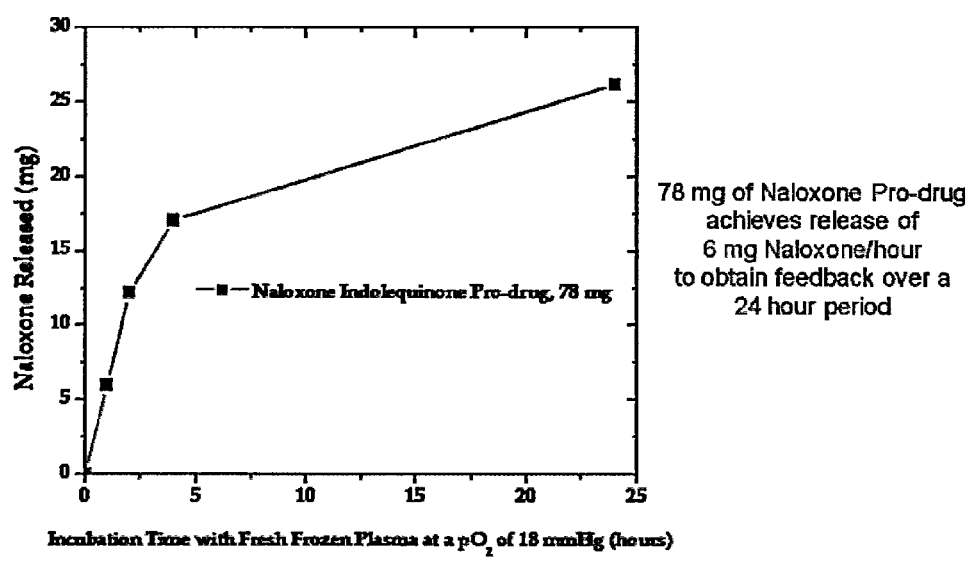
FIG. 34 shows hypoxia-induced release kinetics for Naloxone from [dendrimer-indolequinone linker-Naloxone prodrug] met or exceeded 6 mg Naloxone/hour at pO2 of 18 mmHg within fresh frozen plasma.

In particular, experiments conducted during the course of development of embodiments for the present invention demonstrated that incubation of a [dendrimer—indolequinone linker—Naloxone prodrug] with either fresh frozen plasma or a reductive results in release of the Naloxone prodrug under hypoxic conditions, but not under normoxic conditions. Indeed, FIG. 32 shows release of Naloxone from [dendrimer-indolequinone linker-Naloxone prodrug] using the reductive enzyme DT-diaphorase. FIG. 33 shows release of Naloxone from [dendrimer-indolequinone linker-Naloxone prodrug] in human plasma under hypoxic conditions, but not under normoxic conditions. FIG. 34 shows hypoxia-induced release kinetics for Naloxone from [dendrimer-indolequinone linker-Naloxone prodrug] met or exceeded 6 mg Naloxone/hour at pO2 of 18 mmHg within fresh frozen plasma.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

We claim:

1. A dendrimer conjugate comprising a linker,
   wherein said linker is selected from the group consisting of an elimination linker, a cyclization linker, a glucoronidase sensitive linker, a branched self-elimination linker, a heteroaromatic nitrogen containing compound linker, and a hypoxia induced linker,
   wherein said linker is conjugated to a G5 PAMAM dendrimer and at least one ligand selected from the group consisting of a therapeutic agent, an imaging agent, and a targeting agent.

2. The dendrimer conjugate of claim 1, wherein said G5 PAMAM dendrimer is conjugated to at least one ligand selected from the group consisting of a therapeutic agent, an imaging agent, and a targeting agent.

3. The dendrimer conjugate of claim 1, wherein said elimination linker is a 1,4 elimination linker.

4. The dendrimer conjugate of claim 1, wherein said elimination linker is a 1,6 elimination linker.

5. The dendrimer conjugate of claim 1, wherein said hypoxia induced linker is esterase sensitive.

6. The dendrimer of claim 1, wherein said hypoxia induced linker is indolequinone.

7. The dendrimer conjugate of claim 1, wherein said therapeutic agent is Naloxone.

8. The dendrimer of claim 1, wherein said imaging agent is selected from the group consisting of a radioactive label, fluorescein isothiocyanate (FITC), 6-TAMARA, acridine orange, and cis-parinaric acid.

9. The dendrimer of claim 1, wherein said targeting agent is selected from the group consisting of an agent binding a receptor selected from the group consisting of CFTR, EGFR, estrogen receptor, FGR2, folate receptor, IL-2 receptor, and VEGFR; an antibody that binds to a polypeptide selected from the group consisting of p53, Mucl, a mutated version of p53 that is present in breast cancer, HER-2, T and Tn haptens in glycoproteins of human breast carcinoma, and MSA breast carcinoma glycoprotein; an antibody selected from the group consisting of human carcinoma antigen, TP1 and TP3 antigens from osteocarcinoma cells, Thomsen-Friedenreich (TF) antigen from adenocarcinoma cells, KC-4 antigen from human prostrate adenocarcinoma, human colorectal cancer antigen, CA125 antigen from cystadenocarcinoma, DF3 antigen from human breast carcinoma, and p97 antigen of human melanoma, carcinoma or orosomucoid-related antigen; transferrin; and a synthetic tetanus toxin fragment.

10. The dendrimer of claim 1, wherein said therapeutic agent is selected from the group consisting of a chemotherapeutic agent, an anti-oncogenic agent, an anti-angiogenic agent, a tumor suppressor agent, an anti-microbial agent, an expression construct comprising a nucleic acid encoding a therapeutic protein, a pain relief agent, a pain relief agent antagonist, an agent designed to treat arthritis, an agent designed to treat inflammatory bowel disease, an agent designed to treat an autoimmune disease, and an agent designed to treat inflammatory pelvic disease.

* * * * *

SEQUENCE LISTING

```
<160> NUMBER OF SEQ ID NOS: 1

<210> SEQ ID NO 1
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: The residue at this position is linked to a
      7-methoxycoumarin-4-yl acetyl.
<220> FEATURE:
<221> NAME/KEY: MISC_FEATURE
<222> LOCATION: (7)..(7)
```

```
<223> OTHER INFORMATION: The residue at this position is linked to a
      2,4-dinitrophenyl group and NH2.

<400> SEQUENCE: 1

Tyr Glu Val Asp Gly Trp Lys
1               5
```